United States Patent
Satchi-Fainaro et al.

(10) Patent No.: US 9,259,482 B2
(45) Date of Patent: *Feb. 16, 2016

(54) CONJUGATES OF POLYMERS HAVING A THERAPEUTICALLY ACTIVE AGENT AND AN ANGIOGENESIS TARGETING MOIETY ATTACHED THERETO AND USES THEREOF IN THE TREATMENT OF ANGIOGENESIS RELATED DISEASES

(71) Applicants: Ramot at Tel-Aviv University Ltd., Tel-Aviv (IL); Fundacion de la Comunidad Valenciana Centro de Investigacion Principe Felipe, Valencia (ES)

(72) Inventors: Ronit Satchi-Fainaro, Tel-Aviv (IL); Maria Jesus Vicent Docon, Castellon (ES)

(73) Assignees: Ramot at Tel-Aviv University Ltd., Tel-Aviv (IL); Fundacion de la Comunidad Valenciana Centro de Investigacion Principe Felipe, Valencia (ES)

(*) Notice: Subject to any disclaimer, the term of this patent is extended or adjusted under 35 U.S.C. 154(b) by 0 days.

This patent is subject to a terminal disclaimer.

(21) Appl. No.: 14/082,224

(22) Filed: Nov. 18, 2013

(65) Prior Publication Data
US 2014/0079638 A1    Mar. 20, 2014

Related U.S. Application Data

(63) Continuation of application No. 12/993,853, filed as application No. PCT/IL2009/000510 on May 21, 2009, now Pat. No. 8,586,019.

(60) Provisional application No. 61/193,140, filed on Oct. 30, 2008, provisional application No. 61/071,886, filed on May 22, 2008.

(51) Int. Cl.
| A61K 31/74  | (2006.01) |
| A61K 47/48  | (2006.01) |
| A61K 31/336 | (2006.01) |
| A61K 31/337 | (2006.01) |
| G01N 33/68  | (2006.01) |
| A61K 49/00  | (2006.01) |

(52) U.S. Cl.
CPC ......... *A61K 47/48315* (2013.01); *A61K 31/336* (2013.01); *A61K 31/337* (2013.01); *A61K 47/48176* (2013.01); *A61K 47/48238* (2013.01); *A61K 47/48338* (2013.01); *A61K 49/00* (2013.01); *G01N 33/6893* (2013.01); *A61K 47/48* (2013.01); *G01N 2800/042* (2013.01); *G01N 2800/102* (2013.01); *G01N 2800/321* (2013.01); *G01N 2800/323* (2013.01)

(58) Field of Classification Search
CPC ...................................................... A61K 47/48
See application file for complete search history.

(56) References Cited

U.S. PATENT DOCUMENTS

| 6,884,817 B2 | 4/2005 | Li et al. |
| 7,803,903 B2 | 9/2010 | Kratz |
| 8,658,149 B2 | 2/2014 | Satchi-Fainaro et al. |
| 2002/0197261 A1 | 12/2002 | Li et al. |
| 2005/0257114 A1 | 11/2005 | Gorshe |
| 2005/0287114 A1 | 12/2005 | Wang et al. |
| 2007/0104719 A1 | 5/2007 | Carter et al. |
| 2008/0112919 A1 | 5/2008 | Satchi-Fainaro et al. |
| 2008/0279778 A1 | 11/2008 | Van et al. |
| 2010/0022615 A1 | 1/2010 | Fegley et al. |
| 2011/0135618 A1 | 6/2011 | Koch et al. |
| 2011/0286923 A1 | 11/2011 | Satchi-Fainaro et al. |
| 2014/0134111 A1 | 5/2014 | Satchi-Fainaro et al. |
| 2015/0017115 A1 | 1/2015 | Satchi-Fainaro et al. |

FOREIGN PATENT DOCUMENTS

| WO | WO 03/086178 | 10/2003 |
| WO | WO 03/086382 | 10/2003 |
| WO | WO 2004/062588 | 7/2004 |
| WO | WO 2006/012355 | 2/2006 |
| WO | WO 2006/084054 | 8/2006 |
| WO | WO 2007/090094 | 8/2007 |
| WO | WO 2008/034124 | 3/2008 |
| WO | WO 2008/094834 | 8/2008 |
| WO | WO 2008/124735 | 10/2008 |
| WO | WO 2008/141110 | 11/2008 |
| WO | WO 2009/141823 | 11/2009 |
| WO | WO 2009/141826 | 11/2009 |

(Continued)

OTHER PUBLICATIONS

International Preliminary Report on Patentability Dated Dec. 2, 2010 From the International Bureau of WIPO Application No. PCT/IL2009/000507.
International Preliminary Report on Patentability Dated Dec. 2, 2010 From the International Bureau of WIPO Application No. PCT/IL2009/000510.
International Preliminary Report on Patentability Dated Dec. 2, 2010 From the International Bureau of WIPO Application No. PCT/IL2009/000511.
International Search Report and the Written Opinion Dated Dec. 2, 2009 From the International Searching Authority Application No. PCT/IL09/00510.
International Search Report and the Written Opinion Dated Nov. 5, 2009 From the International Searching Authority Application No. PCT/IL09/00511.

(Continued)

*Primary Examiner* — Paul Dickinson

(57) ABSTRACT

Conjugates of a polymer having attached thereto an angiogenesis targeting moiety and a therapeutically active agent such as an anti-cancer agent or anti-angiogenesis agent, and processes of preparing same are disclosed.
Pharmaceutical compositions containing these conjugates and uses thereof in the treatment of angiogenesis-related medical conditions such as cancer and cancer metastases are also disclosed.

19 Claims, 19 Drawing Sheets
(4 of 19 Drawing Sheet(s) Filed in Color)

(56) References Cited

FOREIGN PATENT DOCUMENTS

| WO | WO 2009/141827 | 11/2009 |
|---|---|---|
| WO | WO 2013/132485 | 9/2013 |

OTHER PUBLICATIONS

International Search Report and the Written Opinion Dated Jun. 16, 2013 From the International Searching Authority Application No. PCT/IL2013/050195.
International Search Report and the Written Opinion Dated Nov. 25, 2009 From the International Searching Authority Application No. PCT/IL09/00507.
Notice of Allowance Dated Sep. 19, 2013 From the US Patent and Trademark Office U.S. Appl. No. 12/993,856.
Notice of Allowance Dated Jun. 21, 2013 From the US Patent and Trademark Office U.S. Appl. No. 12/993,853.
Office Action Dated Sep. 18, 2013 From the State Intellectual Property Office of the People's Republic of China Application No. 200980128588.6 and Its Translation Into English.
Office Action Dated Sep. 27, 2013 From the State Intellectual Property Office of the People's Republic of China Application No. 200980129400.X and Its Translation Into English.
Official Action Dated Mar. 4, 2013 From the US Patent and Trademark Office U.S. Appl. No. 12/993,856.
Official Action Dated Apr. 18, 2013 From the US Patent and Trademark Office U.S. Appl. No. 12/993,855.
Official Action Dated Jan. 31, 2013 From the US Patent and Trademark Office U.S. Appl. No. 12/993,853.
Restriction Official Action Dated Dec. 3, 2012 From the US Patent and Trademark Office U.S. Appl. No. 12/993,853.
Restriction Official Action Dated Feb. 5, 2013 From the US Patent and Trademark Office U.S. Appl. No. 12/993,855.
Restriction Official Action Dated Oct. 11, 2012 From the US Patent and Trademark Office U.S. Appl. No. 12/993,856.
Translation of Decision on Rejection Dated Mar. 12, 2013 From the State Intellectual Property Office of the People's Republic of China Application No. 200980128587.1.
Translation of Office Action Dated Aug. 1, 2012 From the State Intellectual Property Office of the People's Republic of China Application No. 200980128587.1.
Translation of Office Action Dated Mar. 1, 2013 From the State Intellectual Property Office of the People's Republic of China Application No. 200980129400.X.
Translation of Office Action Dated Jan. 5, 2012 From the State Intellectual Property Office of the People's Republic of China Application No. 200980128588.6.
Translation of Office Action Dated Apr. 11, 2012 From the State Intellectual Property Office Application No. 200980129400.X.
Translation of Office Action Dated Dec. 21, 2012 From the State Intellectual Property Office of the People's Republic of China Application No. 200980128588.6.
Translation of Office Action Dated Sep. 26, 2011 From the State Intellectual Property Office of the People's Republic of China Application No. 200980128587.1.
Baabur-Cohen et al. "Recent Progress in Polymer Therapeutics as Nanomedicines", Handbook of Harnessing Biomaterials in Nanomedicine: Preparation, Toxicity, and Applications, Chap.4: 77-122, 2012.
Chen et al. "Synthesis and Biological Evaluation of Dimeric RGD Peptide-Paclitaxel Conjugate as a Model for Integrin-Targeted Drug Delivery", Journal of Medicinal Chemistry, 48: 1098-1106, 2005.
Duncan "Polymer Conjugates as Anticancer Nanomedicines", Nature Reviews Cancer, 6: 688-701, Sep. 2006.
Eldar-Boock et al. "Integrin-Assisted Drug Delivery of Nano-Scaled Polymer Therapeutics Bearing Paclitaxel", Biomaterials, 32(15): 3862-3874, May 2011.
Greco et al. "Combination Therapy: Opportunities and Challenges for Polymer-Drug Conjugates as Anticancer Nanomedicines", Advanced Drug Delivery Reviews, 61: 1203-1213, 2009.

Hrubý et al. "Hydroxybisphosphonate-Containing Polymeric Drug-Delivery Systems Designed for Targeting Into Bone Tissue", Journal of Applied Polymer Science, 101: 3192-3201, 2006.
Marsili et al. "Interaction of DDSDEEN Peptide With N-CAM Protein. Possible Mechanism Enhancing Neuronal Differentiation", Peptides, 29: 2232-2242, 2008.
Meerum Terwogt et al. "Phase I Clinical and Pharmacokinetic Study of PNU166945, A Novel Water-Soluble Polymer-Conjugated Prodrug of Paclitaxel", Anti-Cancer Drug, 12: 315-323, 2001.
Mitra et al. "Comparison of Polymeric Conjugates of Mono- and Bi-Cyclic RGD Peptide for Targeting Tumor Angiogenesis", 2006 National Biotechnology Conference, The AAPS Journal, 8(S1): # 127, 2006. § 1, 3-4.
Mitra et al. "Polymeric Conjugates of Mono- and Bi-Cyclic ???3 Binding Peptides for Tumor Targeting", Journal of Controlled Release, 114: 175-183, 2006.
Mitra et al. "Polymeric Conjugates of Mono- and Bi-Cyclic $\alpha v\beta 3$ Binding Peptides for Tumor Targeting", Journal of Controlled Release, 114: 175-183, 2006.
Mitra et al. "Polymer-Peptide Conjugates for Angiogenesis Targeted Tumor Radiotherapy", Nuclear Medicine and Biology, 33: 43-52, 2006.
O'Hare et al. "Polymeric Drug-Carriers Containing Doxorubicin and Melanocyte-Stimulating Hormone: In Vitro and In Vivo Evaluation Against Murine Melanoma", Journal of Drug Targeting, 1: 217-229, 1993.
Pan et al. "Backbone Degradable Multiblock N-(2-Hydroxypropyl)Methacrylamide Copolymer Conjugates via Reversible Addition Fragmentation Chain Transfer Polymerization and Thiol-Ene Coupling Reaction", Biomacromolecules, 12(1): 247-252, Jan. 10, 2011.
Pan et al. "Water-Soluble HPMA Copolymer-Prostaglandin E1, Conjugates Conatining a Cathepsin K Sensitive Spacer", Journal of Drug Targeting, 14(6): 425-435, 2006. Abstract.
Satchi-Fainaro et al. "Synthesis and Characterization of a Catalytic Antibody-HPMA Copolymer-Conjugate as a Tool for Tumor Selective Prodrug Activation", Bioorganic & Medicinal Chemistry, 10(9): 3023-3029, 2002.
Satchi-Fainaro et al. "Targeting Angiogenesis With a Conjugate of HPMA Copolymer and TNP-470", Nature Medicine, 10(3): 255-261, Mar. 2004.
Segal et al. "Enhanced Anti-Tumor Activity and Safety Profile of Targeted Nano-Scaled HPMA Copolymer-Alendronate-TNP-470 Conjugate in the Treatment of Bone Malignances", Biomaterials, 32(19): 4450-4463, Jul. 2011.
Segal et al. "Targeting Angiogenesis-Dependent Calcified Neoplasms Using Combines Polymer Therapeutics", PLoS One, 4(4): e5233-1-e5233-16, Apr. 2009.
Seymour et al. "Hepatic Drug Targeting: Phase I Evaluation of Polymer-Bound Doxorubicin", Journal of Clinical Oncology, 20(6): 1668-1676, Mar. 15, 2002.
Uludag "Bisphosphonates as a Foundation of Drug Delivery to Bone", Current Pharmaceutical Design, 8: 1929-1944, 2002.
Van Hagen et al. "Evaluation of a Radiolabelled Cyclic DTPA-RGD Analogue for Tumour Imaging and Radionuclide Therapy", International Journal of Cancer, 90(4): 186-198, Aug. 2000.
Wang et al. "Paclitaxel at Ultra Low Concentrations Inhibits Angiogenesis Without Affecting Cellular Microtube Assembly", Anti-Cancer Drugs, 14: 13-19, 2003.
Supplementary European Search Report and the European Search Opinion Dated Sep. 10, 2014 From the European Patent Office Application No. 09750179.3.
Miller et al. "Targeting Bone Metastases With a Bispecific Anticancer and Antiangiogenic Polymer-Alensronate-Taxane Conjugate", Angewandte Chemie International Edition, XP002680271, 48(16): 2949-2954, 2009. 'HPMA-Alendronate-TNP470 Conjugate, for Treating Bone Cancer'.
Wang et al. "Synthesis and Evaluation of Water-Soluble Polymeric Bont-Targeted Drug Delivery Systems", Bioconjugate Chemistry, XP002290582, 14: 853-859, Jan. 2003. 'Polymer-Fluorescein-Alendronate Conjugate'.

(56) References Cited

OTHER PUBLICATIONS

Supplementary European Search Report and the European Search Opinion Dated Jul. 21, 2014 From the European Patent Office Application No. 09750278.5.
Segal et al. "Design and Development of Polymer Conjugates as Anti-Angiogenic Agents", Advanced Drug Delivery Reviews, XP026698380, 61(13): 1159-1176, Nov. 12, 2009. Sections 3, 4, p. 1164-1168.
Wan et al. "Targeting Endothelial Cell Using HPMA Copolymer-Doxorubicin-RGD Conjugates", Proceedings of the 30th Annual Meeting of the International Symposium on Controlled Release Bioactive Materials, XP009178957, 30: 491-492, #491, Jan. 1, 2003.
Official Action Dated May 1, 2014 From the US Patent and Trademark Office U.S. Appl. No. 14/158,881.
Communication Pursuant to Rule 164(1) EPC and the Supplementary Partial European Search Report Dated Nov. 17, 2014 From the European Patent Office Application No. 09750275.1.
Official Action Dated Dec. 15, 2014 From the US Patent and Trademark Office U.S. Appl. No. 14/158,881.
Alavi et al. "Chemoresistance of Endothelial Cells Induced by Basic Fibroblast Growth Factor Depends on Raf-1-Mediated Inhibition of the Proapoptotic Kinase, ASK1", Cancer Research, XP055136030, 67(6): 2766-2772, Mar. 15, 2007. Abstract, Fig.2C.
Lee et al. "Anthracycline Chemotherapy Inhibits HIF-1 Transcriptional Activity and Tumor-Induced Mobilization of Circulating Angiogenic Cells", Proc. Natl. Acad. Sci, USA, PNAS, XP055135983, 106(7): 2353-2358, Feb. 17, 2009. Abstract.
Miller et al. "A Novel Bi-Specific Targeting Agent Based on a Polymer-Alendronate-Taxane Conjugate to Target Metastatic Prostate Carcinomas", Proceedings of the American Association for Cancer Research Annual Meeting, XP009179745, 49: 84-85, # 369, Apr. 2008. & 99th Annual Meeting of the American Association for Cancer Research, AACR, San Diego, CA, USA, Apr. 12-16, 2008. Title, Abstract.
Rihova et al. "Clinical Implications of N-(2-Hydroxypropyl)Methacrylamide Copolymers", Current Pharmaceutical Biotechnology, XP008124188, 4(5): 311-322, Oct. 1, 2003. p. 313, col. 1, Penultimate, p. 314, col. 1 Last Line, p. 316, Fig.4.

Poly-L-Glutamic acid (PGA)

Paclitaxel (PTX)

PGA-PTX conjugate

PGA-c(RADfk) conjugate

PGA-E-c(RGDfk)$_2$ conjugate

PGA-PTX-c(RGDfk) conjugate

PGA-c(RGDfk) conjugate

PGA-PTX-E-c(RGDfk)₂

PGA-PTX-c(RADfk)

PGA-TNP-470-c(RGDfk) conjugate

```
                        SEQUENCE LISTING

<160> NUMBER OF SEQ ID NOS: 51

<210> SEQ ID NO 1
<211> LENGTH: 3
<212> TYPE: PRT
<213> ORGANISM: Artificial sequence
<220> FEATURE:
<223> OTHER INFORMATION: Synthetic peptide

<400> SEQUENCE: 1

Arg Gly Asp
1

<210> SEQ ID NO 2
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: A cyclic peptide
<220> FEATURE:
<221> NAME/KEY: misc_feature
<222> LOCATION: (7)..(11)
<223> OTHER INFORMATION: A cyclic peptide

<400> SEQUENCE: 2

Arg Gly Asp Phe Lys Glu Arg Gly Asp Phe Lys
1               5                   10

<210> SEQ ID NO 3
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
```

```
<223> OTHER INFORMATION: Cyclic peptide

<400> SEQUENCE: 3

Arg Gly Asp Tyr Lys Glu Arg Gly Asp Tyr Lys
1               5                   10

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Arg Gly Asp Phe Lys
1               5

<210> SEQ ID NO 5
<211> LENGTH: 12
<212> TYPE: PRT
<213> ORGANISM: Artificial sequence
<220> FEATURE:
<223> OTHER INFORMATION: Synthetic peptide

<400> SEQUENCE: 5

Lys Ala Cys Asp Cys Arg Gly Asp Cys Phe Cys Gly
1               5                   10

<210> SEQ ID NO 6
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: misc_feature
<222> LOCATION: (12)..(12)
<223> OTHER INFORMATION: 99MTC conjugate

<400> SEQUENCE: 6

Lys Ala Cys Asp Cys Arg Gly Asp Cys Phe Cys Gly
1               5                   10

<210> SEQ ID NO 7
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: misc_feature
<222> LOCATION: (12)..(12)
<223> OTHER INFORMATION: 90Y conjugate

<400> SEQUENCE: 7

Lys Ala Cys Asp Cys Arg Gly Asp Cys Phe Cys Gly
1               5                   10

<210> SEQ ID NO 8
<211> LENGTH: 3
<212> TYPE: PRT
```

```
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA Copolymer-Doxorubicin conjugate

<400> SEQUENCE: 8

Arg Gly Asp
1

<210> SEQ ID NO 9
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: Cyclic peptide

<400> SEQUENCE: 9

Arg Gly Asp Phe Lys
1               5

<210> SEQ ID NO 10
<211> LENGTH: 4
<212> TYPE: PRT
<213> ORGANISM: Artificial sequence
<220> FEATURE:
<223> OTHER INFORMATION: Synthetic peptide

<400> SEQUENCE: 10

Gly Phe Leu Gly
1

<210> SEQ ID NO 11
<211> LENGTH: 8
<212> TYPE: PRT
<213> ORGANISM: Artificial sequence
<220> FEATURE:
<223> OTHER INFORMATION: Synthetic peptide

<400> SEQUENCE: 11

Gly Pro Leu Gly Ile Ala Gly Gln
1               5

<210> SEQ ID NO 12
<211> LENGTH: 2
<212> TYPE: PRT
<213> ORGANISM: Artificial sequence
<220> FEATURE:
<223> OTHER INFORMATION: Synthetic peptide

<400> SEQUENCE: 12

Phe Lys
1

<210> SEQ ID NO 13
<211> LENGTH: 6
<212> TYPE: PRT
<213> ORGANISM: Artificial sequence
<220> FEATURE:
<223> OTHER INFORMATION: Synthetic peptide

<400> SEQUENCE: 13

Phe Val Gly Leu Ile Gly
```

```
<210> SEQ ID NO 14
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic Acid conjugate
<220> FEATURE:
<221> NAME/KEY: misc_feature
<222> LOCATION: (1)..(5)
<223> OTHER INFORMATION: Cyclic peptide

<400> SEQUENCE: 14

Arg Ala Asp Phe Lys
1               5

<210> SEQ ID NO 15
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic Acid conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide

<400> SEQUENCE: 15

Arg Gly Asp Phe Lys Glu Arg Gly Asp Phe Lys
1               5                   10

<210> SEQ ID NO 16
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic acid -Paclitaxel conjugate
<220> FEATURE:
<221> NAME/KEY: misc_feature
<222> LOCATION: (1)..(5)
<223> OTHER INFORMATION: Cyclic peptide

<400> SEQUENCE: 16

Arg Gly Asp Phe Lys
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
```

```
<223> OTHER INFORMATION: Polyglutamic acid conjugate
<220> FEATURE:
<221> NAME/KEY: misc_feature
<222> LOCATION: (1)..(5)
<223> OTHER INFORMATION: Cyclic peptide

<400> SEQUENCE: 17

Arg Gly Asp Phe Lys
1               5

<210> SEQ ID NO 18
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic acid -Paclitaxel conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide

<400> SEQUENCE: 18

Arg Gly Asp Phe Lys Glu Arg Gly Asp Phe Lys
1               5                   10

<210> SEQ ID NO 19
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic acid -Paclitaxel conjugate
<220> FEATURE:
<221> NAME/KEY: misc_feature
<222> LOCATION: (1)..(5)
<223> OTHER INFORMATION: Cyclic peptide

<400> SEQUENCE: 19

Arg Ala Asp Phe Lys
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic acid -(TNP-470) conjugate
<220> FEATURE:
<221> NAME/KEY: misc_feature
<222> LOCATION: (1)..(5)
<223> OTHER INFORMATION: Cyclic peptide

<400> SEQUENCE: 20

Arg Ala Asp Phe Lys
1               5
```

```
<210> SEQ ID NO 21
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic acid -(TNP-470) conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide

<400> SEQUENCE: 21

Arg Gly Asp Phe Lys Glu Arg Gly Asp Phe Lys
1               5                   10

<210> SEQ ID NO 22
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyethyleneglycol-Paclitaxel conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide

<400> SEQUENCE: 22

Arg Gly Asp Phe Lys Glu Arg Gly Asp Phe Lys
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide
<220> FEATURE:
<221> NAME/KEY: misc_feature
<222> LOCATION: (11)..(11)
<223> OTHER INFORMATION: Paclitaxel conjugate

<400> SEQUENCE: 23

Arg Gly Asp Phe Lys Glu Arg Gly Asp Phe Lys
1               5                   10
```

```
<210> SEQ ID NO 24
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic acid conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (5)..(5)
<223> OTHER INFORMATION: Oregon Green-cadaverine conjugate

<400> SEQUENCE: 24

Arg Ala Asp Phe Lys
1               5

<210> SEQ ID NO 25
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Polyglutamic acid conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide
<220> FEATURE:
<221> NAME/KEY: misc_feature
<222> LOCATION: (11)..(11)
<223> OTHER INFORMATION: Oregon Green-cadaverine conjugate

<400> SEQUENCE: 25

Arg Gly Asp Phe Lys Glu Arg Gly Asp Phe Lys
1               5                   10

<210> SEQ ID NO 26
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (6)..(10)
<223> OTHER INFORMATION: Cyclic peptide

<400> SEQUENCE: 26

Arg Gly Asp Phe Lys Arg Gly Asp Phe Lys
1               5                   10

<210> SEQ ID NO 27
<211> LENGTH: 3
<212> TYPE: PRT
<213> ORGANISM: Artificial sequence
```

```
<220> FEATURE:
<223> OTHER INFORMATION: Synthetic peptide

<400> SEQUENCE: 27

Arg Ala Asp
1

<210> SEQ ID NO 28
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha V beta3 conjugate

<400> SEQUENCE: 28

Arg Gly Asp
1

<210> SEQ ID NO 29
<211> LENGTH: 3
<212> TYPE: PRT
<213> ORGANISM: Artificial sequence
<220> FEATURE:
<223> OTHER INFORMATION: Synthetic peptide

<400> SEQUENCE: 29

Gly Phe Gly
1

<210> SEQ ID NO 30
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Cit

<400> SEQUENCE: 30

Xaa Val
1

<210> SEQ ID NO 31
<211> LENGTH: 2
<212> TYPE: PRT
<213> ORGANISM: Artificial sequence
<220> FEATURE:
<223> OTHER INFORMATION: Synthetic peptide

<400> SEQUENCE: 31

Arg Arg
1

<210> SEQ ID NO 32
<211> LENGTH: 4
<212> TYPE: PRT
<213> ORGANISM: Artificial sequence
<220> FEATURE:
<223> OTHER INFORMATION: Synthetic peptide

<400> SEQUENCE: 32

Gly Phe Ala Leu
```

```
<210> SEQ ID NO 33
<211> LENGTH: 4
<212> TYPE: PRT
<213> ORGANISM: Artificial sequence
<220> FEATURE:
<223> OTHER INFORMATION: Synthetic peptide

<400> SEQUENCE: 33

Ala Leu Ala Leu
1

<210> SEQ ID NO 34
<211> LENGTH: 3
<212> TYPE: PRT
<213> ORGANISM: Artificial sequence
<220> FEATURE:
<223> OTHER INFORMATION: Synthetic peptide

<400> SEQUENCE: 34

Gly Leu Gly
1

<210> SEQ ID NO 35
<211> LENGTH: 3
<212> TYPE: PRT
<213> ORGANISM: Artificial sequence
<220> FEATURE:
<223> OTHER INFORMATION: Synthetic peptide

<400> SEQUENCE: 35

Gly Phe Gly
1

<210> SEQ ID NO 36
<211> LENGTH: 6
<212> TYPE: PRT
<213> ORGANISM: Artificial sequence
<220> FEATURE:
<223> OTHER INFORMATION: Synthetic peptide

<400> SEQUENCE: 36

Gly Phe Leu Gly Phe Lys
1               5

<210> SEQ ID NO 37
<211> LENGTH: 4
<212> TYPE: PRT
<213> ORGANISM: Artificial sequence
<220> FEATURE:
<223> OTHER INFORMATION: Synthetic peptide

<400> SEQUENCE: 37

Gly Leu Phe Gly
1

<210> SEQ ID NO 38
<211> LENGTH: 8
<212> TYPE: PRT
<213> ORGANISM: Artificial sequence
<220> FEATURE:
<223> OTHER INFORMATION: Synthetic peptide

<400> SEQUENCE: 38

Gly Pro Gln Gly Ile Ala Gly Gln
1               5
```

```
<210> SEQ ID NO 39
<211> LENGTH: 8
<212> TYPE: PRT
<213> ORGANISM: Artificial sequence
<220> FEATURE:
<223> OTHER INFORMATION: Synthetic peptide

<400> SEQUENCE: 39

Gly Pro Gln Gly Ile Trp Gly Gln
1               5

<210> SEQ ID NO 40
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Cyclic peptide

<400> SEQUENCE: 40

Arg Ala Asp Phe Lys
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(6)
<223> OTHER INFORMATION: Cyclic peptide

<400> SEQUENCE: 41

Glu Arg Gly Asp Phe Lys
1               5

<210> SEQ ID NO 42
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate

<400> SEQUENCE: 42

Gly Phe Leu Gly
1

<210> SEQ ID NO 43
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjuagte
<220> FEATURE:
<221> NAME/KEY: MOD_RES
<222> LOCATION: (4)..(4)
```

<223> OTHER INFORMATION: P-nitrophenol (ONp) activated amino acid

<400> SEQUENCE: 43

Gly Phe Leu Gly
1

<210> SEQ ID NO 44
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide

<400> SEQUENCE: 44

Arg Gly Asp Phe Lys Glu Arg Gly Asp Phe Lys
1               5                   10

<210> SEQ ID NO 45
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (6)..(10)
<223> OTHER INFORMATION: Cyclic peptide
<220> FEATURE:
<221> NAME/KEY: misc_feature
<222> LOCATION: (10)..(10)
<223> OTHER INFORMATION: TFA conjugate

<400> SEQUENCE: 45

Arg Gly Asp Phe Lys Arg Gly Asp Phe Lys
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA-TNP-470 conjugate

<400> SEQUENCE: 46

Lys Ala Cys Asp Cys Arg Gly Asp Cys Phe Cys Gly
1               5                   10

<210> SEQ ID NO 47
<211> LENGTH: 11
<212> TYPE: PRT
<213> ORGANISM: Artificial sequence

```
<220> FEATURE:
<223> OTHER INFORMATION: Synthetic peptide
<220> FEATURE:
<221> NAME/KEY: misc_feature
<223> OTHER INFORMATION: Sodium salt
<220> FEATURE:
<221> NAME/KEY: misc_feature
<222> LOCATION: (1)..(1)
<223> OTHER INFORMATION: Polyglutamic acid -Paclitaxel conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide

<400> SEQUENCE: 47

Arg Gly Asp Phe Lys Glu Arg Gly Asp Phe Lys
1               5                   10

<210> SEQ ID NO 48
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: Sodium salt
<220> FEATURE:
<221> NAME/KEY: misc_feature
<222> LOCATION: (1)..(1)
<223> OTHER INFORMATION: Polyglutamic acid conjugate
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (7)..(11)
<223> OTHER INFORMATION: Cyclic peptide

<400> SEQUENCE: 48

Arg Gly Asp Phe Lys Glu Arg Gly Asp Phe Lys
1               5                   10

<210> SEQ ID NO 49
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(10)
<223> OTHER INFORMATION: Cyclic peptide
<220> FEATURE:
<221> NAME/KEY: misc_feature
<222> LOCATION: (10)..(10)
<223> OTHER INFORMATION: Paclitaxel conjugate

<400> SEQUENCE: 49

Arg Gly Asp Phe Lys Arg Gly Asp Phe Lys
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (6)..(10)
<223> OTHER INFORMATION: Cyclic peptide

<400> SEQUENCE: 50

Arg Ala Asp Phe Lys Arg Ala Asp Phe Lys
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Cyclic peptide
<220> FEATURE:
<221> NAME/KEY: misc_feature
<222> LOCATION: (6)..(10)
<223> OTHER INFORMATION: Cyclic peptide
<220> FEATURE:
<221> NAME/KEY: misc_feature
<222> LOCATION: (10)..(10)
<223> OTHER INFORMATION: Paclitaxel conjugate

<400> SEQUENCE: 51

Arg Ala Asp Phe Lys Arg Ala Asp Phe Lys
1               5                   10
```

CONJUGATES OF POLYMERS HAVING A THERAPEUTICALLY ACTIVE AGENT AND AN ANGIOGENESIS TARGETING MOIETY ATTACHED THERETO AND USES THEREOF IN THE TREATMENT OF ANGIOGENESIS RELATED DISEASES

RELATED APPLICATIONS

This application is a continuation of U.S. patent application Ser. No. 12/993,853 filed on Nov. 22, 2010, which is a National Phase of PCT Patent Application No. PCT/IL2009/000510 having International filing date of May 21, 2009, which claims the benefit of priority of U.S. Provisional Patent Application Nos. 61/193,140 filed on Oct. 30, 2008 and 61/071,886 filed on May 22, 2008. The contents of the above Applications are all incorporated herein by reference.

FIELD AND BACKGROUND OF THE INVENTION

The present invention, in some embodiments thereof, relates to novel chemical conjugates and to uses thereof in therapy and diagnosis and, more particularly, but not exclusively, to novel conjugates of polymers having attached thereto an angiogenesis targeting moiety and an anti-angiogenesis agent and to uses thereof in monitoring and treating medical conditions associated with angiogenesis.

Angiogenesis is a biological process that involves the sprouting of new blood vessels from pre-existing ones and plays a crucial role in disease development and progression. Angiogenesis is a complex process in which endothelial cells serve as a building block for blood vessel expansion. This process involves an extensive interplay among cells, growth factors, and extracellular membrane (ECM) components. It is regulated through a fine balance between pro-angiogenic and anti-angiogenic molecules.

Pathological angiogenesis has been demonstrated in several diseases, including atherosclerosis, cancer, hypertension, rheumatoid arthritis, diabetes and diabetes related complications such as diabetic retinopathy. Tumor growth and metastasis are particularly dependent on the degree of angiogenesis. Tumor angiogenesis is the proliferation of a network of blood vessels that penetrate into cancerous tumors in order to supply nutrients and oxygen and remove waste products, thus leading to tumor growth. Tumor angiogenesis involves hormonal stimulation and activation of oncogenes, expression of angiogenic growth factors, extravasation of plasma protein, deposition of a provisional ECM, degradation of ECM, and migration, proliferation and elongation of endothelial capillaries.

Inhibition of further vascular expansion has therefore been the focus of active research for cancer therapy. Many drugs have been developed, which target different steps in this multi-step tumor angiogenesis process. However, most of these drugs were shown to be cytostatic rather than cytotoxic and thus do not cause a substantial reduction of tumor volume during the first stage of treatment.

There are currently eight approved anti-cancer therapies with recognized antiangiogenic properties. These agents, which interrupt critical cell signaling pathways involved in tumor angiogenesis and growth, can be divided into two primary categories: (1) monoclonal antibodies directed against specific proangiogenic factors and/or their receptors; (Avastin, Erbitux, Vectibix, Herceptin) and (2) small molecule tyrosine kinase inhibitors (TKIs) of multiple proangiogenic growth factor receptors (Tarceva, Nexavar, Sutent, Iressa). Inhibitors of mTOR (mammalian target of rapamycin) represent a third, smaller category of antiangiogenic therapies with one currently approved agent (Torisel). In addition, at least two other approved angiogenic agents may indirectly inhibit angiogenesis through mechanisms that are not completely understood (Velcade, Thalidomide/Celgene)

The first FDA-approved angiogenesis inhibitor, Bevacizumab (Avastin, Genentech) a monoclonal antibody to vascular endothelial growth factor (VEGF), has recently been approved for metastatic colon cancer treatment in conjunction with standard conventional chemotherapy.

The largest class of drugs that block angiogenesis are the multi-targeted tyrosine kinase inhibitors (TKIs) that target the VEGF receptor (VEGFR). These drugs such as sunitinib (Sutent, Pfizer), Sorafenib (Nexavar, Bayer/Onyx Pharmaceuticals) and Erlotinib (Tarceva, Gennentech/OSI/Roche) have the advantages of hitting multiple targets, convenient oral administration, and cost effectiveness. While these drugs exhibit promising efficacy, their use is limited by their lack of target specificity, which leads to unexpected toxicity [Cabebe et al. *Curr Treat Options Oncol* 2007; 8:15-27].

Tumor endothelial cells are drug sensitive for long time periods and may be treated with cytotoxic agents in an "anti-angiogenic dosing schedule". This dosing schedule involves the administration of chemotherapy in low doses, well below the maximum tolerated dose (MTD), in close intervals for extended periods of time ("metronomic dosing"). As a result, acute toxicity should be avoided and the drugs may be administered during longer periods, eventually converting cancer to a chronic manageable disease.

The microtubule-interfering agent Paclitaxel (PTX) is a clinically well-established and highly-effective anti-neoplastic drug used as a monotherapy and in combination therapy mainly for the treatment of prostate, breast, ovarian, and non-small cell lung cancers and it is the drug of choice for the treatment of metastatic breast cancer. It has also shown anti-angiogenic and pro-apoptotic properties [Oldham et al. 2000 *Int. J Oncol.* 16:125-132]. However, due to the hydrophobic nature of the drug, solubilizing agents such as Cremophor EL or ethanol are required for its administration. PTX causes severe adverse side effects such as neutropenia, neuropathies, and when solubilized in Cremophor EL causes hypersensitivity reactions. In addition, only a small amount of the drug localizes in the tumor and the drug is substrate to efflux pumps in particular p-glycoprotein, resulting in multiple drug resistance.

Water-soluble copolymers such as hydroxypropyl methacrylate (HPMA) and PGA are biocompatible, non-immunogenic and non-toxic carriers that enable specific delivery into tumor tissue (Satchi-Fainaro et al. *Nat Med* 2004; 10: 255-261). These macromolecules do not diffuse through normal blood vessels but rather accumulate selectively in the tumor site because of the enhanced permeability and retention (EPR) effect. This phenomenon of passive diffusion through the hyperpermeable neovasculature and localization in the tumor interstitium is observed in many solid tumors for macromolecular agents and lipids.

Conjugation of anti-cancer drugs to copolymers, such as HPMA or PGA, has been suggested so as to restrict the passage through the blood brain barrier and to prolong the circulating half-life of the drugs, hence inhibiting the growth of tumor endothelial and epithelial cells by exposing the cells to the conjugated drugs in the circulation for a longer time compared to the free drugs.

U.S. Pat. No. 6,884,817 teaches compositions comprising a chemotherapeutic and/or anti-angiogenic drug, conjugated to a water-soluble polyamino acid or soluble metal chelator.

The taught compositions provide water soluble taxoids which overcome the drawbacks associated with the insolubility of the drugs themselves, and further improve the delivery of the drugs to tumor tissue and affect a controlled release of the conjugated drug. According to the teachings of in U.S. Pat. No. 6,884,817, an exemplary such conjugate of the anticancer drug paclitaxel and polyglutamate, exhibited superior antitumor activity together with a reduced level of toxicity, as compared with the anti-tumor agent paclitaxel alone.

The conjugate paclitaxel-polyglutamate OPAXIO™ (paclitaxel poliglumex, CT-2103) (Formerly known as XYOTAX™) showed promising results in phase III trials and is currently being evaluated for marketing approval.

U.S. patent application Ser. No. 12/117,678 having publication No. 2008/0279778 also teaches polyglutamate polymers conjugated to a plurality of drugs for use in drug targeting, stabilizing and imaging applications. A HPMA copolymer conjugate of paclitaxel has also been described by Meerum Terwogt et al. [*Anticancer drugs* 2001; 12:315-323]. This conjugate was aimed at improving drug solubility and providing controlled release of paclitaxel. In this conjugate, the paclitaxel is linked to the HPMA copolymer through an ester bond, and is hence released from the polymer by non-tissue specific hydrolytic or enzymatic (esterases) degradation of the ester bond, thereby inducing the commonly observed toxicities of paclitaxel.

WO 03/086382 teaches conjugates of water-soluble polymers and the anti-angiogenesis agent TNP-470, and their use as anti-tumor agents, in particular their use as carriers of TNP-470 into tumor vessels, and their effect on the neurotoxicity of TNP-470. According to the teachings of WO 03/086382, an exemplary such conjugate, HPMA-(TNP-470) conjugate (caplostatin), exhibited superior antitumor activity together with a reduced level of toxicity, as compared with TNP-470 alone.

WO 03/086178 teaches a method for decreasing or inhibiting disorders associated with vascular hyperpermeability by the administration of an effective amount of an anti-angiogenesis compound or a compound capable of increasing cell-cell contacts by stabilizing tight junction's complexes and increasing contact with the basement membrane. The compounds taught by WO 03/086178 are endostatin, thrombospondin, angiostatin, tumastatin, arrestin, recombinant EPO, and polymer conjugated TNP-470. According to the teachings of WO 03/086178, an exemplary such conjugate, HPMA-(TNP-470) inhibited vascular endothelial growth factor (VEGF)-induced vessel hyperpermeability and inhibited endothelial cell mediated angiogenesis both in vitro and in vivo.

Integrins are a class of receptors involved in the mechanism of cell adhesion. Alterations in the function of these receptors are responsible for the occurrence of a number of pathologic manifestations, such as, for example, defective embryogenesis, blood coagulation, osteoporosis, acute renal failure, retinopathy and cancer, particularly metastasis. Since the 1980s it is well recognized that integrins play a key role in cell matrix interactions and hence in angiogenesis.

The integrins are heterodimeric transmembrane glycoproteins that compose a diverse family of 19α and eight β subunits. An integrin with a well-characterized involvement in angiogenesis and tumor invasiveness is $\alpha_v\beta_3$. The $\alpha_v\beta_3$ integrin is a molecular marker that differentiates newly formed capillaries from their mature counterparts. This integrin is expressed in various malignant tumors. Inhibition of the $\alpha_v\beta_3$ mediated cell matrix interaction leads to apoptosis of activated endothelial cells and to disruption of blood vessel formation. In contrast, $\alpha_v\beta_3$ is not strongly expressed on quiescent endothelial cells, thus treatment with $\alpha_v\beta_3$ antagonists does not affect pre-existing blood vessels [Brooks et al. *Science* 1994; 264:569-571].

$\alpha_v\beta_3$ integrins therefore play an important role in adhesion, motility, growth and differentiation of endothelial cells. $\alpha_v\beta_3$ integrins are known to bind the RGD sequence (Arg-Gly-Asp; SEQ ID NO:1), which constitutes the recognition domain of different proteins, such as laminin, fibronectin and vitronectin. The RGD sequence represent the minimal amino acid domain, in several extracellular matrix proteins, which has been demonstrated to be the binding site of the transmembrane integrins proteins family [Bazzoni et al. 1999, *Current Opinion in Cell Biology*; (11) pp. 573-581]. Indeed it was shown that replacement of even a single amino acid of this short sequence results in loss of binding activity to integrins. Integrins mediates the attachment of endothelial cells to sub-matrix proteins that form the basement membrane of the capillary. Although all endothelial cells use the integrin to anchor to the extraluminal submatrix, the $\alpha_v\beta_3$ integrins are found on the luminal surface of the endothelial cell only during angiogenesis. Thus, agents that target this integrin actually target endothelial cells involved in angiogenesis.

The $\alpha_v\beta_3$ integrin is overexpressed on proliferating endothelial cells such as those present in growing tumors, as well as on some tumor cells of various origins. Expression of endothelial $\alpha_v\beta_3$ integrin receptor in aggressive breast carcinomas and glioblastomas is a marker of poor prognosis.

It has been demonstrated that RGD-containing peptides, either isolated from phage peptides library or biochemically synthesized, were able to compete with extracellular matrix proteins on binding to integrins [Haubner et al. 1997, *Angew. Chem. Int. Ed. Engl.*; (36) pp. 1374-1389]. Tumor-induced angiogenesis can be targeted in vivo by antagonizing the $\alpha_v\beta_3$ integrin with small peptides containing the RGD amino acid sequence.

It has been further found that the substrate specificity of RGD-containing peptides results from the different conformations of the RGD sequence in different matrix proteins. For example, the bis-cyclic peptide E-[c(RGDfK)$_2$] (SEQ ID NO:2) is a ligand-based vascular-targeting agent that binds to integrin $\alpha_v\beta_3$.

Encoded by a growth factor-inducible immediate-early gene, Cyr61 (also known as CCN1) is a cysteine-rich matricellular protein that supports cell adhesion and induces adhesion signaling. Furthermore, Cyr61 stimulates endothelial cell migration and enhances growth factor induced DNA synthesis in culture and therefore induces angiogenesis in vivo. Mechanistically, Cyr61 acts as a non-RGD-containing ligand of integrin receptors. Functional blockade of $\alpha_v\beta_3$, a Cyr61 integrin receptor, is specifically cytotoxic towards Cyr61-overexpressing breast cancer cells and a specific $\alpha_v\beta_3$-RGD peptidomimetic agent prevents $\alpha_v\beta_3$ from binding to its ligand, Cyr61.

Cyr61 plays a key role in both the maintenance and the enhancement of a malignant phenotype in breast cancer.

Cyr61 is overexpressed in about 30% of invasive breast carcinomas, whereas Cyr61 expression levels in normal breast tissues are negligible. It has been recently shown that Cyr61 overexpression can render human breast cancer cells highly resistant to Paclitaxel. Pharmacological interference with the Cyr61/$\alpha_v\beta_3$ interaction fully restores Paclitaxel efficacy in Cyr61 overexpressors, thus implying that a previously unrecognized Cyr61/$\alpha_v\beta_3$-driven cellular signaling actively modulates breast cancer cell growth and chemosensitivity.

Chen et al. reported [J. Med. Chem. 2005; 48:1098-1106] the synthesis and antitumor activity of paclitaxel (PTX) conjugated with a bis-cyclic RGD (E[RGDyK]$_2$) (SEQ ID NO:3) in a metastatic breast cancer cell line.

Mitra et al. report [*Journal of Controled Release* 2006; 28: 175-183] the biodistribution and tumor targeting properties of N-(2-hydroxypropyl)methacrylamide (HPMA) copolymer based conjugates of mono-(RGDfK) (SEQ ID NO:4) and doubly cyclized (RGD4C; SEQ ID NO:5) $\alpha_v\beta_3$ binding peptides.

WO 2006/012355 teaches an anti-angiogenic polymer conjugate (APC) for treatment of solid tumors comprising a chemical moiety targeting cell-surface proteins of endothelial cells at an angiogenic site. The chemical moiety taught in the application may be a ligand such as RGD4C (SEQ ID NO:5) or RGDfK (SEQ ID NO:4) for a cell-surface receptor, such as, for example, an integrin. The polymer conjugate taught by WO 2006/012355 may further comprise at least one side chain comprising a chelator capable of chelating a pharmaceutically acceptable radioactive label. The scintigraphic images and biodistribution of an exemplary such conjugate, HPMA copolymer-RGD4C-$^{99m}$Tc conjugate (SEQ ID NO: 6), indicated specific in vivo tumor targeting as well as prolonged retention of the conjugate at the tumor site. Treatment of SCID mice bearing DU145 human prostate carcinoma xenografts with another exemplary conjugate, HPMA copolymer-RGD4C comprising the beta particle emitter $^{90}$Y (SEQ ID NO:7), resulted in significant decrease of tumor volume as compared to the control (also reported by Mitra et al. in [*Nuclear Medicine and Biology* 2006; 33:43-52])

Wan et al. [2003 *Proc. Intl Symp. Control. Rel. Bioact. Mater.* Vol 30: 491-492] teach targeting endothelial cells using HPMA copolymer-doxorubicin-RGD conjugates (SEQ ID NO:8).

SUMMARY OF THE INVENTION

The present inventors have designed and successfully prepared and practiced conjugates comprised of a polymeric backbone having attached thereto an angiogenesis targeting moiety and a therapeutically active agent such as an anti-cancer agent or anti-angiogenesis agent. These conjugates were shown to exhibit a potent activity as agents for the treatment of medical conditions associated with angiogenesis such as cancer and cancer metastases.

According to an aspect of embodiments of the invention there is provided a conjugate comprising a polymeric backbone having attached thereto a therapeutically active agent and an angiogenesis targeting moiety, the angiogenesis targeting moiety comprising a least one Arg-Gly-Asp (RGD)-containing moiety (SEQ ID NO:1), and the therapeutically active agent being selected from the group consisting of paclitaxel and TNP-470.

According to some embodiments of the invention, the polymeric backbone is derived from a polyglutamic acid (PGA).

According to some embodiments of the invention, the polymeric backbone is derived from a polymer selected from the group consisting of dextran, a water soluble polyamino acid, a polyethylenglycol (PEG), a polyglutamic acid (PGA), a polylactic acid (PLA) a polylactic-co-glycolic acid (PLGA), a poly(D,L-lactide-co-glycolide) (PLA/PLGA), a poly(hydroxyalkylmethacrylamide), a polyglycerol, a polyamidoamine (PAMAM), and a polyethylenimine (PEI).

According to an aspect of embodiments of the invention there is provided a conjugate comprising a polymeric backbone having attached thereto a therapeutically active agent and an angiogenesis targeting moiety, the angiogenesis targeting moiety comprising a least one Arg-Gly-Asp (RGD)-containing moiety (SEQ ID NO:1), and the therapeutically active agent being selected from the group consisting of an anti-angiogenesis agent and an anti-cancer agent.

According to some embodiments of the invention, the RGD-containing moiety (SEQ ID NO:1) is an oligopeptide.

According to some embodiments of the invention, the oligopeptide is selected from the group consisting of a cyclic oligopeptide and a linear oligopeptide.

According to some embodiments of the invention, the angiogenesis targeting moiety comprises at least two RGD-containing moieties (SEQ ID NO:1), the moieties being the same or different.

According to some embodiments of the invention, the cyclic oligopeptide is c[Arg-Gly-Asp-Phe-Lys] (SEQ ID NO:9).

According to some embodiments of the invention, the polymeric backbone is derived from a polymer selected from the group consisting of dextran, a water soluble polyamino acid, a polyethylenglycol (PEG), a polyglutamic acid (PGA), a polylactic acid (PLA) a polylactic-co-glycolic acid (PLGA), a poly(D,L-lactide-co-glycolide) (PLA/PLGA), a poly(hydroxyalkylmethacrylamide), a polyglycerol, a polyamidoamine (PAMAM), and a polyethylenimine (PEI).

According to some embodiments of the invention, at least one of the therapeutically active agent and the targeting moiety is attached to the polymeric backbone via a linker.

According to some embodiments of the invention, the linker is a biodegradable linker.

According to some embodiments of the invention, the biodegradable linker is selected from the group consisting of a pH-sensitive linker and an enzymatically-cleavable linker.

According to some embodiments of the invention, the biodegradable linker is an enzymatically cleavable linker.

According to some embodiments of the invention, the enzymatically cleavable linker is cleaved by an enzyme which is overexpressed in tumor tissues.

According to some embodiments of the invention, the linker comprises a -[Gly-Phe-Leu-Gly]- moiety (SEQ ID NO: 10).

According to some embodiments of the invention, the linker comprises -[Gly-Pro-Leu-Gly-Ile-Ala-Gly-Gln]- (SEQ ID NO: 11).

According to some embodiments of the invention, at least one of the therapeutically active agent and the angiogenesis targeting moiety is attached to the polymeric backbone and/or to the linker via a spacer.

According to some embodiments of the invention, the anti-angiogenesis agent is Paclitaxel and the angiogenesis targeting moiety comprises a c[Arg-Gly-Asp-Phe-Lys] moiety (SEQ ID NO:9).

According to some embodiments of the invention, the anti-angiogenesis agent is Paclitaxel and the angiogenesis targeting moiety comprises two c[Arg-Gly-Asp-Phe-Lys] moieties (SEQ ID NO:9).

According to some embodiments of the invention, the conjugate has the structure:

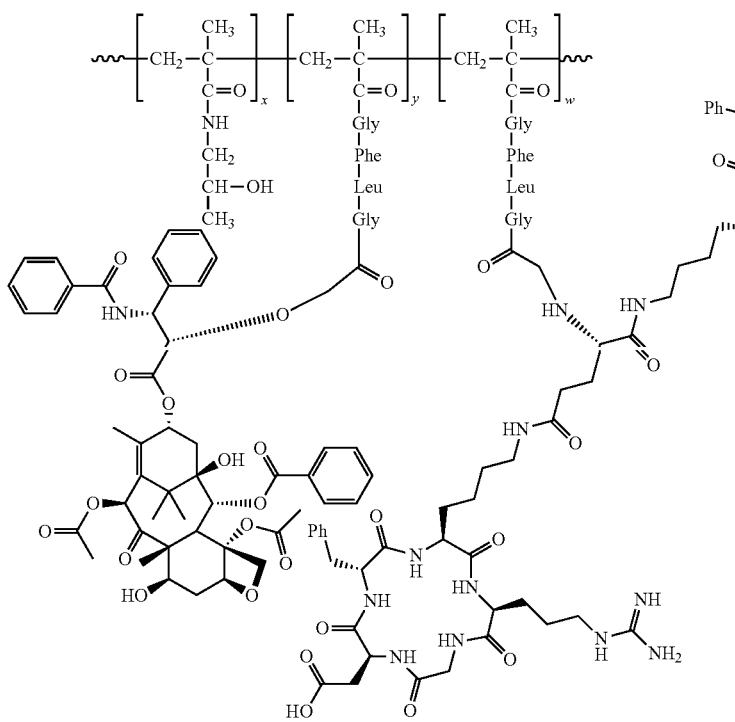

wherein:

x is an integer having a value such that x/(x+y+w) multiplied by 100 is in the range of from 0.01 to 99.9;

y is an integer having a value such that y/(x+y+w) multiplied by 100 is in the range of from 0.01 to 99.9; and w is an integer having a value such that w/(x+y+w) multiplied by 100 is in the range of from 0.01 to 99.9.

According to some embodiments of the invention, the conjugate has the structure:

wherein:

x is an integer having a value such that x/(x+y+w) multiplied by 100 is in the range of from 70 to 99.9;

y is an integer having a value such that y/(x+y+w) multiplied by 100 is in the range of from 0.01 to 15; and w is an integer having a value such that w/(x+y+w) multiplied by 100 is in the range of from 0.01 to 15.

According to some embodiments of the invention, the conjugate has a hydrodynamic diameter in the range of from 10 nm to 100 nm.

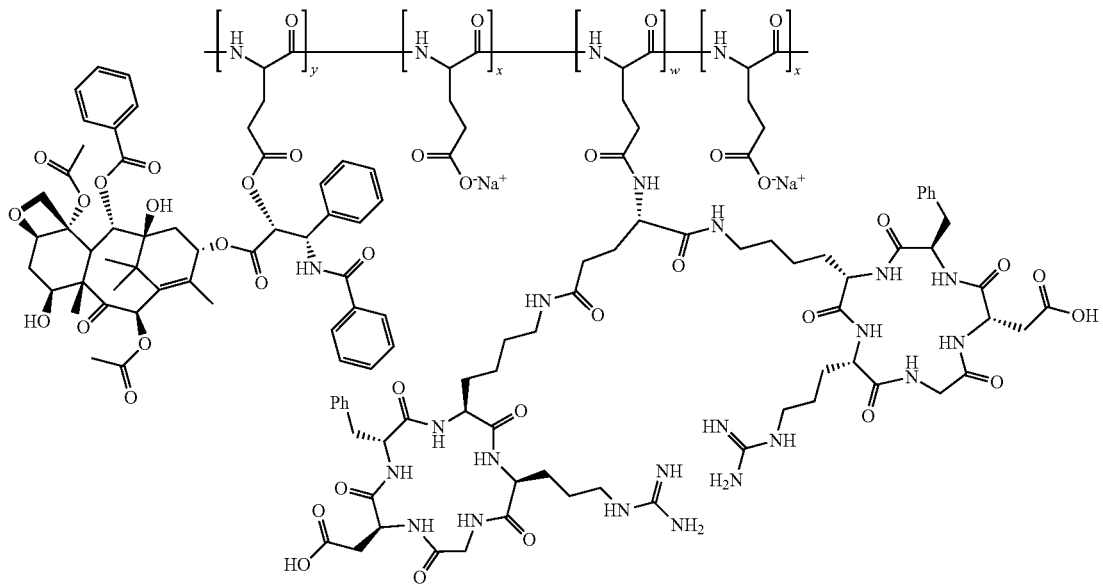

According to some embodiments of the invention, a load of the therapeutically active agent in the polymer is greater than 1 mol %.

According to some embodiments of the invention, a load of the angiogenesis targeting moiety in the polymer is greater than 1 mol %.

According to some embodiments of the invention, the conjugate further comprising a labeling agent attached thereto.

According to an aspect of embodiments of the invention there is provided a pharmaceutical composition comprising, as an active ingredient, the conjugate as described herein and a pharmaceutically acceptable carrier.

According to some embodiments of the invention, the composition is being packaged in a packaging material and identified in print, in or on the packaging material, for use in the treatment of a medical condition associated with angiogenesis.

According to some embodiments of the invention, the conjugate comprises a labeling agent, the composition being packaged in a packaging material and identified in print, in or on the packaging material, for use in monitoring a medical condition associated with angiogenesis.

According to some embodiments of the invention, the condition is selected from a group consisting of atherosclerosis, cancer, hypertension, rheumatoid arthritis, diabetes and diabetes related complications.

According to an aspect of embodiments of the invention there is provided a method of treating a medical condition associated with angiogenesis in a subject in need thereof, the method comprising administering to the subject a therapeutically effective amount of the conjugate as described herein.

According to an aspect of embodiments of the invention there is provided a method of monitoring the level of angiogenesis within a body of a patient, the method comprising:
administering to the patient the conjugate having a labeling agent as described herein attached thereto; and employing an imaging technique for monitoring a distribution of the conjugate within the body or within a portion thereof.

According to some embodiments, the condition is selected from the group consisting of atherosclerosis, cancer, hypertension, rheumatoid arthritis, diabetes and diabetes related complications.

According to an aspect of embodiments of the invention there is provided a use of the conjugate as described herein as a medicament.

According to an aspect of embodiments of the invention there is provided a use of the conjugate as described herein in the manufacture of a medicament for treating a medical condition associated with angiogenesis.

According to an aspect of embodiments of the invention there is provided a use of the conjugate having a labeling agent as described herein as a diagnostic agent.

According to an aspect of embodiments of the invention there is provided a use conjugate having a labeling agent as described herein in the manufacture of a diagnostic agent for monitoring a medical condition associated with angiogenesis.

According to an aspect of embodiments of the invention there is provided a process of synthesizing the conjugate as described herein, the process comprising:
(a) co-polymerizing a plurality of monomeric units of the polymer, at least one of the monomeric units terminating by a first reactive group, and at least one of the monomeric units terminating by a second reactive group, to thereby obtain a co-polymer that comprises a plurality of backbone units, at least one backbone unit having the first reactive group and at least one backbone unit having the second reactive group, the first reactive group being capable of reacting with the angiogenesis targeting moiety and the second reactive being capable of reacting with the therapeutically active agent;
(b) reacting the co-polymer with the angiogenesis targeting moiety or a derivative thereof, via the first reactive group, to thereby obtain a copolymer having the angiogenesis targeting moiety attached to a polymeric backbone thereof; and
(c) further reacting the co-polymer with the therapeutically active agent or a derivative thereof, via the second reactive group, to thereby obtain the co-polymer having the therapeutically active agent attached to a polymeric backbone thereof, thereby obtaining the conjugate of claim 1.

According to some embodiments of the invention, (b) is performed subsequent to, concomitant with or prior to (c).

According to some embodiments of the invention, at least one of the monomer units terminating by the first or the second reactive group further comprises a linker linking the reactive group to the monomeric unit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
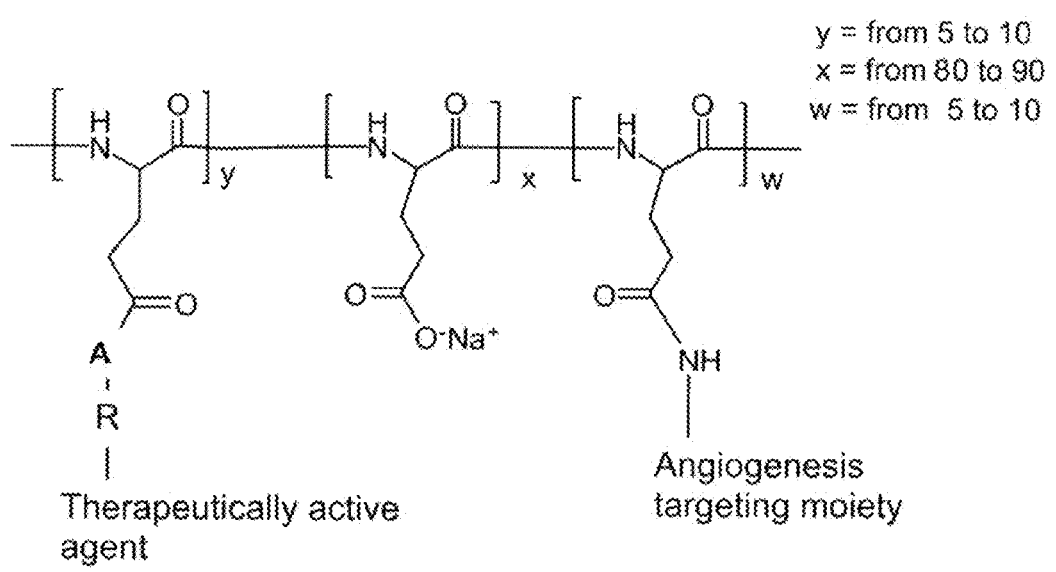

FIG. 1 presents the general formula of a polyglutamic acid based conjugate, according to some embodiments of the invention, wherein a polyglutamic polymeric backbone is conjugated to a therapeutically active agent through a degradable linker and to an angiogenesis targeting moiety. A is a —O— or —N— bond and R is a peptidic linker which can be cleaved by enzymes such as Cathepsin B or MMP (i.e. Phe-Lys; SEQ ID NO: 12, Phe-Val-Gly-Leu-Ile-Gly; SEQ ID NO:13) or a pH labile linker (i.e. ester or acetal). The average MW of the PGA polymer from which the polymeric backbone is derived is 152 grams/mole.

Figure 2A:
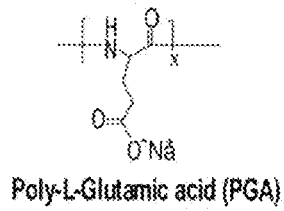
Figure 2B:
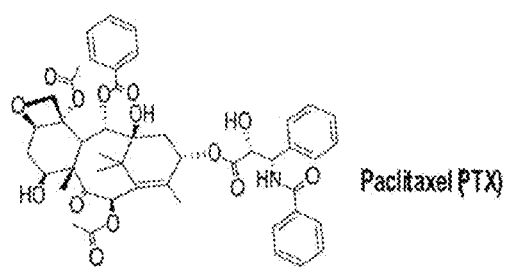
Figure 2C:
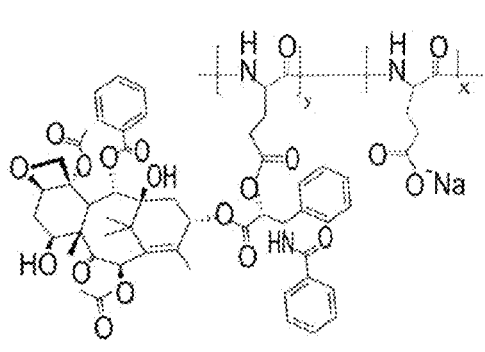
Figure 2D:
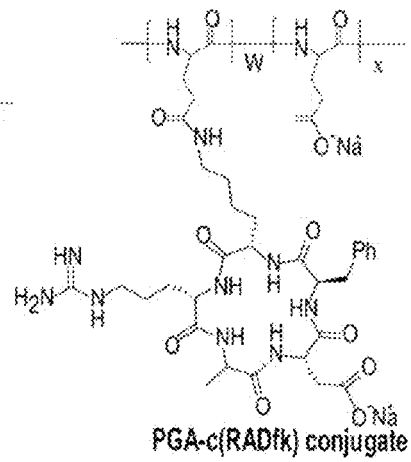
Figure 2E:
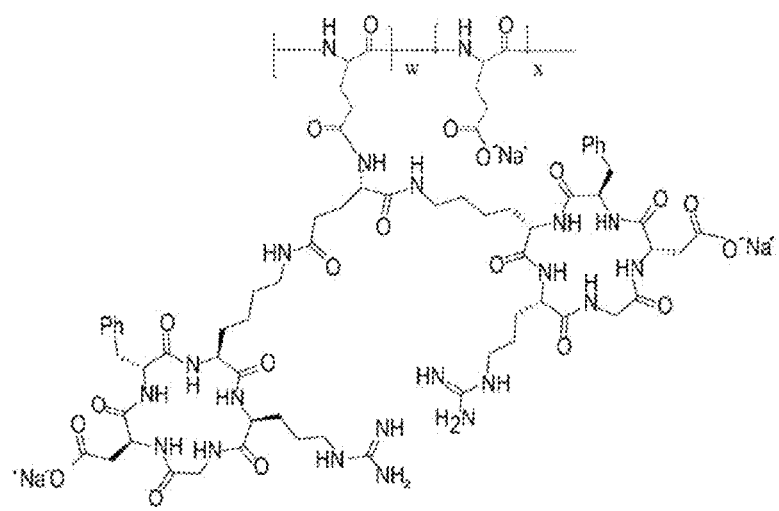
Figure 2F:
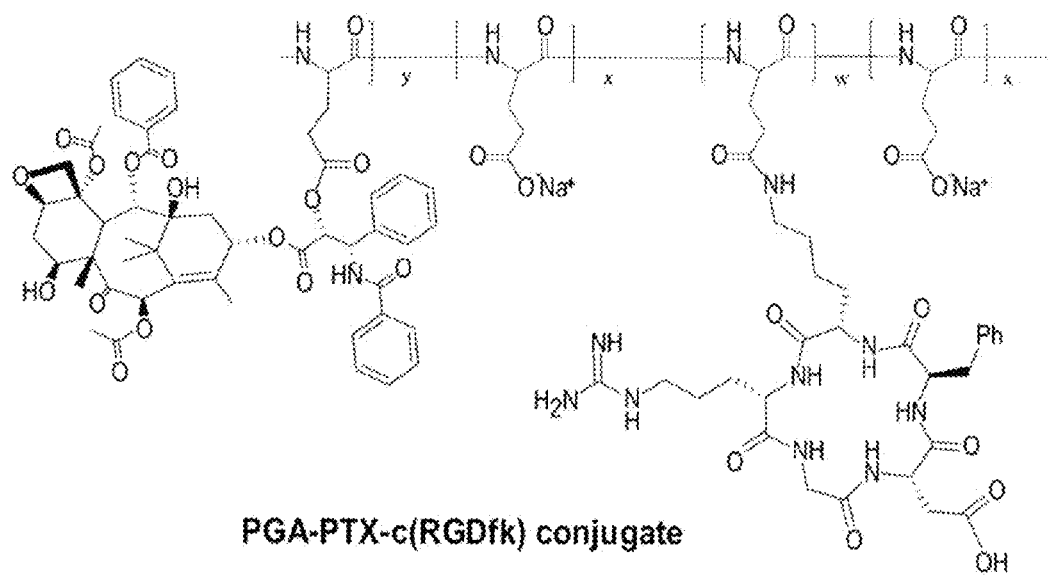
Figure 2G:
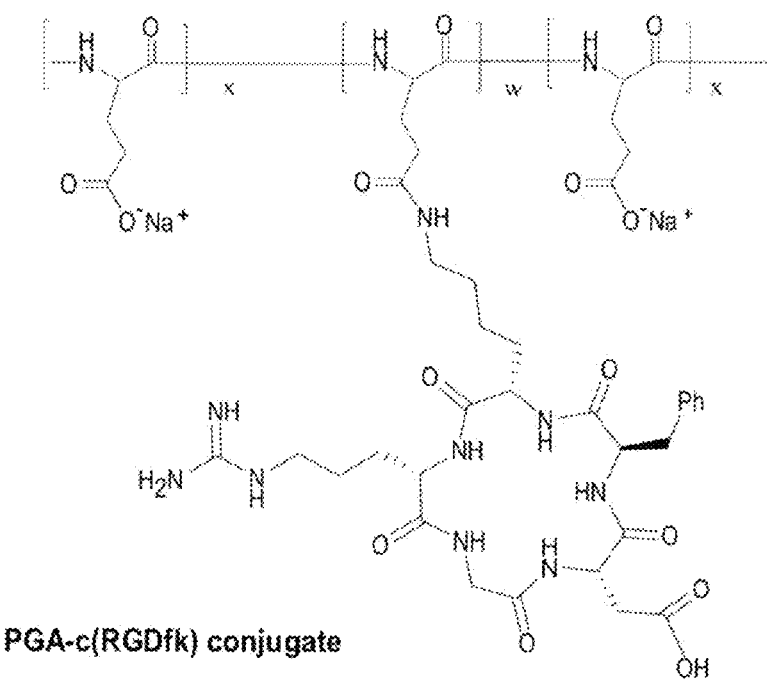

FIGS. 2A-G presents the 2-D chemical structure of Polyglutamic acid (PGA; FIG. 2A) Paclitaxel (PTX; FIG. 2B), a PGA-PTX conjugate, having a molecular weight average of 191.7 grams/mol (FIG. 2C), a PGA-c(RADfk) conjugate (SEQ ID NO: 14) having an average molecular weight of 181.59 grams/mol (FIG. 3D); a PGA-E-c(RGDfk)$_2$ conjugate (SEQ ID NO: 15; FIG. 2E); a PGA-PTX-c(RGDfk) conjugate (SEQ ID NO: 16; FIG. 2F) and a PGA-c(RGDfk) conjugate (SEQ ID NO: 17; FIG. 2G).

Figure 3A:
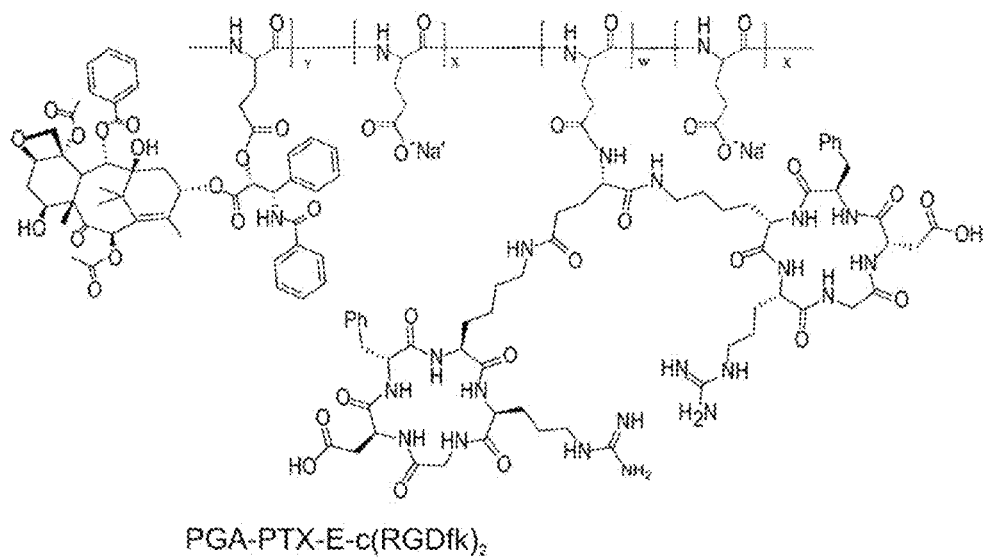
Figure 3B:
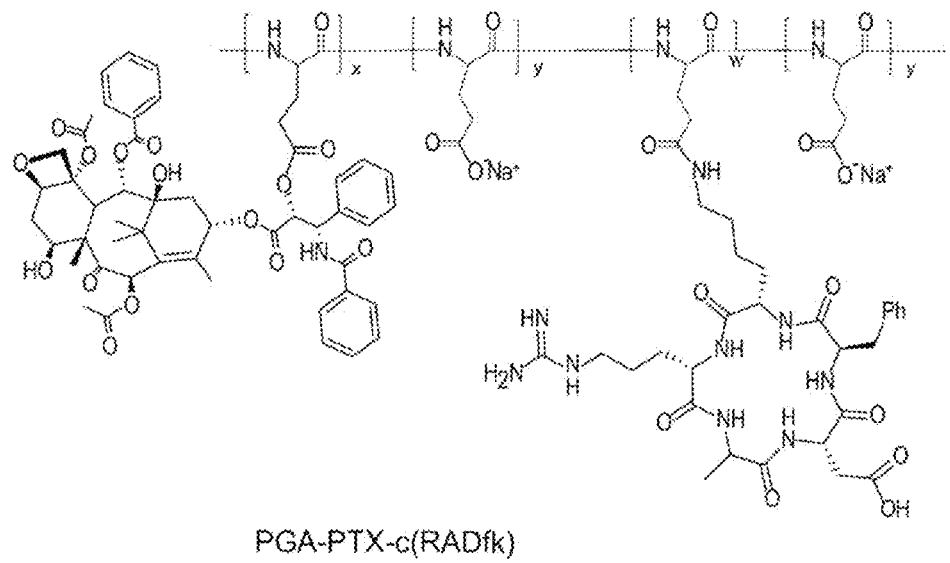

FIGS. 3A-B present the 2-D chemical structure of the PGA-PTX-E-c(RGDfk)$_2$ conjugate (SEQ ID NO: 18) according to some embodiments of the invention, in which the average molecular weight of the PGA polymer from which the polymeric backbone is derived is 256.53 grams/mol, (FIG. 3A) and of a PGA-PTX-c(RADfk) conjugate (SEQ ID NO: 19) according to some embodiments of the invention in which the molecular weight of the PGA polymer from which the polymeric backbone is derived is 221.54 grams/mol (FIG. 3B).

Figure 4A:
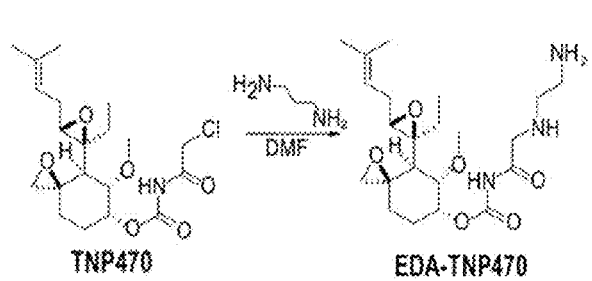
Figure 4B:
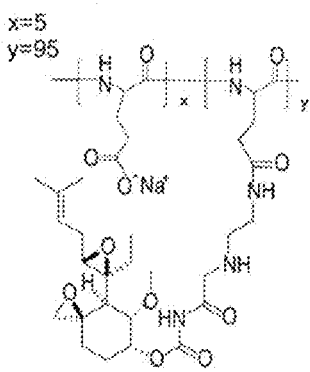
Figure 4C:
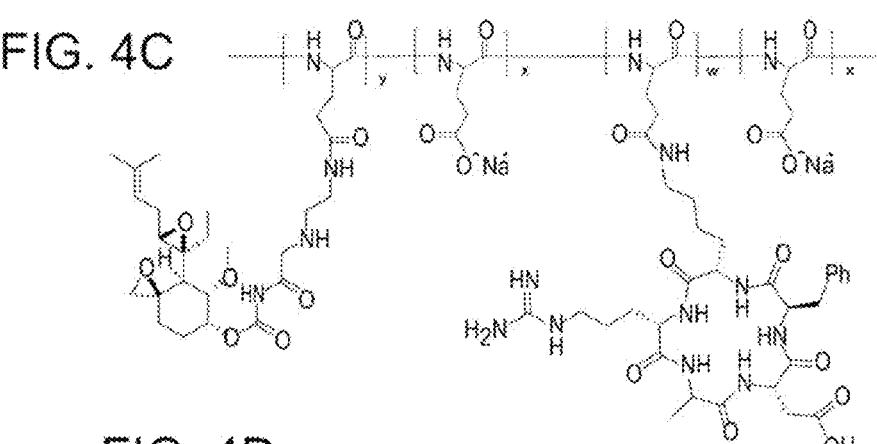
Figure 4D:
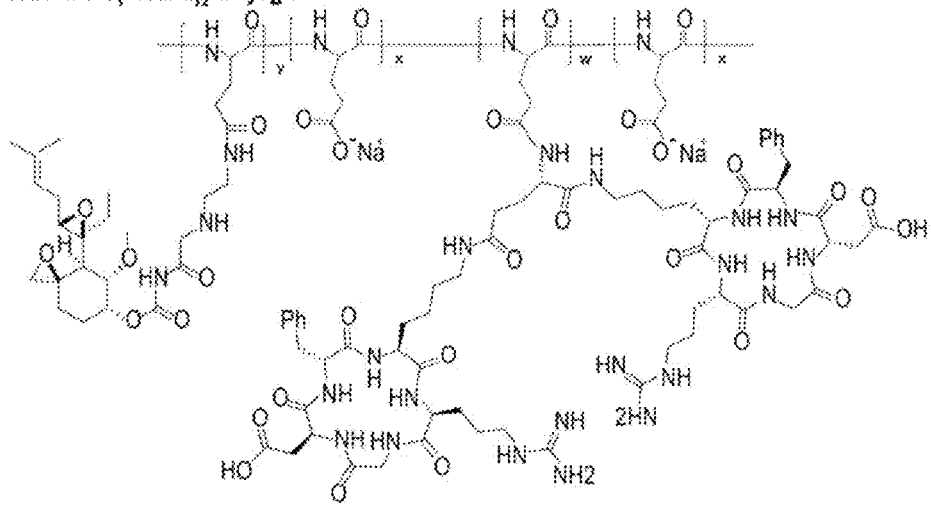

FIGS. 4A-D present a scheme illustrating an optional synthetic pathway for generating the anti-angiogenesis agent TNP-470 having attached thereto a $NH_2(CH_2)_2NH_2$ moiety (FIG. 4A), as well as the 2-D chemical structures of a PGA-(TNP-470) conjugate (FIG. 4B), PGA-(TNP-470)-c(RADfk) conjugate (SEQ ID NO: 20; FIG. 4C) and PGA-(TNP-470)-E-[c(RGDfk)$_2$] conjugate (SEQ ID NO: 21), according to some embodiments of the present invention (FIG. 4D).

Figure 5:
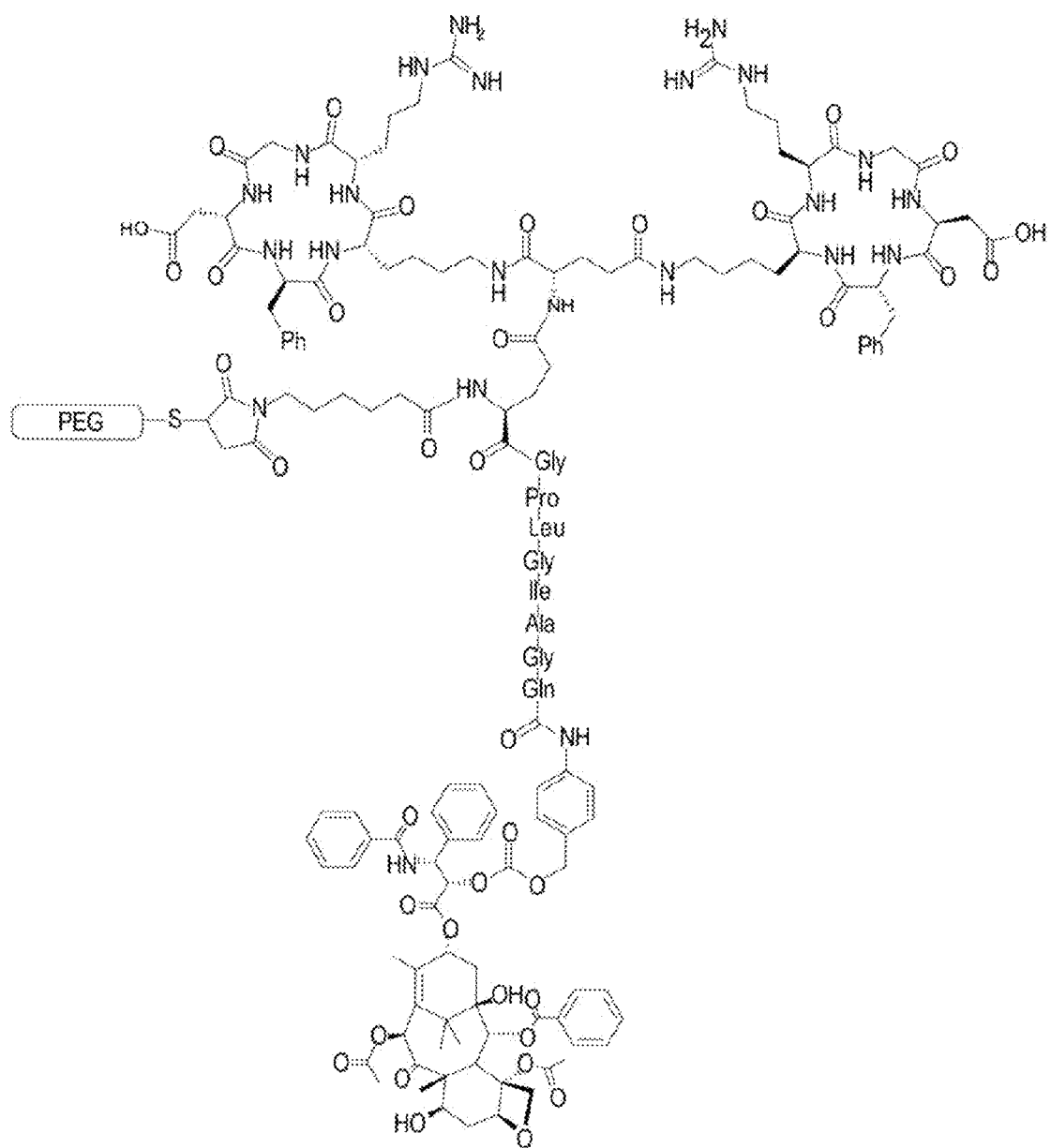

FIG. 5 presents the 2-D chemical structure of a polyethylenglycol polymer having conjugated thereto PTX and c(RGDfk)$_2$ [PEG-PTX-E-[c(RGDfk)$_2$, according to some embodiments of the present invention (SEQ ID NO: 22).

Figure 6:
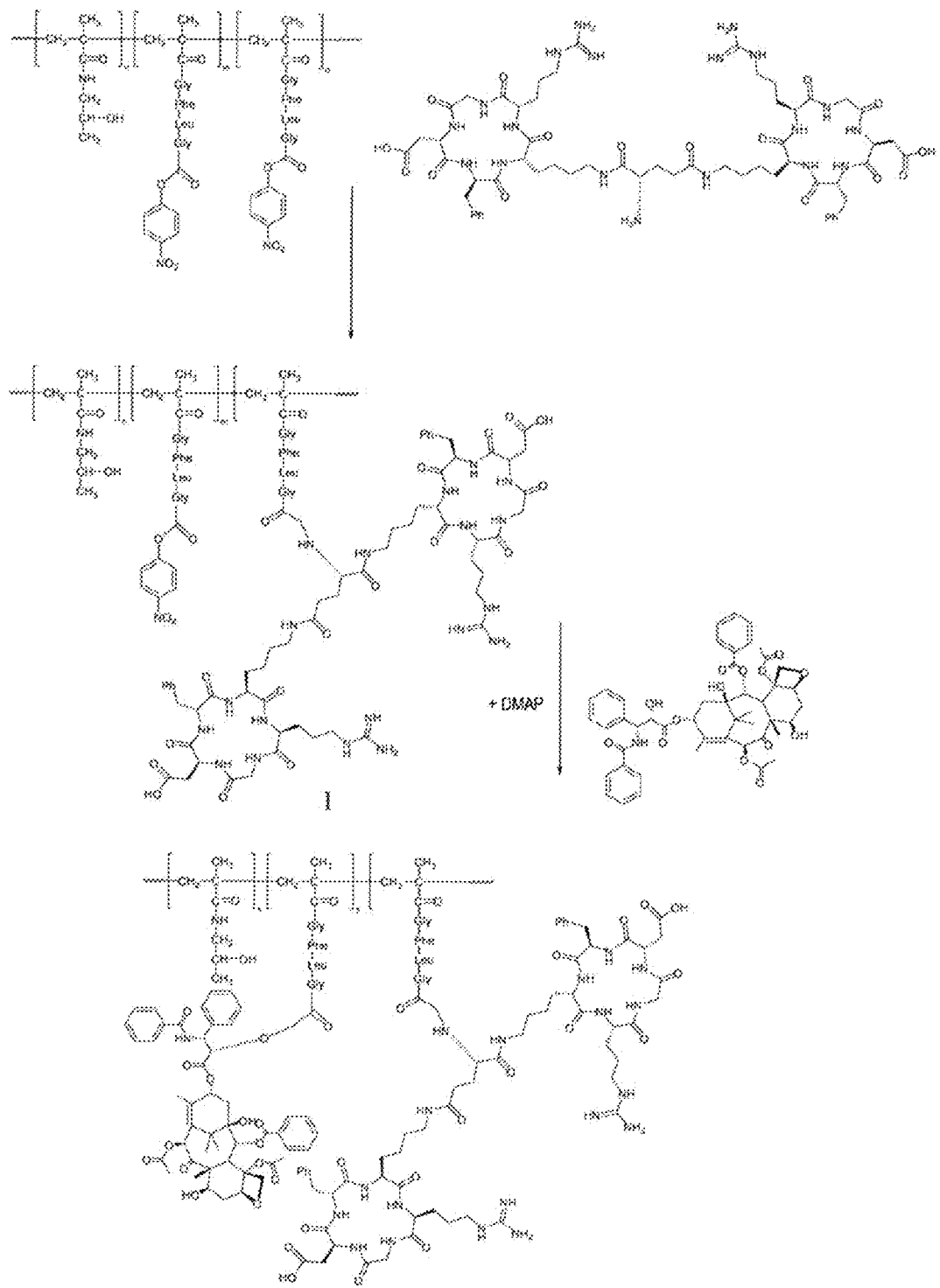

FIG. 6 presents a scheme illustrating the synthesis of an HPMA copolymer-E-[c(RGDfk)$_2$]-Paclitaxel conjugate (SEQ ID NO:23) according to some embodiments of the present invention.

Figure 7:
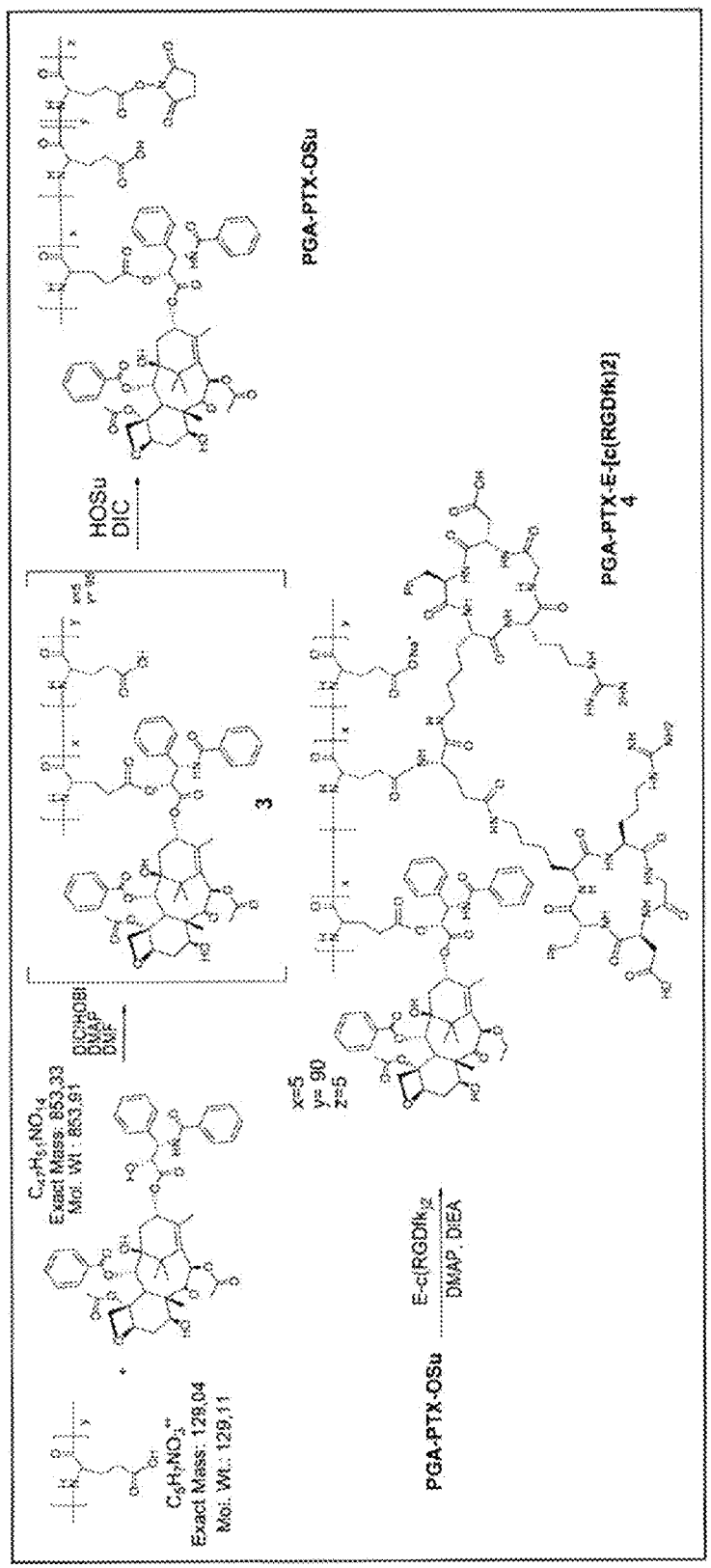

FIG. 7 presents a scheme illustrating the synthesis of a polyglutamic acid based polymer conjugate [PGA-PTX-E-c(RGDfk)$_2$] (SEQ ID NO: 18), a conjugate according to some embodiments of the present invention.

Figure 8:
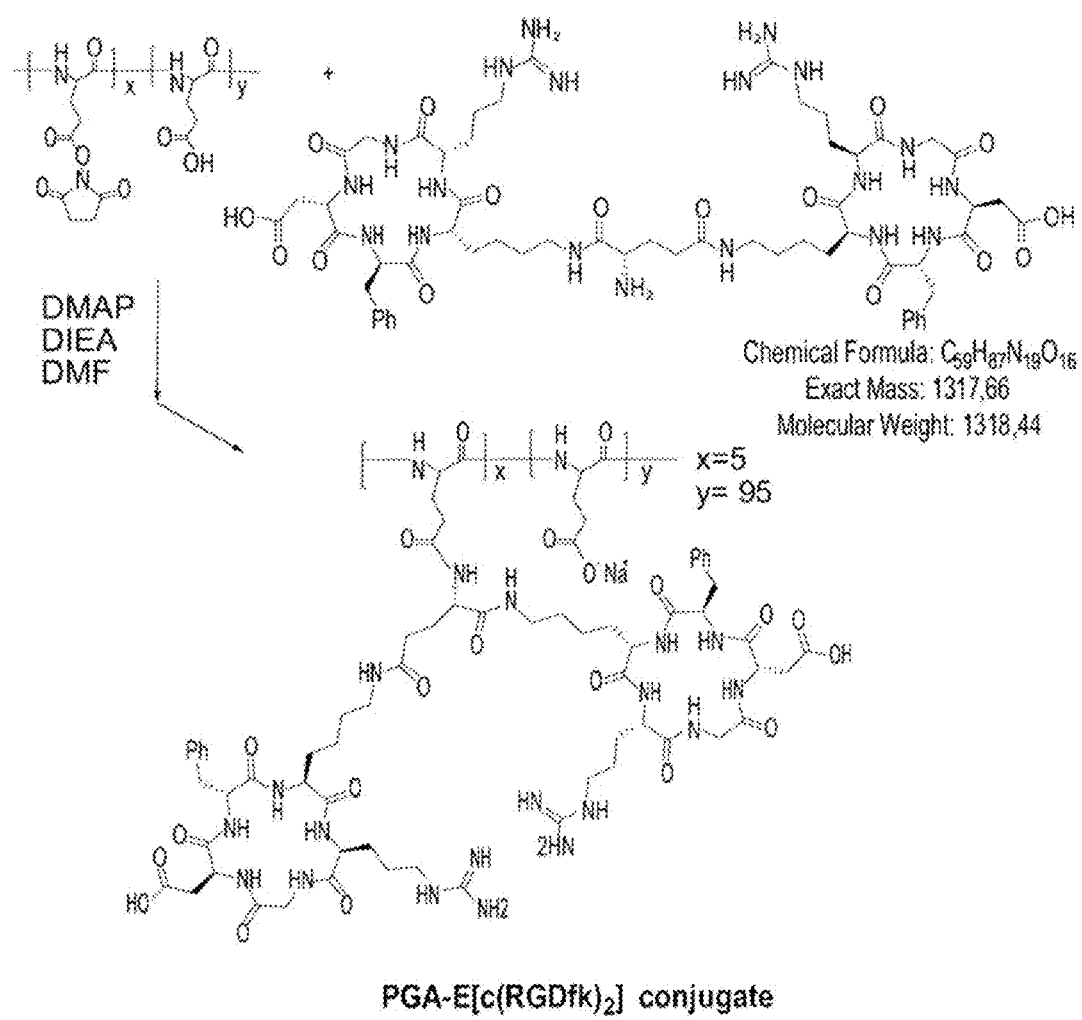

FIG. 8 presents a scheme illustrating the synthesis of a polyglutamic acid polymer and c(RGDfk)$_2$ conjugate [PGA-E-c(RGDfk)$_2$] (SEQ ID NO: 15).

Figure 9A:
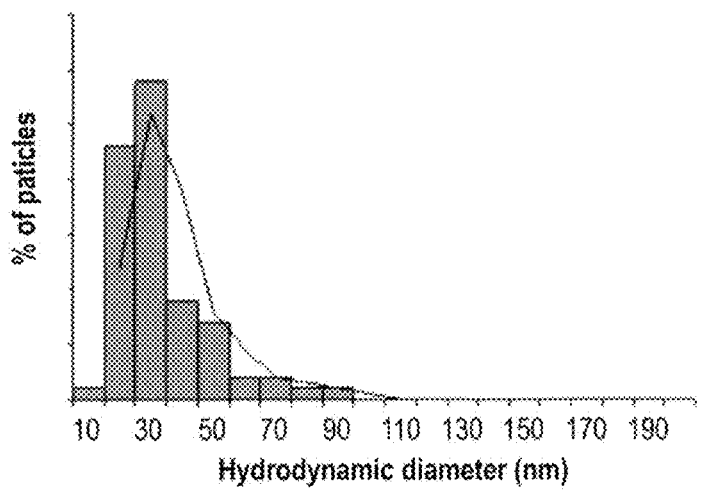
Figure 9B:
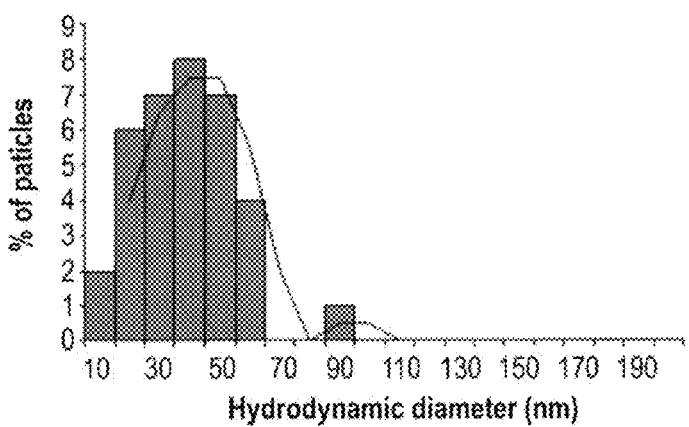
Figure 9C:
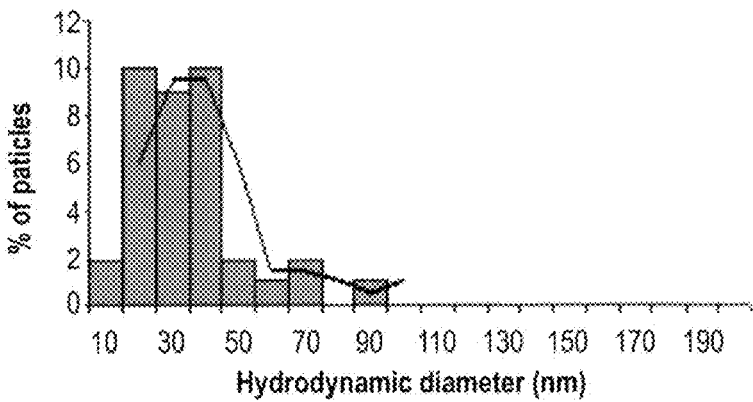

FIGS. 9A-C present bar diagrams of the hydrodynamic diameters of two synthesized conjugates [PGA-PTX-E-c(RGDfk)$_2$] (SEQ ID NO: 18; FIGS. 9A and 9B) and the synthesized conjugate [PGA-PTX-c(RGDfk)] (SEQ ID NO:16 FIG. 9C), all being conjugates according to some embodiments of the present invention. The hydrodynamic diameter of the conjugates was assessed using laser light scattering microscopy with the Nanoparticle Tracking Analysis (NTA) technology. The mean hydrodynamic diameter of the conjugate [PGA-PTX-E-c(RGDfk)$_2$] (SEQ ID NO: 18) with PTX loading of 5.5 mol % and -E-c(RGDfk)$_2$ loading of 3.9 mol % is shown in FIG. 9A. The mean hydrodynamic diameter of the conjugate [PGA-PTX-E-c(RGDfk)$_2$] (SEQ ID NO: 18) with PTX loading of 2.6 mol % and -E-c(RGDfk)$_2$ loading of 5 mol % is shown in FIG. 9B. The mean hydrodynamic diameter of the conjugate [PGA-PTX-c(RGDfk)] (SEQ ID NO:16) with PTX loading of 2.1 mol % and with -c(RGDfk) loading of 5 mol % is shown in FIG. 9C.

Figure 10A:
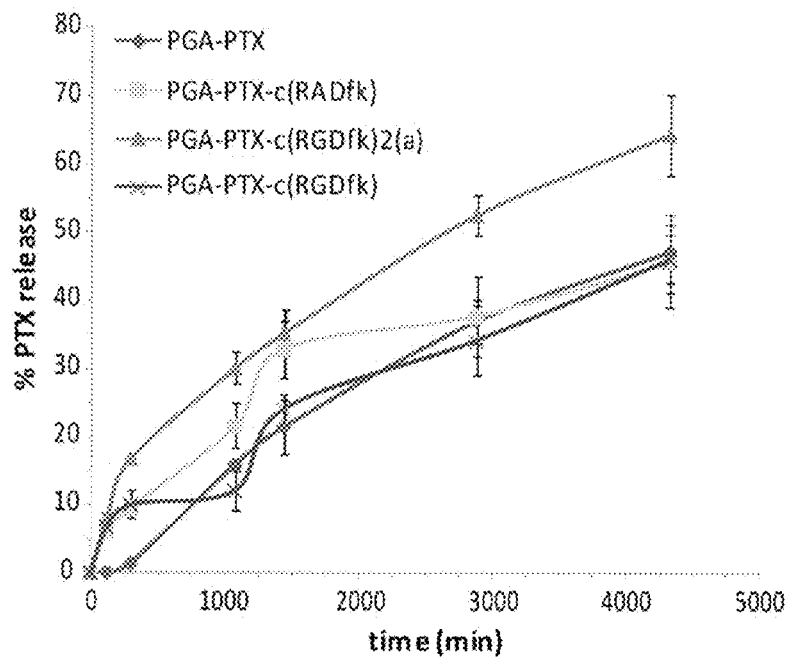
Figure 10B:
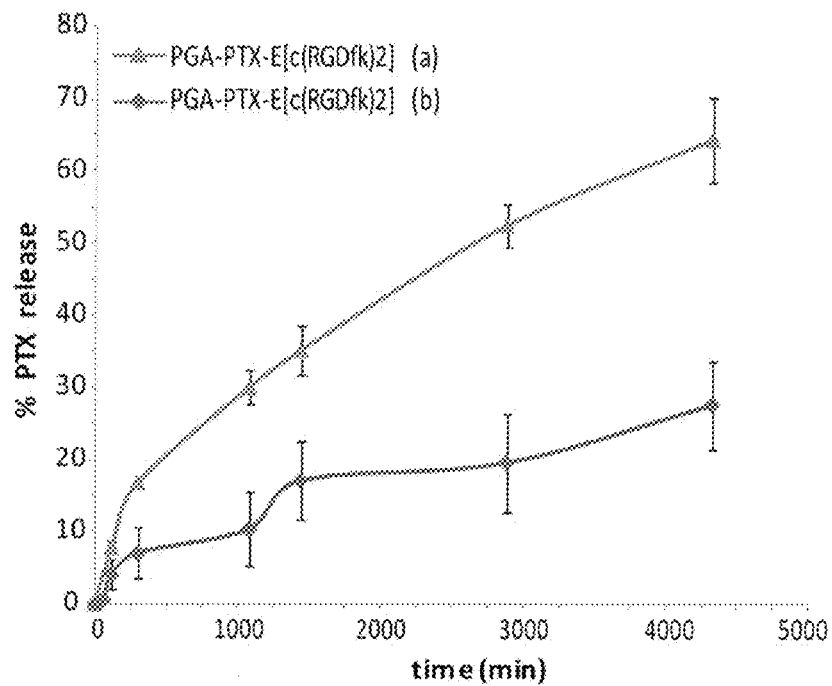

FIGS. 10A-B present paclitaxel release profile kinetics from various PGA-based conjugates in the presence of Cathepsin B or hydrolytic conditions. Presented in FIG. 10A are comparative plots of the percentage of Paclitaxel release from a conjugate of PGA and PTX (PGA-PTX; filled diamonds), a PGA-PTX-c(RADfk) conjugate (SEQ ID NO: 19; filled squares), a PGA-PTX-E-[c(RGDfk)$_2$] conjugate (SEQ ID NO:18; filled triangles), and a PGA-PTX-[c(RGDfk)] conjugate (SEQ ID NO:16; crosses), which were incubated with cathepsin B, as a function of time. Presented in FIG. 10B are comparative plots of the percentage of Paclitaxel release from a PGA-PTX-E-[c(RGDfk)$_2$] conjugate (SEQ ID NO:18; having a loading of 2.6% mol PTX and 5 mol % E-[c(RGDfk)$_2$], (filled triangles), and a PGA-PTX-E-[c(RGDfk)$_2$] conjugate (SEQ ID NO:18) having a loading of 5.5% mol PTX and 3.9 mol % E-[c(RGDfk)$_2$], (filled diamonds), which were incubated with cathepsin B, as a function of time.

Figure 11A:
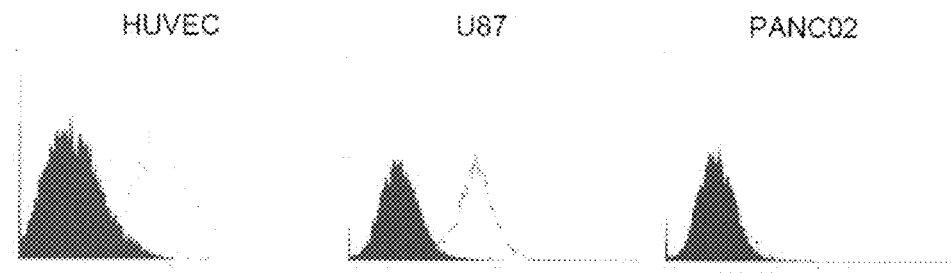
Figure 11B:
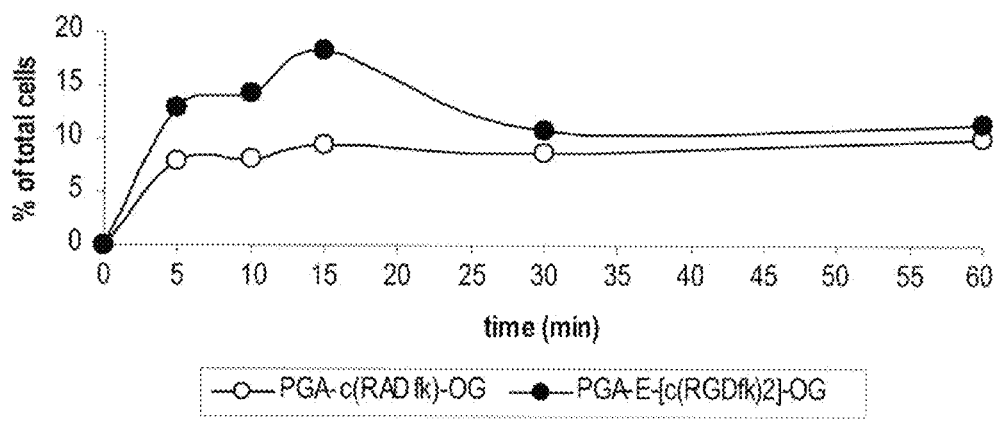
Figure 11C:
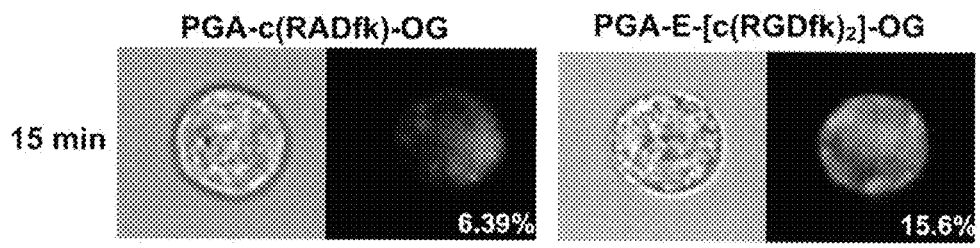

FIGS. 11A-C present data showing the cell expression of $\alpha v \beta_3$ integrin and its interaction with conjugates according to embodiments of the invention. HUVEC, U87 human glioblastoma cells and PANC02 murine pancreatic tumor cells were subjected to immunostaining with anti-$\alpha v \beta_3$ followed by a fluorescently labeled secondary antibody and scanned for $\alpha v \beta_3$ presence using FACS (see FIG. 11A). Serving as control were cells not incubated with any antibody. Analysis of the results showed that only HUVEC, and U87 cells but not PANC02 cells expressed the $\alpha v \beta_3$ integrin. The florescence probe Oregon Green-cadaverine (OG), was conjugated to PGA-c(RADfk) (SEQ ID NO: 14) and to PGA-E-[c(RGDfk)$_2$] (SEQ ID NO: 15) to result in a (PGA-c(RADfk)-OG (SEQ ID NO: 24) or PGA-E-[c(RGDfk)$_2$]-OG (SEQ ID NO:25)) and their adhesion to $\alpha v \beta_3$ was assessed by incubation with human umbilical vein endothelial cells (HUVEC) followed by determination of the change in fluorescence using the ImageStream 100 imaging flow cytometer (Merkel Technologies Ltd.) (see, FIG. 11B). FIG. 11C presents images of the cells following 15 minutes of incubation with either PGA-c(RADfk)-OG (SEQ ID NO: 24; right picture) or PGA-E-[c(RGDfk)$_2$]-OG (SEQ ID NO:25; left picture) showing the higher uptake of conjugate containing the [c(RGDfk)$_2$] moiety (SEQ ID NO: 26) by the cells as compared to the inactive, RAD (SEQ ID NO: 27) containing, conjugate.

Figure 12A:
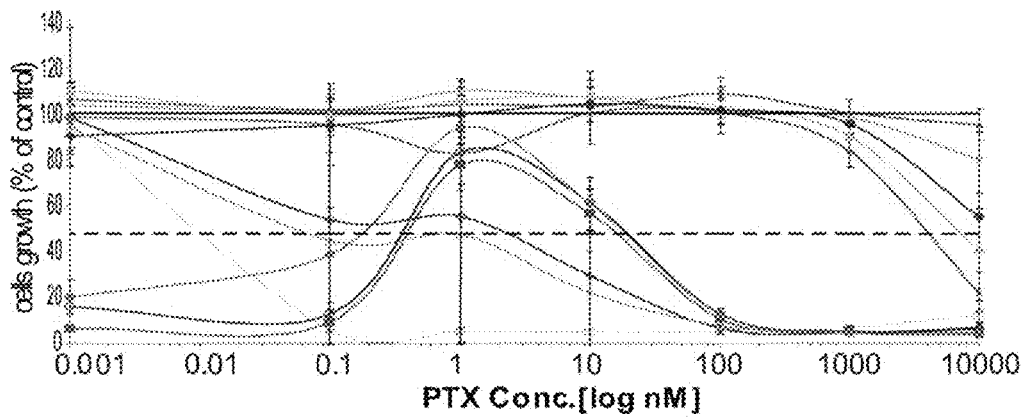
Figure 12B:
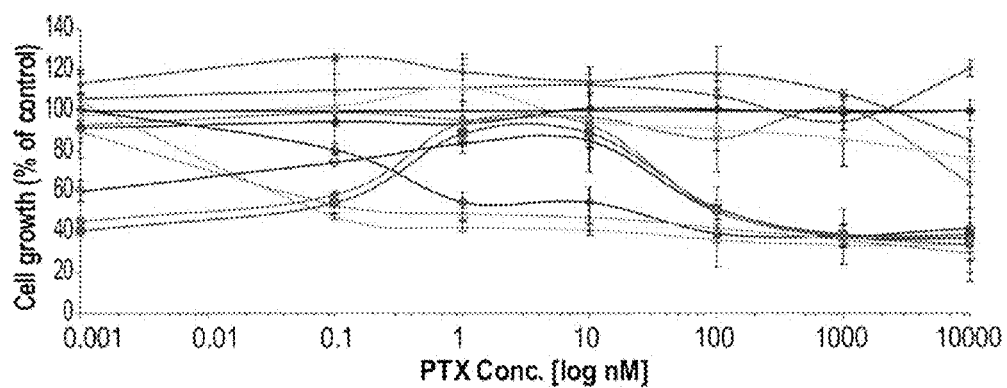
Figure 12C:
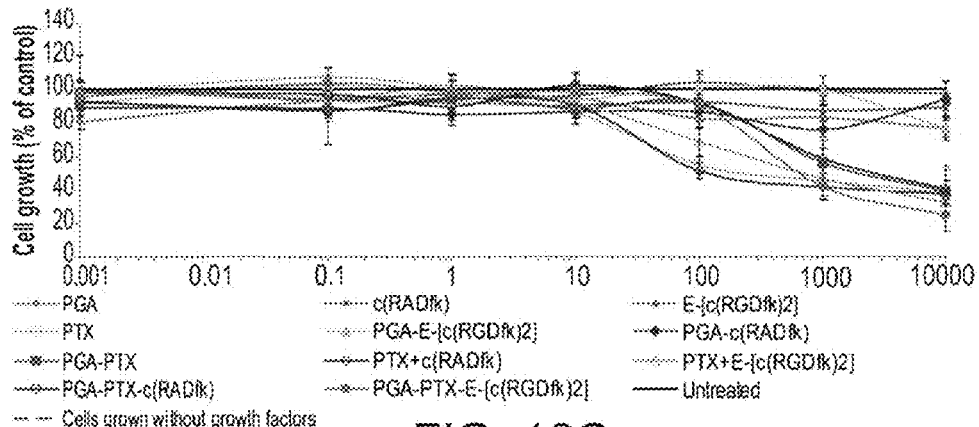

FIGS. 12A-C present comparative plots demonstrating that Paclitaxel retains its anti-angiogenic effect on the proliferation of HUVEC (FIG. 12A), U87 human glioblastoma cells (FIG. 12B) and PANC02 murine pancreatic tumor cells (FIG. 12C) when conjugates to the PGA-c(RGDfk)$_2$ polymer (SEQ ID NO:15), according to some embodiments of the invention. Results are presented as percents of cell growth (out of the control group) as a function of Paclitaxel concentration, for polyglutamic acid polymer alone (PGA, orange full squares); Paclitaxel alone (PTX, light blue empty squares), polyglutamic acid polymer conjugated to Paclitaxel (PGA-PTX; purple filled squares), Polyglutamic acid polymer conjugated to Paclitaxel and to the inactive cyclic peptide RAD (PGA-PTX-c(RADfk); SEQ ID NO: 19; dark blue empty circles); the free inactive cyclic peptide RAD (c(RADfk); SEQ ID NO: 28; pink filled diamonds); Polyglutamic acid polymer conjugated to a bis-cyclic RGD-containing peptide (PGA-E-[c(RGDfk)$_2$]; SEQ ID NO: 15; green filled triangles); free Paclitaxel+free inactive peptide RAD (PTX+c(RADfk) having SEQ ID NO: 28; blue empty diamonds); Polyglutamic acid polymer conjugated to Paclitaxel and to bis-cyclic RGD peptide, a conjugate according to some embodiments of the present invention (PGA-PTX-E-[c(RGDfk)$_2$]; SEQ ID NO: 18; green filled circles); free bis-cyclic RGD peptide (E-[c(RGDfk)$_2$]; SEQ ID NO: 2; red filled triangles); Polyglutamic acid polymer conjugated to inactive cyclic peptide RAD (PGA-c(RADfk); SEQ ID NO: 14; dark blue filled diamonds) and Paclitaxel conjugated to the bis-cyclic RGD-containing peptide (PTX-E-[c(RGDfk)$_2$]; SEQ ID NO: 29; green empty filled triangles); Solid and dashed lines represent the proliferation of cells in the presence (solid line) or absence (dashed line) of growth factors. Data represent mean±SD. The PGA-PTX-E-[c(RGDfk)$_2$] conjugate (SEQ ID NO: 18) used for the present experiments was the first conjugate synthesized (i.e. having a 5.5 mol % PTX and 3.9 mol % E-[c(RGDfk)$_2$] loading).

Figure 13A:
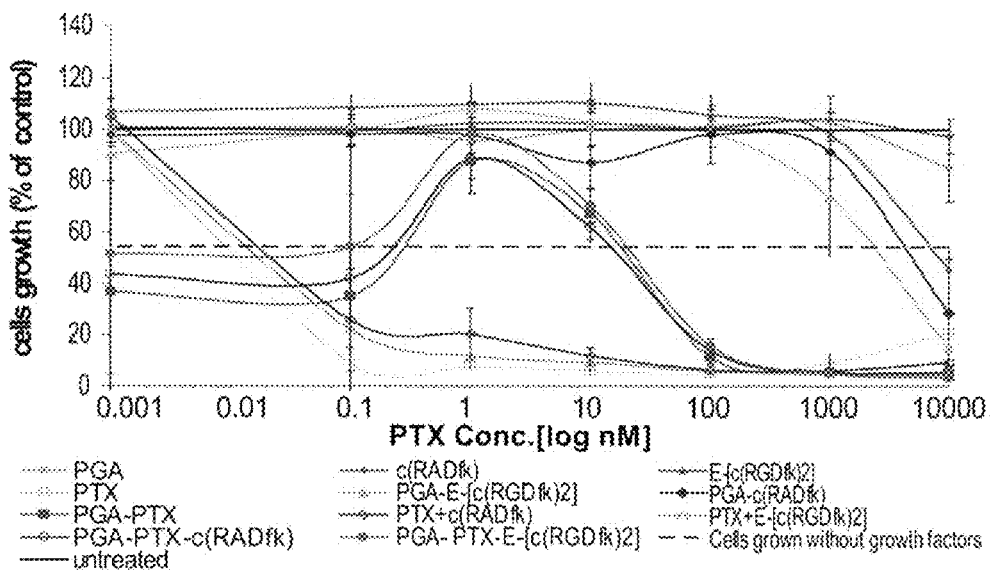
Figure 13B:
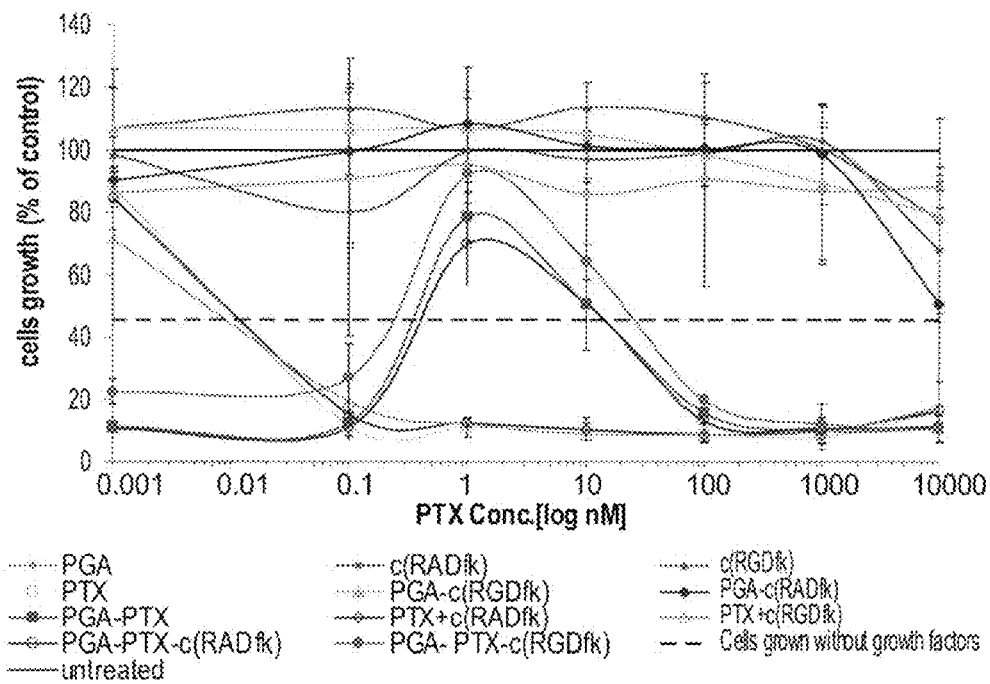

FIGS. 13A-B present comparative plots demonstrating the anti-proliferative effect on HUVEC of a PGA-PTX-E-[c(RGDfk)$_2$] conjugate (SEQ ID NO: 18) according to some embodiments of the invention, having a 5 mol % E-[c(RGDfk)$_2$] and 2.6 mol % PTX loading (FIG. 13A) and the anti-proliferative effect of the PGA-PTX-c(RGDfk) conjugate (SEQ ID NO:16; FIG. 13B). Results are presented as percents of cell growth (out of the control group) as a function of Paclitaxel concentration, for polyglutamic acid polymer alone (PGA, orange full squares); Paclitaxel alone (PTX, light blue empty squares), polyglutamic acid polymer conjugated to Paclitaxel (PGA-PTX; purple filled squares), polyglutamic acid polymer conjugated to Paclitaxel and to the inactive cyclic peptide c(RADfk) (PGA-PTX-c(RADfk);

SEQ ID NO: 19; dark blue empty circles); the inactive cyclic peptide c(RADfk) (c(RADfk); SEQ ID NO:28; pink filled diamonds); polyglutamic acid polymer conjugated to bis-cyclic RGD peptide (PGA-RGD; SEQ ID NO:17; green filled triangles) free Paclitaxel+free inactive peptide c(RADfk) (PTX+c(RADfk) having SEQ ID NO:28; blue empty diamonds); polyglutamic acid polymer conjugated to Paclitaxel and to bis-cyclic RGD peptide (in FIG. 13A) or to the monocyclic RGD (in FIG. 13B), (PGA-PTX-RGD; SEQ ID NO: 16; green filled circles); bis-cyclic RGD peptide alone (c(RGDfk)$_2$; SEQ ID NO: 26; red filled triangles); polyglutamic acid polymer conjugated to inactive cyclic peptide c(RADfk) (PGA-c(RADfk); SEQ ID NO: 14; dark blue filled diamonds) and Paclitaxel conjugated to the bis-cyclic RGD peptide (PTX-E-c(RGDfk)$_2$; SEQ ID NO: 29; green empty filled triangles); Solid and dashed lines represent the proliferation of cells in the presence (solid line) or absence (dashed line) of growth factors. Data represent mean±SD.

Figure 14:
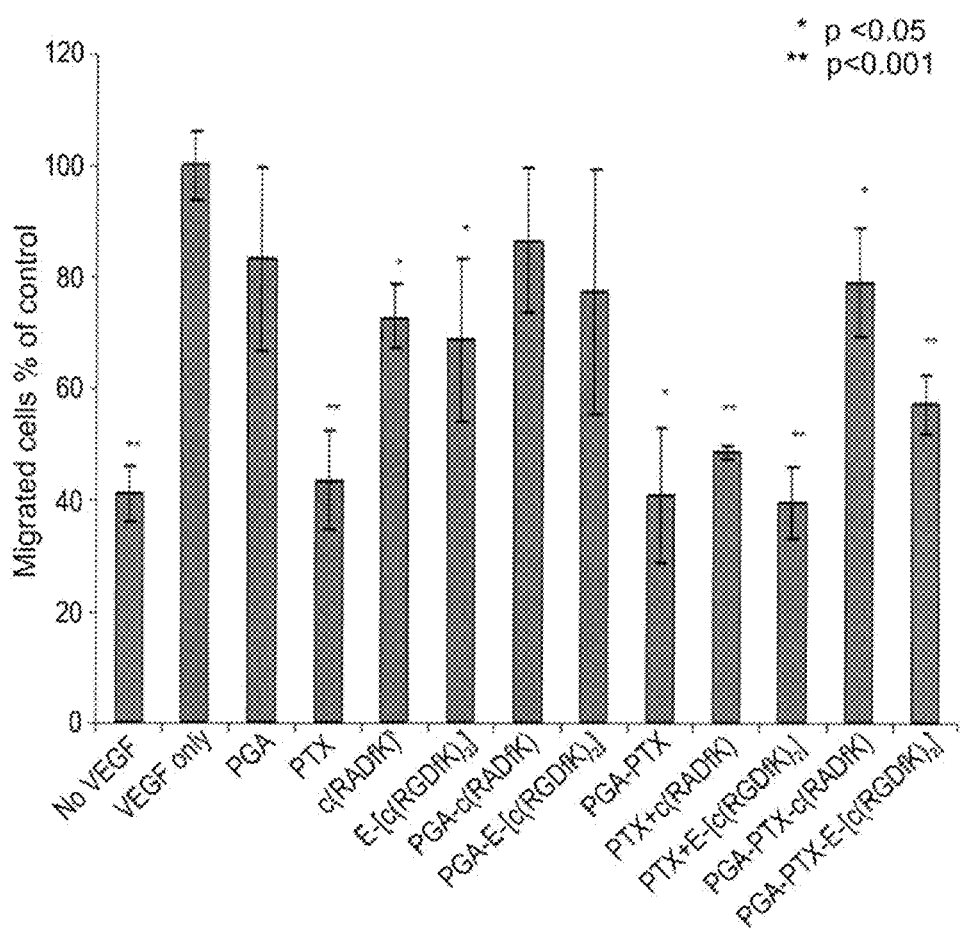

FIG. 14 present a bar graph showing the effect of PGA-PTX-E-[c(RGDfk)$_2$] (SEQ ID NO: 18) a conjugate according to some embodiments of the present invention, on the ability of HUVEC to migrate towards vascular endothelial growth factor (VEGF) chemoattractant and the ability to form capillary-like tube structures. Presented are the percentages of inhibition of HUVEC capillary-like tube structures by polyglutamic acid polymer alone (PGA); Paclitaxel alone (PTX); the inactive cyclic peptide c(RADfk) (c(RADfk); SEQ ID NO:28); bis-cyclic RGD peptide alone (E-[c(RGDfk)$_2$]; SEQ ID NO:2); polyglutamic acid polymer conjugated to Paclitaxel and to the inactive cyclic peptide c(RADfk) (PGA-PTX-c(RADfk)); polyglutamic acid polymer conjugated to bis-cyclic RGD peptide (PGA-E-[c(RGDfk)$_2$]; SEQ ID NO:15); polyglutamic acid conjugated to Paclitaxel (PGA-PTX); a combination of free Paclitaxel together with free inactive cyclic peptide c(RADfk) (PTX+c(RADfk) having SEQ ID NO:28); a combination of free Paclitaxel together with free the bis-cyclic RGD peptide (PTX+E-[c(RGDfk)$_2$] having SEQ ID NO:26); polyglutamic acid polymer conjugated to inactive cyclic peptide c(RADfk) (PGA-c(RADfk); SEQ ID NO:14) and polyglutamic acid polymer conjugated to Paclitaxel and to bis-cyclic RGD peptide, a conjugate according to some embodiments of the present invention (PGA-PTX-E-[c(RGDfk)$_2$]; SEQ ID NO:18) compared with non-treated cells (only with VEGF). Also shown is the percent of migration of cells not exposed to VEGF (No VEGF). Data represent mean±SD.

Figure 15:
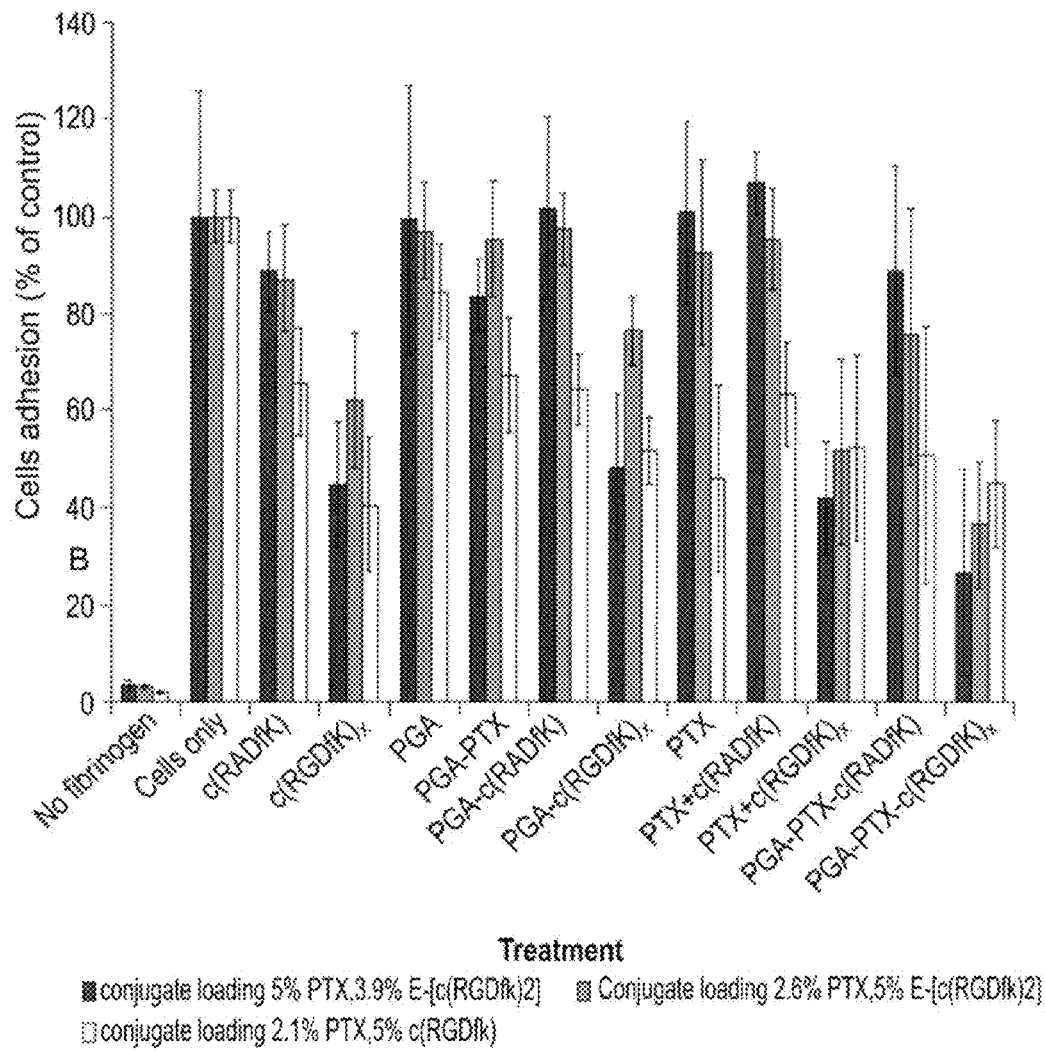

FIG. 15 presents a bar graph demonstrating that PGA-Paclitaxel-E-[c(RGDfk)$_2$] and PGA-Paclitaxel-[cRGDfk], (SEQ ID NOs: 18 and 16 respectively) both conjugates according to some embodiments of the invention, blocked the adhesion of HUVEC to fibrinogen coated plates. The percentage of HUVEC attachment after treatments was quantified and normalized to the percent of attachment of control cells (i.e., not incubated with any compound; marked as Cells only). The attached cells were fixed and dyed. Shown are three experiments performed: the first using the conjugate PGA-Paclitaxel-E-[c(RGDfk)$_2$] (SEQ ID NO: 18) having a 5.5 mol % PTX and 3.9 mol % of E-[c(RGDfk)$_2$ loading (dark gray); the second using the conjugate PGA-Paclitaxel-E-[c(RGDfk)$_2$] (SEQ ID NO:18) having a 2.6 mol % PTX and 5 mol % of E-[c(RGDfk)$_2$ loading (light gray); and a third using the conjugate PGA-Paclitaxel-c(RGDfk) (SEQ ID NO:16; having a 2.1 mol % PTX and 5 mol % of c(RGDfk) loading (white). The cells were incubated with the following tested compounds: the inactive cyclic peptide c(RADfk) (c(RADfk); SEQ ID NO:28); monocyclic RGD peptide alone (E-[c(RGDfk)]; SEQ ID NO:9); polyglutamic acid polymer alone (PGA); polyglutamic acid conjugated to Paclitaxel (PGA-PTX); polyglutamic acid polymer conjugated to inactive cyclic peptide c(RADfk) (PGA-c(RADfk); SEQ ID NO:14); polyglutamic acid polymer conjugated to bis-cyclic RGD peptide (PGA-E-[c(RGDfk)$_x$] wherein in the first two experiments x=2 and in the third experiment x=1; having ID SEQs of 15 and 17 when X=1 and 2 respectively); Paclitaxel alone (PTX); a combination of free Paclitaxel together with free inactive cyclic peptide c(RADfk) (PTX+c(RADfk) having SEQ ID NO:28); a combination of free Paclitaxel together with free the bis-cyclic RGD peptide (PTX+E-[c(RGDfk)$_x$] wherein in the first two experiments x=2 (SEQ ID NO:2) and in the third experiment x=1 (SEQ ID NO:9); polyglutamic acid polymer conjugated to Paclitaxel and to the inactive cyclic peptide c(RADfk) (PGA-PTX-c(RADfk); SEQ ID NO:19); and polyglutamic acid polymer conjugated to Paclitaxel and to bis-cyclic RGD peptide (PGA-PTX-[c(RGDfk)$_x$] wherein in the first two experiments x=2 and in the third experiment x=1 having ID SEQs of 18 and 16 when X=1 and 2 respectively). Whenever x=2, the c(RGDfk) moiety further includes a glutamate residue (-E-) to which the two cyclic RGDfk moieties are connected. Shown as control are cells not incubated with any compound (Cells only). Also shown are control cells seeded on plates without fibrinogen coating (No fibrinogen). The quantification was performed using Nikon TE2000E inverted microscope and NIH image software. *Treatment with c(RGDfk)$_2$ (SEQ ID NO:9; was at 20 μM concentration, while Paclitaxel was at 5 nM because Paclitaxel at a higher dose is toxic to the cells. Data represent mean±SD.

Figure 16A:
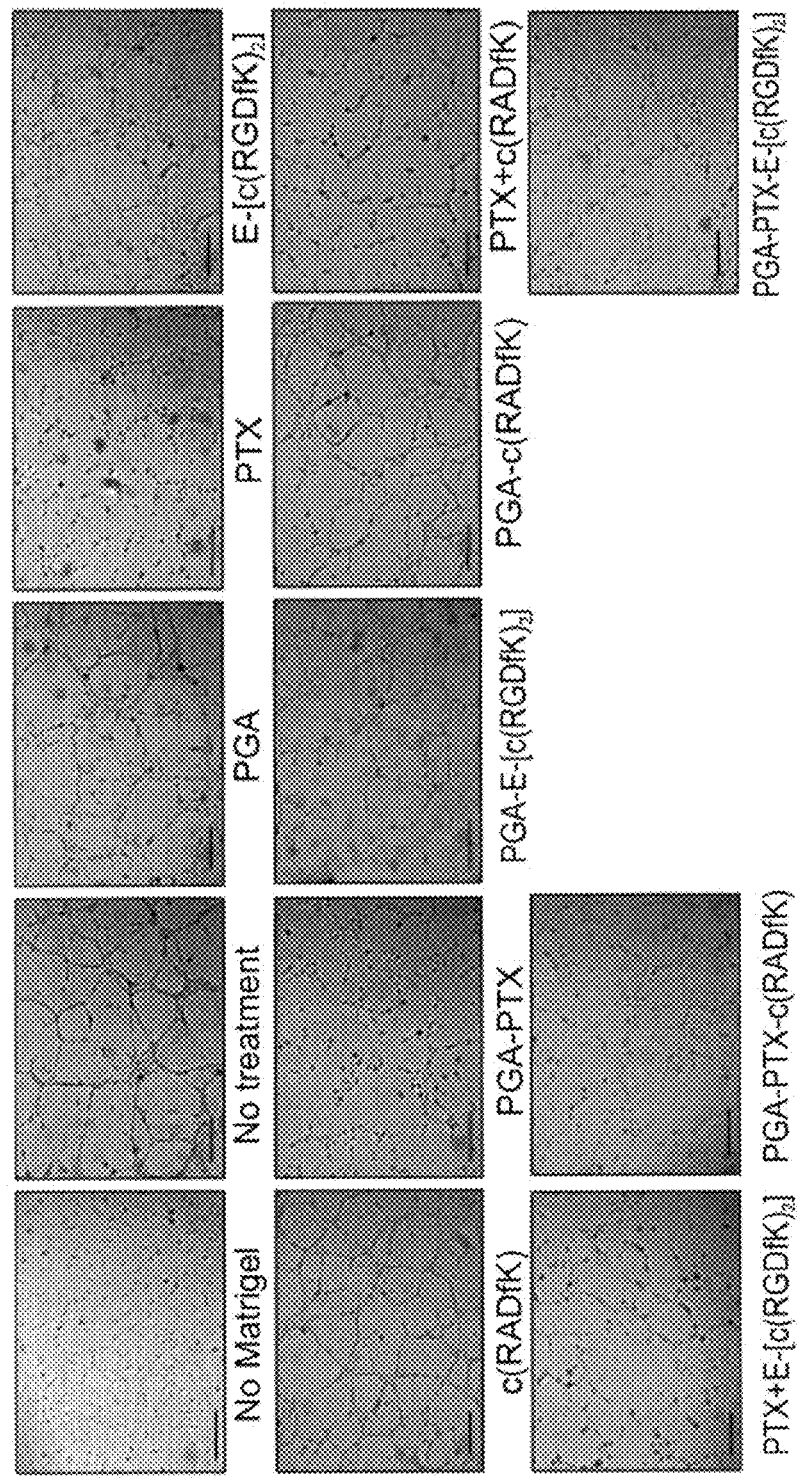
Figure 16B:
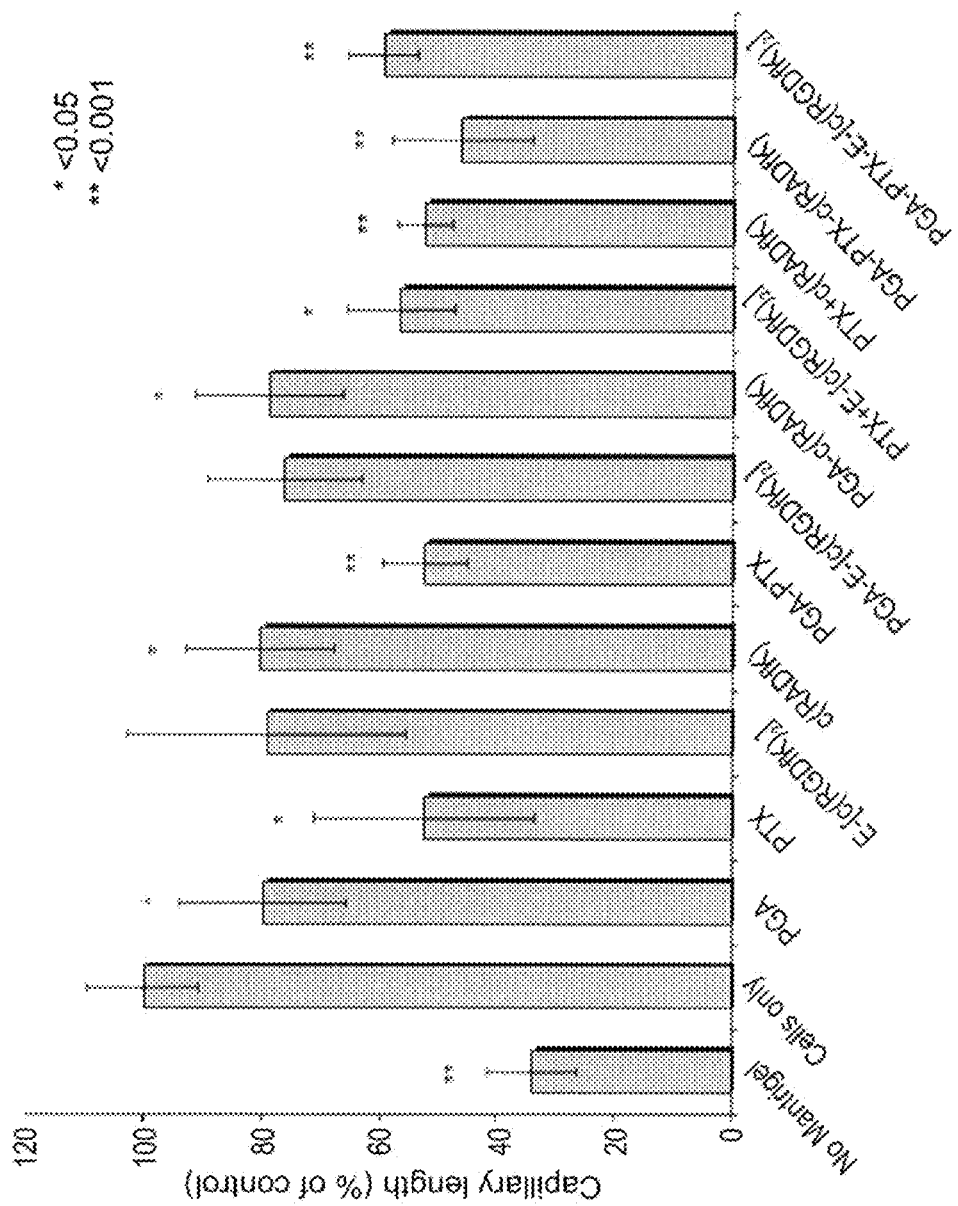

FIGS. 16A-B present images (FIG. 16A) and a bar graph (FIG. 16B) demonstrating that the conjugate PGA-Paclitaxel-c(RGDfk)$_2$ (SEQ ID NO: 18) inhibited capillary-like tube formation of HUVEC. HUVEC (5×10$^4$ cells/100 μl) were challenged with polyglutamic acid polymer alone (PGA); Paclitaxel alone (PTX); bis-cyclic RGD peptide alone (E-[c(RGDfk)$_2$]; SEQ ID NO:2); the inactive cyclic peptide c(RADfk) (c(RADfk); SEQ ID NO:28); Polyglutamic acid conjugated to Paclitaxel (PGA-PTX); Polyglutamic acid polymer conjugated to bis-cyclic RGD peptide (PGA-E-[c(RGDfk)$_2$]; SEQ ID NO:15); Polyglutamic acid polymer conjugated to inactive cyclic peptide c(RADfk) (PGA-c(RADfk); SEQ ID NO:14); a combination of free Paclitaxel together with free the bis-cyclic RGD peptide (PTX+E-[c(RGDfk)$_2$] having SEQ ID NO:2); a combination of free Paclitaxel together with free inactive cyclic peptide c(RADfk) (PTX+c(RADfk) having SEQ ID NO:28); Polyglutamic acid polymer conjugated to Paclitaxel and to the inactive cyclic peptide c(RADfk) (PGA-PTX-c(RADfk); SEQ ID NO:19) and Polyglutamic acid polymer conjugated to Paclitaxel and to bis-cyclic RGD peptide (PGA-PTX-[c(RGDfk)$_2$]; SEQ ID NO:18). The cells were then stained and the percentages of inhibition of HUVEC capillary-like tube structures by the different compounds were determined. Quantification was performed using Nikon TE2000E inverted microscope and NIH image software. Data represent mean±SD.

Figure 17A:
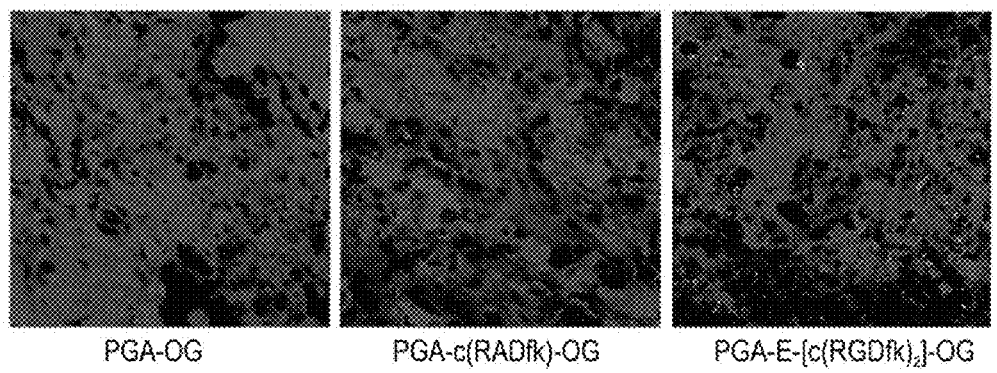
Figure 17B:
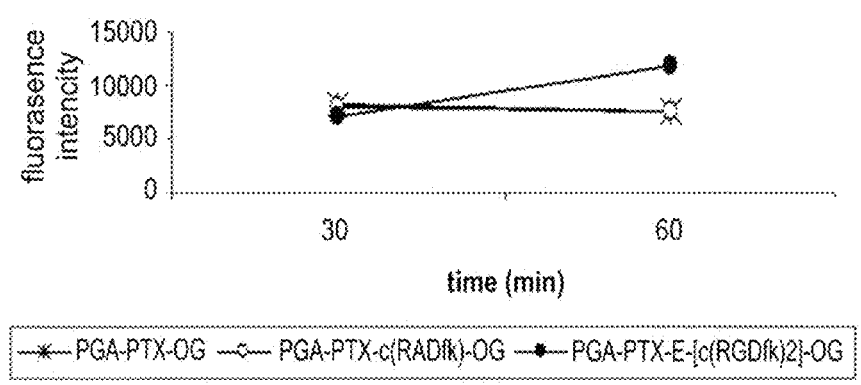

FIGS. 17A-B present data showing the selective accumulation of the conjugates in tumor tissues in vivo. The florescence probe Oregon Green-cadaverine (OG), was conjugated to PGA, PGA-E-[c(RGDfk)$_2$] (SEQ ID NO:15) and PGA-c(RADfk) (SEQ ID NO:14). SCID male were inoculated s.c. with 2×10$^6$ mCherry-labeled U87 human osteosarcoma or with 5×10$^6$ mCherry-labeled MG-63 human osteosarcoma and injected i.v. with PGA-E-[c(RGDfk)$_2$]-OG (SEQ ID NO:25; 50 μM-RGD) or PGA-c(RADfk)-OG (SEQ ID NO: 24; 50 μM-RGD-equivalent dose) or PGA as control (n=3 mice/group). One hour after injection, tumors were removed, dissected to thin slices and examined under Zeiss Meta LSM 510 confocal imaging system. Shown in FIG. 17A are fluorescent images of tumor slices from the treated mice showing that only PGA-E-[c(RGDfk)$_2$] (SEQ ID NO: 15) was able to accumulate in the tumor tissue. FIG. 17B presents comparative plots of the accumulation of PGA-PTX-E-[c(RGDfk)$_2$]-OG (SEQ ID NO:25), PGA-PTX-c(RADfk)-OG (SEQ ID NO:24) and PGA-PTX-OG, as detected via FACS, in the mCherry-labeled-MG-63 cells from homogenized tumors of the treated mice. The results show the PGA-PTX-E-[c (RGDfk)$_2$]-OG (SEQ ID NO: 25) preferential accumulation compared with PGA-PTX-c(RADfk)-OG (SEQ ID NO:24) and PGA-PTX-OG.

DESCRIPTION OF SPECIFIC EMBODIMENTS OF THE INVENTION

The present invention, in some embodiments thereof, relates to novel chemical conjugates and to uses thereof in therapy and diagnosis and, more particularly, but not exclusively, to novel conjugates of polymers having attached thereto an angiogenesis targeting moiety and an anti-angiogenesis agent and to uses thereof in monitoring and treating medical conditions associated with angiogenesis.

The principles and operation of the conjugates, compositions, use, methods and processes according to the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The term "angiogenesis" describes a biological process that involves the sprouting of new blood vessels from pre-existing ones and plays a crucial role in disease development and progression [Folkman J. N Engl J Med 1995, 333:1757-1763]. Angiogenesis is a complex process in which endothelial cells serve as a building block for blood vessel expansion. It is regulated through a fine balance between pro-angiogenic and anti-angiogenic molecules.

Pathological angiogenesis has been demonstrated in several diseases, including cancer, hypertension, rheumatoid arthritis, and diabetic retinopathy. Tumor growth and metastasis are particularly dependent on the degree of angiogenesis.

Inhibition of further vascular expansion has therefore been the focus of active research for cancer therapy. Many drugs have been developed, which target different steps in this multi-step tumor angiogenesis process. However, most of these drugs were shown to be cytostatic rather than cytotoxic and thus do not cause a substantial reduction of tumor volume during the first stage of treatment.

In a search for novel agents for treating medical conditions associated with angiogenesis, the present inventors have devised and successfully prepared and practiced novel conjugates of a biocompatible polymer, which has a therapeutically active agent that is useful as an anti-cancer agent and/or an anti-angiogenesis agent and at least one Arg-Gly-Asp (RGD)-containing moiety (SEQ ID NO: 1) as an angiogenesis targeting moiety attached thereto.

As demonstrated in the Examples section that follows, these novel conjugates were shown to inhibit angiogenesis and angiogenesis related processes, and thus were shown to inhibit endothelial cell proliferation, migration ability of cells to form capillary-like tube structures and adhesion onto fibrinogen coated plates (see, FIGS. 12-16). Furthermore, in vivo experiments showed enhanced accumulation of an exemplary conjugate according to some embodiments of the present invention, denoted as PGA-PTX-E-[c(RGDfk)$_2$] (SEQ ID NO:18), in osteosarcoma tumor cells in mice (FIG. 17).

These conjugates can therefore be beneficially used for the treatment of medical conditions characterized by excessive angiogenesis.

Thus, according to one aspect of embodiments of the invention there is provided a polymeric conjugate comprising a polymeric backbone having attached thereto a therapeutically active agent and an angiogenesis targeting moiety, the angiogenesis targeting moiety comprising a least one Arg-Gly-Asp (RGD)-containing moiety (SEQ ID NO:1) and the therapeutically active agent being an anti-angiogenesis agent and/or an anti-cancer agent.

In some embodiments of the invention, the conjugates described herein comprise a polymeric backbone comprised of a plurality of backbone units, whereby a portion of these backbone units have the therapeutically active agent attached thereto and another portion of these backbone units have the angiogenesis targeting moiety attached thereto. Those backbone units within the polymeric backbone that are not linked to another moiety are referred to herein as "free" or "non-functionalized" backbone units.

Since the polymeric backbone in the conjugates described herein is composed of some backbone units that have the therapeutically active agent attached thereto, some backbone units that have the targeting moiety attached thereto, and optionally some free backbone units, these conjugates represent co-polymers.

The phrase "therapeutically active agent" describes a compound which exhibits a beneficial pharmacological effect when administered to a subject and hence can be used in the treatment of a condition that benefits from this pharmacological effect.

The term "subject" (alternatively referred to herein as "patient") as used herein refers to an animal, preferably a mammal, most preferably a human, who has been the object of treatment, observation or experiment.

The phrase "anti-cancer agent", as used herein, describes any therapeutic agent that directly or indirectly kills cancer cells or directly or indirectly inhibits, stops or reduces the proliferation of cancer cells. Anti-cancer agents include those that result in cell death and those that inhibit cell growth, proliferation and/or differentiation. In some embodiments, the anti-cancer agent is selectively toxic against certain types of cancer cells but does not affect or is less effective against normal cells. In some embodiments, the anti-cancer agent is a cytotoxic agent.

The phrase "cytotoxic agent", as used herein, describes a compound that mediates cell death. Cell death mediation can be exhibited by a mechanism such as, but not limited to, apoptosis, inhibition of metabolism or DNA synthesis, interference with cytoskeletal organization, destabilization or chemical modification of DNA, etc. As used herein, the phrase "cytotoxic agent" encompasses any suitable chemotherapeutic agent, including small organic molecules, peptides, oligonucleotides and the like as well as radiotherapeutic agents such as, for example, radioactive iodine $^{131}$I and beta particle emitter $^{90}$Y. The agent may act, for example, as an anti-proliferative agent or as a pro-apoptotic agent, which induces apoptosis.

Exemplary cytotoxic agents include, without limitation, Anthracycline Antibiotics such as Doxorubicin and Daunorubicin, Taxanes such as Taxol™, Docetaxel, Vinca alkaloids as Vincristine and Vinblastine, 5-Fluorouracil (5 FU), Leucovorin, Irinotecan, Idarubicin, Mitomycin C, Oxaliplatin, Raltitrexed, Tamoxifen and Cisplatin, Carboplatin, Methotrexate, Actinomycin D, Mitoxantrone or Blenoxane or Mithramycin.

The agent can also be a member of the Bio-Reductive drugs that are activated under hypoxic cellular conditions.

Some anti-cancer agents act as angiogenesis inhibitors, as discussed hereinabove.

The phrase "anti-angiogenesis agent", which is also referred to herein interchangeably as "anti-angiogenic agent" or "angiogenesis inhibitor", describes an agent having the ability to (a) inhibit endothelial cell proliferation or migration, (b) kill proliferating endothelial cells, and/or (c) inhibit the formation of new blood vessels in a tissue.

As discussed hereinabove, some anti-angiogenesis agents are useful in the treatment of cancer and hence can also be referred to as anti-cancer agents.

In some embodiments the anti-angiogenesis agent is Paclitaxel.

The chemical structure of Paclitaxel is shown in FIG. 2B. The microtubule-interfering agent Paclitaxel is a drug commonly used for the treatment of advanced metastatic breast cancer. However, it is neurotoxic, it causes hematological toxicity and many breast tumors develop resistance thereto. It has been recently shown that Paclitaxel at ultra low doses inhibits angiogenesis. However, Paclitaxel is poorly soluble in aqueous solutions and the excipients Cremophor EL or ethanol used today to solubilize its commercial form, cause hypersensitivity reactions.

As demonstrated in the Examples section which follows, a conjugate comprising Paclitaxel, according to some embodiments of the invention, at a concentration in which Paclitaxel has been known to exhibit anti-angiogenesis activity, has been tested for its anti-angiogenesis activity. Specifically, the conjugate being a Polyglutamic acid co-polymer in which two RGD-containing cyclic peptides and Paclitaxel are conjugated to the polymeric backbone (PGA-E-c(RGDfk)$_2$-PTX; SEQ ID NO:18) has been shown to exhibit anti-angiogenesis activity, namely inhibit endothelial cell proliferation, migration, ability of cells to form capillary-like tube structures and adhesion onto fibrinogen coated plates (see, FIGS. 12-16). Another conjugate being a Polyglutamic acid polymer linked to one RGD-containing cyclic peptide and to Paclitaxel (PGA-c(RGDfk)-PTX; SEQ ID NO:16) has been also shown to exhibit anti-angiogenesis activity (see, FIGS. 13B and 15). These results demonstrate the ability of the conjugates described herein, to inhibit angiogenesis and therefore to serve as potent anti-angiogenesis agents.

In some embodiments the anti-angiogenesis agent is TNP-470.

TNP-470 is a low molecular weight synthetic analogue of fumagillin, which is capable of selectively inhibiting endothelial growth in vitro. In clinical trials, this drug was found to slow tumor growth in many patients with metastatic cancer and exhibited a promising efficacy when used in combination with conventional chemotherapy. However, at the doses required for tumor regression, many TNP-470-treated patients experienced neurotoxicity. Due to its dose-limiting neurotoxicity, no further clinical studies were conducted for using TNP-470 per se. A representative chemical structure of a TNP-470 containing conjugate (PGA-TNP-470-[c(RGDfk)$_2$]; SEQ ID NO:21), according to some embodiments of the present invention, is presented in FIG. 4D.

Other anti-angiogenesis agents that are suitable for use in the context of embodiments of the invention include, but are not limited to, paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, a matrix metalloproteinase, penicillamine, PTK787/ZK 222584, RPI.4610, squalamine lactate, SU5416, thalidomide, combretastatin, tamoxifen, COL-3, neovastat, BMS-275291, SU6668, anti-VEGF antibody, Medi-522 (Vitaxin II), CAI, Interleukin-12, IM862, Amilloride, Angiostatin®Protein, Angiostatin K1-3, Angiostatin K1-5, Captopril, DL-alpha-Difluoromethylornithine, DL-alpha-Difluoromethylornithine HCl, His-Tag® Endostatin™Protein, Endostar™, Fumagillin, Herbimycin A, 4-Hydroxyphenylretinamide, Juglone, Laminin, Laminin Hexapeptide, Laminin Pentapeptide, Lavendustin A, Medroxyprogesterone, Medroxyprogesterone Acetate, Minocycline, Minocycline HCl, Placental Ribonuclease Inhibitor, Suramin, Sodium Salt Suramin, Human Platelet Thrombospondin, Neutrophil Granulocyte, monoclonal antibodies directed against specific proangiogenic factors and/or their receptors (e.g. Avastin, Erbitux, Vectibix, Herceptin); small molecule tyrosine kinase inhibitors of multiple pro-angiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); ZD6474, SU11248, Vitaxin; Squalamin; COX-2 inhibitors; PDGFR inhibitors (e.g., Gleevec); NM3 and 2-ME2.

In some embodiments, the anti-angiogenesis agent is selected from the group consisting of Paclitaxel, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3; 2-ME2 and Bisphosphonates (e.g., Zoledronate).

As used herein, the term "COX-2 inhibitor" refers to a non-steroidal drug that relatively inhibits the enzyme COX-2 in preference to COX-1. Preferred examples of COX-2 inhibitors include, but are no limited to, celecoxib, parecoxib, rofecoxib, valdecoxib, meloxicam, and etoricoxib.

The phrase "angiogenesis targeting moiety" describes a chemical moiety that can bind to a location in a mammal in which neovascularization, such as neovascularization of tumor cells, occurs. The phrase "neovascularization" is meant to encompass two unique processes: vasculogenesis, the de novo assembly of blood vessels, and angiogenesis, the formation of new capillary sprouts from pre-existing vessels.

The angiogenesis targeting moiety described herein is derived from compounds that can selectively bind to a location in a mammal in which neovascularization occurs and hence may serve to deliver the conjugate described herein to the desired location.

In some embodiments the targeting moiety is capable of binding to an angiogenesis-associated integrin. In some embodiments, the targeting moiety targets the $\alpha_v\beta_3$ integrin receptor.

Integrins are a class of receptors involved in the mechanism of cell adhesion. The integrins are heterodimeric transmembrane glycoproteins that compose a diverse family of 19α and eight β subunits. An integrin with a well-characterized involvement in angiogenesis and tumor invasiveness is $\alpha_v\beta_3$ [Stromblad and Cheresh, Chem Biol 1996; 3:881-885]. The $\alpha_v\beta_3$ integrin is overexpressed on proliferating endothelial cells such as those present in growing tumors, as well as on some tumor cells of various origins. The RGD sequence (SEQ ID NO:1) represent the minimal amino acid domain, in several extracellular matrix proteins, which has been demonstrated to be the binding site of the transmembrane integrins proteins family [Bazzoni et al. 1999, Current Opinion in Cell Biology; (11) pp. 573-581].

Accordingly, in some embodiments, the angiogenesis targeting moiety comprises a least one Arg-Gly-Asp (RGD) moiety (SEQ ID NO:1), or a peptidomimetic thereof, and can optionally further include other amino acids, amino acid derivatives, or other chemical groups (e.g., alkylene chains).

In some embodiments, the RGD-containing moiety (SEQ ID NO:1) is an oligopeptide. The oligopeptide can be a cyclic oligopeptide (including, for example, monocyclic, bicyclic and tricyclic oligopeptides) or a linear oligopeptide, and can include, in addition to the Arg-Gly-Asp amino acid sequence (SEQ ID NO:1), from 1 to 10 amino acids.

It has been further found that the substrate specificity of RGD-containing moieties (SEQ ID NO:1) results from the different conformations of the RGD sequence in different matrix proteins.

In an embodiment, the oligopeptide is a cyclic peptide being c[Arg-Gly-Asp-Phe-Lys] (SEQ ID NO:9).

In some embodiments, the angiogenesis targeting moiety comprises two or more Arg-Gly-Asp-containing moieties (SEQ ID NO:1), wherein the moieties can be the same or different.

Exemplary Arg-Gly-Asp-containing moieties (SEQ ID NO:1) that are suitable for use in the context of embodiments of the invention include, but are not limited to c(RGDfk) (SEQ ID NO:9), RGD4C (SEQ ID NO:5), and other RGD-containing cyclic peptides such as those described in Haubner et al. [*J. Am. Chem. Soc.* 1996, 118, 7881-7891] and Capello, et al. [*J. Nucl. Med.* 2004, 45(10), 1716-20] and in WO 97/06791 and U.S. Pat. No. 5,773,412. Exemplary effective RGD cyclic peptides are the Arg-Gly-Asp (RGD) cyclic pentapeptides in which two amino acids such as D-tyrosine and lysine were added to the RGD and the pentapeptide was transformed into cyclic pentapeptide.

In some embodiments, the RGD-containing moiety can comprise two or more -Arg-Gly-Asp- moieties (SEQ ID NO:1), being either linked to one another or being spaced by one or more amino acids or any other spacer, as defined herein.

As demonstrated in the Examples section that follows, an RGD-containing moiety c(RGDfk)$_2$ conjugated to a PGA polymeric backbone (SEQ ID NO:15) bound to a greater extent to cells expressing the $\alpha_v\beta_3$ integrin as compared to a PGA conjugate of the inactive RAD moiety or PGA alone (SEQ ID NO:14) (see, FIGS. 11B and 11C), thereby demonstrating that the RGD moiety plays a key role in the interaction and subsequent internalizations of the conjugates into the cells.

In some embodiments, the anti-angiogenesis agent is Paclitaxel and the angiogenesis targeting moiety comprises a cyclic oligopeptide being c[Arg-Gly-Asp-Phe-Lys] (SEQ ID NO:9).

In some embodiments the anti-angiogenesis agent is Paclitaxel and the angiogenesis targeting moiety comprises two cyclic oligopeptides each being c[Arg-Gly-Asp-Phe-Lys] (SEQ ID NO:9). Such a conjugate is referred to herein as a conjugate that contains a bis-cyclic RGD-containing moiety.

Herein, the phrases "loading onto the polymer", or simply "load", are used to describe the amount of an agent that is attached to the polymeric backbone of the conjugates described herein, and is represented herein by the mol % of this agent in the conjugate, as defined hereinafter.

As used herein, the term "mol %" describes the number of moles of an attached moiety per 1 mol of the polymeric conjugate, multiplied by 100.

Thus, for example, a 1 mol % load of an angiogenesis targeting moiety describes a polymeric conjugate composed of 100 backbone units, whereby 1 backbone unit has a targeting moiety attached thereto and the other 99 backbone units are either free or have other agents attached thereto.

The optimal degree of loading of the therapeutically active agent and angiogenesis targeting moiety for a given conjugate and a given use is determined empirically based on the desired properties of the conjugate (e.g., water solubility, therapeutic efficacy, pharmacokinetic properties, toxicity and dosage requirements), and optionally on the amount of the conjugated moiety that can be attached to a polymeric backbone in a synthetic pathway of choice.

The % loading can be measured by methods well known by those skilled in the art, some of which are described hereinbelow under the Materials and Methods of the Examples section that follows.

In some embodiments, the loading of the therapeutically active agent in the polymer is greater than 1 mol %.

In some embodiments, the loading of the therapeutically active agent in the conjugate ranges from 1 mol % to 99 mol %, from 1 mol % to 50 mol %, from 1 mol % to 20 mol %, from 1 mol % to 10 mol 5, or from 1 mol % to 5 mol %.

In some embodiments the loading of the angiogenesis targeting moiety in the polymer is greater than 1 mol %.

In some embodiments, the loading of the angiogenesis targeting moiety in the conjugate ranges from 1 mol % to 99 mol %, from 1 mol % to 50 mol %, from 1 mol % to 20 mol %, from 1 mol % to 10 mol %, or from 1 mol % to 5 mol %.

As exemplified in the Examples section that follows, conjugates having a different % loading of the therapeutically active agent and angiogenesis targeting moiety were synthesized (see, Table 1) and their anti-angiogenesis activity was determined. Specifically, an anti-angiogenesis activity was shown for both a PGA-PTX-E-[c(RGDfk)$_2$] conjugate (SEQ ID NO:18) having a 3.9 mol % E-[c(RGDfk)$_2$] and 5.5 mol % PTX loading (see, FIGS. 12 and 14-16) as well as for the PGA-PTX-E-[c(RGDfk)$_2$] conjugate (SEQ ID NO:18) having a 5 mol % E-[c(RGDfk)$_2$] and 2.6 mol % PTX loading (see, FIGS. 13A and 15).

As further demonstrated in the Examples section that follows, the Arg-Gly-Asp (RGD)-containing moiety (SEQ ID NO: 1), for example E-[(cRGDfk)$_2$] (SEQ ID NO: 2), has inherent anti-angiogenesis characteristic namely the inhibition of endothelial cell migration toward the chemoattractant VEGF and attachment to fibrinogen coated plates (see, FIGS. 14 and 15). No antagonistic activity of the Arg-Gly-Asp (RGD)-containing moiety (SEQ ID NO:1) against the anti-angiogenesis activity of Paclitaxel was observed, as assessed by the anti-proliferative activity against HUVEC, but rather the anti-proliferative activity of the E-[(cRGDfk)$_2$] (SEQ ID NO:2) and Paclitaxel, when the cells were subjected to both drugs together, was additive in nature (see, FIG. 12).

Cyr61 (also known as CCN1) is a Cysteine-rich matricellular protein that supports cell adhesion and induces adhesion signaling. Furthermore, Cyr61 stimulates endothelial cell migration and enhances growth factor induced DNA synthesis in culture and therefore induces angiogenesis in vivo. Mechanistically, Cyr61 acts as a non-RGD-containing ligand of integrin receptors. Functional blockade of $\alpha v\beta 3$, a Cyr61 integrin receptor, is specifically cytotoxic towards Cyr61-overexpressing breast cancer cells and a specific $\alpha v\beta 3$-RGD peptidomimetic agent (SEQ ID NO: 28) prevents $\alpha v\beta 3$ from binding to its ligand, Cyr61. It has been recently shown that Cyr61 overexpression can render human breast cancer cells highly resistant to Paclitaxel.

In some embodiments, the conjugates described herein act as specific antagonists of $\alpha v\beta 3$ and consequently inhibit the Cyr61-integrin receptor signal transduction cascade, thereby serving to inhibit Cyr-61 dependent cancer cell growth and chemoresistance.

In some embodiments, the polymeric conjugates described herein are composed of a polymeric backbone, formed from a plurality of backbone units that are covalently linked to one another, wherein at least a portion of this plurality of backbone units has a therapeutically active agent, as described herein, attached thereto, and at least another portion of the plurality of backbone units has the angiogenesis targeting moiety (the RGD containing moiety, (SEQ ID NO:1) as described herein), attached thereto.

Those backbone units that have the therapeutically active agent attached thereto and those backbone units that have the angiogenesis targeting moiety attached thereto can be randomly dispersed within the polymeric backbone.

The polymeric backbone can further include non-functionalized backbone units, as discussed hereinbelow, to which none of the therapeutically active agent and the angiogenesis targeting moiety are attached.

In some embodiments, the polymeric backbone of the conjugates described constitutes polymers (or co-polymers) to which the angiogenesis targeting moiety and the therapeutically active agent are attached.

Polymers which are suitable for use in the context of the present embodiments are biocompatible, non-immunogenic and non-toxic. The polymers serve as carriers that enable specific delivery into tumor tissue. As described hereinabove, the specific delivery is due to the enhanced permeability and retention (EPR) effect discussed hereinabove. Furthermore, conjugation to polymers should restrict the passage through the blood brain barrier and would prolong the circulating half-life of the drugs, hence inhibiting the growth of tumor endothelial and epithelial cells by exposing the cells to the conjugated drugs in the circulation for a longer time compared to the free drugs. Additionally, polymer-drug conjugates may act as drug depots for sustained release, producing prolonged drug exposure to tumor cells. Finally, water soluble polymers (e.g., water soluble polyamino acids) may be used to stabilize drugs, as well as to solubilize otherwise insoluble compounds such as, for example TNP-470 and Paclitaxel.

As used herein, the term "polymer" describes an organic substance composed of a plurality of repeating structural units (backbone units) covalently connected to one another. The term "polymer" as used herein encompasses organic and inorganic polymers and further encompasses one or more of a homopolymer, a copolymer or a mixture thereof (a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone unit can differ from one another by the pendant groups thereof.

The polymer is comprised of backbone units formed by polymerizing the corresponding monomeric units whereby the therapeutically active agent and the angiogenesis targeting moiety are attached to at least a portion of these backbone units. Some or all of these backbone units are typically functionalized prior to conjugation so as to have a reactive group for attaching the anti-angiogenesis agent and the bone targeting moiety. Those backbone units that are not functionalized and/or do not participate in the conjugations of the therapeutically active agent and the angiogenesis targeting moiety are referred to herein as "free" backbone units.

The polymer may be a biostable polymer, a biodegradable polymer or a combination thereof. The term "Biostable" describes a compound that is not degraded in vivo, i.e., is not biodegradable.

The term "biodegradable", describes a substance that which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The polymers can be water-soluble or water-insoluble. In some embodiments, the polymers are water soluble at room temperature.

The polymers can further be charged polymers or non-charged polymers. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be non-charged.

In some embodiments, the polymer has an average molecular weight in the range of 100 Da to 800 kDa. In some embodiments, the polymer has an average molecular weight lower than 100 kDa or lower than 60 kDa. In some embodiments, the polymer's average molecular weight range is 10 kDa to 40 kDa.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

The polymer used in the context of embodiments of the invention can be a synthetic polymer or a naturally-occurring polymer. In some embodiments, the polymer is a synthetic polymer.

The polymeric backbone of the polymer described herein may be derived from, for example, polyacrylates, polyvinyls, polyamides, polyurethanes, polyimines, polysaccharides, polypeptides, polycarboxylates, and mixtures thereof.

Exemplary polymers which are suitable for use in the context of the present embodiments include, but are not limited to, dextran, a water soluble polyamino acid, a polyethyleneglycol (PEG), a polyglutamic acid (PGA), a polylactic acid (PLA) a polylactic-co-glycolic acid (PLGA), a poly(D,L-lactide-co-glycolide) (PLA/PLGA), a poly(hydroxyalkylmethacrylamide), a polyglycerol, a polyamidoamine (PAMAM), and a polyethylenimine (PEI).

In some embodiments, the polymeric backbone is derived from a poly(hydroxyalkylmethacrylamide) or a copolymer thereof. Such a polymeric backbone comprises methacrylamide backbone units.

Poly(hydroxyalkylmethacrylamide) (HPMA) polymers are a class of water-soluble synthetic polymeric carriers that have been extensively characterized as biocompatible, non-immunogenic and non-toxic. One advantage of HPMA polymers over other water-soluble polymers is that they may be tailored through relatively simple chemical modifications, in order to regulate their respective drug and targeting moiety content. Further, the molecular weight and charge of these polymers may be manipulated so as to allow renal clearance and excretion from the body, or to alter biodistribution while allowing tumor targeting.

According to some embodiments, the polymer is Polyglutamic acid (PGA).

The chemical structure of PGA is shown in FIG. 2A. PGA contains a large number of side chain carboxylic functional groups which can be readily utilized for drug attachment. PGA can be readily degraded by lysosomal enzymes such as Cathepsin B, to its nontoxic basic components, L-glutamic acid, D-glutamic acid and D,L-glutamic acid. Sodium glutamate has been reported to prevent manifestations of neuropathy induced by Paclitaxel, thus enabling higher doses of Paclitaxel to be tolerated.

As used herein, "a polyglutamic acid" or "polyglutamic acid polymer" encompasses poly(L-glutamic acid), poly(D- glutamic acid), poly(D,L-glutamic acid), poly(L-gamma glutamic acid), poly(D-gamma glutamic acid) and poly(D,L-gamma glutamic acid).

In some embodiments, the polyglutamic acid comprises at least 50% of its backbone units as glutamic acid, and optionally comprises, 60, 70, 80, 90 or 100% of its backbone units as glutamic acid. The polyglutamic acid can be substituted by naturally occurring or chemically modified amino acids, preferably hydrophilic amino acids, provided that when conjugated to the therapeutically active agent and the angiogenesis targeting moiety, the substituted polyglutamic acid polymeric backbone has improved aqueous solubility and/or improved efficacy relative to the unconjugated therapeutic agent, and is preferably non-immunogenic. Up to 50% of the backbone units of the polyglutamic acid polymeric backbone can be substituted.

A representative general formula of a polyglutamic acid based conjugate wherein the polymeric backbone has a therapeutically active agent conjugated thereto through a degradable linker and further has an angiogenesis targeting moiety conjugated thereto, is shown in FIG. 1.

According to some embodiments, the polymer is polyethylenglycol (PEG).

PEG is a unique polyether diol, usually manufactured by the aqueous anionic polymerization of ethylene oxide, although other polymerization initiators can be employed. This polymer is amphiphilic and dissolves in organic solvents as well as in water; it is also non-toxic and is eliminated by a combination of renal and hepatic pathways. Furthermore, PEG has the lowest level of protein or cellular absorption of any known polymer and hence is advantageous for drug conjugation. The structure of a PEG based conjugate, according to the embodiments of the present invention, is shown in FIG. 5.

It is to be understood that the polymers as discussed herein describe those polymers that are formed from homogenic or heterogenic, non-functionalized monomeric units, and that the polymeric backbone constituting the polymeric conjugate corresponds to such polymers by being comprised of the same monomeric units, while some of these monomeric units are functionalized, as described herein. Thus, the polymeric backbone of the polymeric conjugate is similar to that of the polymers described herein, and differs from the polymers by having the above-described agents attached to some of the backbone units therein.

As discussed hereinabove, the tumor vasculature possesses an enhanced capacity for the uptake of macromolecules and colloidal drug carriers having a high molecular weight and large hydrodynamic diameter due to the EPR effect. Therefore, a conjugate as described herein, having a large enough hydrodynamic diameter is beneficial. The term "large enough" is used herein to describe a conjugate having a hydrodynamic diameter which leads to an increase in the ratio of conjugate accumulated in the tumor tissue as compared to other tissues. The determination of the optimal ratio is well within the capability of those skilled in the art. For example, the ratio may be 1.1, 2, 3, 4, 5 etc. In some embodiments, the hydrodynamic diameter is in the range of from 10 nm to 200 nm. In some embodiments, the hydrodynamic diameter is in the range of from 10 nm to 100 nm. In some embodiments the hydrodynamic diameter is in the range of from 20 nm to 50 nm. In yet another embodiment the hydrodynamic diameter is 40 nm. In yet another embodiment the hydrodynamic diameter is 30 nm. The hydrodynamic diameter can be measured as described below under the Materials and Methods of the Example section which follows hereinbelow. The hydrodynamic diameter of nano-scale particles of a Polyglutamate copolymer to which Paclitaxel and a bis-cyclic RGD containing peptide (PGA-PTX-E-[c(RGDfk)$_2$]; SEQ ID NO:18) were conjugated to the polymeric backbone as well as a Polyglutamate copolymer to which Paclitaxel and a monocyclic RGD containing peptide (PGA-PTX-c[RGDfk]; SEQ ID NO:16) was conjugated to the polymeric backbone is shown in FIG. 9.

In each of the conjugates described herein, the therapeutically active agent and the angiogenesis targeting moiety can each be linked to the respective portion of the backbone units in the polymeric backbone directly, or indirectly, through a linker moiety (also referred to herein as a linker, a linker group or a linking group), whereby, in some embodiments, the direct/indirect linkage is designed as being cleavable at conditions characterizing the desired bodily site (e.g., by certain enzymes or pH), as detailed hereinbelow.

Hence, according to some embodiments, at least one of the therapeutically active agent and the targeting moiety is attached to the polymer via a linker. In some embodiments, each of the therapeutically active agent and the targeting moiety is attached to the polymer via a linker. The linker linking the therapeutically active agent to the polymer and the linker linking the angiogenesis targeting moiety to the polymer may be the same or different.

The linker described herein refers to a chemical moiety that serves to couple the angiogenesis targeting moiety and/or the therapeutically active agent to the polymeric backbone while not adversely affecting either the targeting function of the angiogenesis targeting moiety or the therapeutic effect of the angiogenesis targeting moiety and/or therapeutically active agent.

In some embodiments, the linker is a biodegradable linker.

The phrase "biodegradable linker", as used herein, describes a linker that is capable of being degraded, or cleaved, when exposed to physiological conditions. Such physiological conditions can be, for example, pH, a certain enzyme, and the like.

In some embodiments, the linker is capable of being cleaved by pre-selected cellular enzymes, for instance, those found in osteoblasts, osteoclasts, lysosomes of cancerous cells or proliferating endothelial cells. Alternatively, an acid hydrolysable linker could comprise an ester or amide linkage and be for instance, a cis-aconityl linkage. Such linkers further enhance the therapeutic activity and reduced toxicity of the conjugates described herein, by allowing the release of the anti-angiogenesis drug and/or the alendronate only at the desired bodily site.

Accordingly, according to some embodiments, the biodegradable linker is a pH-sensitive linker or an enzymatically-cleavable linker.

A pH-sensitive linker comprises a chemical moiety that is cleaved or degraded only when subjected to a certain pH condition, such as acidic pH (e.g., lower than 7), neutral pH (6.5-7) or basic pH (higher than 7).

Such a linker may, for example, be designed to undergo hydrolysis under acidic or basic conditions, and thus, the conjugate remains intact and does not release the agents attached to the polymer in the body, until its reaches a physiological environment where a pH is either acidic or basic, respectively.

Exemplary pH-sensitive linkers include, but are not limited to a hydrazone bond, an ester (including orthoester) bond, an amide bond of, for example, a cis-aconytil residue, a trityl group, an acetal, a ketal, an Alanine ester, a Gly-ester and a -[Gly-Phe-Gly]-moiety (SEQ ID NO: 29).

In some embodiments the biodegradable linker is an enzymatically-cleavable linker. Such a linker is typically designed so as to include a chemical moiety, typically, but not exclusively, an amino acid sequence that is recognized by a pre-selected enzyme. Such an amino acid sequence is often referred to in the art as a "recognition motif". A conjugate comprising such a linker typically remains substantially intact in the absence of the pre-selected enzyme in its environment, and hence does not cleave or degrade so as to the release the agent attached thereto until contacted with the enzyme.

In some embodiments, the enzymatically cleavable linker is cleaved by an enzyme which is overexpressed in tumor tissues. A conjugate comprising such a linker ensures, for example, that a substantial amount of the conjugated therapeutically active agent is released from the conjugate only at the tumor tissue, thus reducing the side effects associated with non-selective administration of the drug and further enhancing the concentration of the drug at the tumor site.

Exemplary enzymes which are suitable for use in the context of these embodiments include, but are not limited to the group consisting of Cathepsin B, Cathepsin K, Cathepsin D, Cathepsin H, Cathepsin L, legumain, MMP-2 and MMP-9.

Suitable linkers include, but are not limited to, alkyl chains; alkyl chains optionally substituted with one or more substituents and in which one or more carbon atoms are optionally interrupted by a nitrogen, oxygen and/or sulfur heteroatom.

Other suitable linkers include amino acids and/or oligopeptides.

Such alkyl chains and/or oligopeptides can optionally be functionalized so as allow their covalent binding to the moieties linked thereby (e.g., the polymeric backbone and the targeting moiety, the polymer and the therapeutically active agent). Such a functionalization may include incorporation or generation of reactive groups that participate in such covalent bindings, as detailed hereinunder.

In some embodiment, the linker is a biodegradable oligopeptide which contains, for example, from 2 to 10 amino acid residues.

In some embodiments, the linker is a Cathepsin B-cleavable linker.

Cathepsin B is a lysosomal enzyme overexpressed in both epithelial and endothelial tumor cells. Suitable linkers having cathepsin-B cleavable sites include amino acid sequences such as, but are not limited to -[Cit-Val]- (SEQ ID NO: 29), -[Arg]-, -[Arg-Arg]- (SEQ ID NO:31), -[Phe-Lys]- (SEQ ID NO:12), [Gly-Phe-Leu-Gly] (SEQ ID NO: 10), -[Gly-Phe-Ala-Leu]- (SEQ ID NO: 32) and -[Ala-Leu-Ala-Leu]- (SEQ ID NO: 33), -[Gly-Leu-Gly]- (SEQ ID NO: 34), -[Gly-Phe-Gly]- (SEQ ID NO: 35), -[Gly-Phe-Leu-Gly-Phe-Lys]- (SEQ ID NO: 36) and combinations thereof.

In some embodiments the linker comprises the amino acid sequences -[Gly-Leu-Gly]- (SEQ ID NO: 34), -[Gly-Phe-Gly]- (SEQ ID NO: 35), -[Gly-Leu-Phe-Gly]- (SEQ ID NO: 37), -[Gly-Phe-Leu-Gly]- (SEQ ID NO: 10), -[Phe-Lys]- (SEQ ID NO: 12) and -[Gly-Phe-Leu-Gly-Phe-Lys]- (SEQ ID NO: 36). In some embodiments, the linker consists of these amino acid sequences or a combination thereof.

As discussed hereinabove, PGA can be readily degraded by Cathepsin B, to its nontoxic basic components, L-glutamic acid, D-glutamic acid and D,L-glutamic acid.

As demonstrated in the Examples section that follows, Cathepsin B releases the anti-angiogenesis agent Paclitaxel from a conjugate of the drug with PGA polymer (see, FIG. 10).

Matrix metalloproteinases (MMP), in particular MMP-2 and MMP-9, have been identified as important proteases for the progression of malignant tumors. Suitable linkers having MMP-2 and MMP-9 cleavable sites include, but are not limited to, -[Gly-Pro-Gln-Gly-Ile-Ala-Gly-Gln]- (SEQ ID NO:38), -[Gly-Pro-Leu-Gly-Ile-Ala-Gly-Gln]- (SEQ ID NO:11), -[Gly-Pro-Gln-Gly-Ile-Trp-Gly-Gln]- (SEQ ID NO:39) and combinations thereof.

In some embodiments, the linker comprises -[Gly-Phe-Leu-Gly]- (SEQ ID NO:10).

In some embodiments the linker comprises -[Gly-Pro-Leu-Gly-Ile-Ala-Gly-Gln]- (SEQ ID NO:11).

An oligopeptide linker which contains the pre-selected amino acid sequence (recognition motif) can also be constructed such that the recognition motif is repeated several times within the linker, to thereby enhance the selective release of the attached agent. Various recognition motifs of the same or different enzymes can also be incorporated within the linker. Similarly, the linker may comprise multiple pH sensitive bonds or moieties. Linkers comprising such multiple cleavable sites can enhance the selective release of the therapeutically active agent at the desired bodily site, thereby reducing adverse side effects, and further enhance the relative concentration of the released drug at the bodily site when it exhibits its activity.

In cases where the angiogenesis targeting moiety and/or the therapeutically active agent is bound directly to the polymeric backbone, the bond linking these moieties can also be biodegradable, for example, an enzymatically-cleavable bond or a pH-sensitive bond. Such a bond can be formed upon functionalizing the polymeric backbone, the angiogenesis targeting moiety and/or the therapeutically active agent, so as to include compatible reactive groups, as defined herein, for forming the required bond.

The peptide linker may also include a peptide sequence which serves to increase the length of the linker. Longer peptides may be advantageous due to a more efficient steric interaction of the linker with the cleaving enzyme due to enhanced accessibility.

In some embodiments the angiogenesis targeting moiety is linked to the polymeric backbone or to the linker via a spacer. In some embodiments the therapeutically active agent is linked to the polymeric backbone or to the linker via a spacer. The spacers can be the same or different.

The term "spacer" as used herein describes a chemical moiety that is covalently attached to, and interposed between, the polymeric backbone and the linker, or the angiogenesis targeting moiety/therapeutically active agent thereby forming a bridge-like structure between the polymeric backbone and/or the angiogenesis targeting moiety/therapeutically active agent. Alternatively, the spacer may be covalently attached to, and interposed between, the linker and the therapeutically active agent and/or the angiogenesis targeting moiety.

Hence, according to some embodiments at least one of the therapeutically active agent and the angiogenesis targeting moiety is attached to the polymeric backbone and/or to the linker via a spacer.

Suitable spacers include, but are not limited to, alkylene chains, optionally substituted by one or more substituents and which are optionally interrupted by one or more nitrogen, oxygen and/or sulfur heteroatom.

Other suitable spacers include amino acids and amino acid sequences, optionally functionalized with one or more reactive groups for being coupled to the polymeric backbone/angiogenesis targeting moiety/therapeutically active agent/linkers.

In some embodiments, the spacer has the formula G-$(CH_2)$n-K, wherein n is an integer from 1 to 10; and G and K are each a reactive group such as, for example, NH, O or S. In some embodiments, G and K are each NH and n is 2.

An exemplary spacer is —[NH—$(CH_2)_m$NH$_2$]— wherein "m" stands for an integer ranging from 1-10. Preferably m is 2. A conjugate wherein the spacer linking the anti-angiogenesis agent (i.e. TNP470) to a Polyglutamate polymeric unit is —[NH—(CH$_2$)$_2$NH$_2$]— is shown in FIGS. 4B, 4C and 4D.

In some embodiments, the spacer is an amino acid sequence, optionally an inert amino acid sequence (namely, does not affect the affinity or selectivity of the conjugate). Such a spacer can be utilized for elongating or functionalizing the linker.

In some embodiments, the spacer is a glutamate residue (-E-). For example, a conjugate wherein the spacer linking the angiogenesis targeting moiety to a polyglutamate polymeric backbone is a glutamate residue (-E-), is shown in FIG. 4D.

In some cases, a spacer is utilized for enabling a more efficient and simpler attachment of the angiogenesis targeting moiety and/or therapeutically active agent to the polymeric backbone or linker, in terms of steric considerations (renders the site of the polymer to which coupling is effected less hindered) or chemical reactivity considerations (adds a compatible reactive group to the site of the polymer to which coupling is effected). In some cases, the spacer may contribute to the performance of the resulting conjugate. For example, the spacer may render an enzymatically cleavable spacer less sterically hindered and hence more susceptible to enzymatic interactions.

In some cases the spacer is utilized for enabling a more efficient and simpler synthesis of the conjugate by altering the solubility of the therapeutically active agent and/or the angiogenesis targeting moieties to which the spacer is attached (i.e. either more hydrophobic or more hydrophilic).

In some embodiments, the spacer is a degradable spacer, which is capable of undergoing degradation reactions so as to release the agent attached thereto. In some embodiments, the spacer is biodegradable, as defined herein.

In some embodiments, the spacer is a multivalent moiety that is used so as to attach two or more moieties to a backbone unit in the polymeric backbone. Exemplary such a spacer is a glutamate residue, which is used, for example, to attach two cyclic RGD-containing moieties to a polymeric backbone.

A spacer may also be used in order to attach other agents (e.g., a labeling agent, as described hereinbelow) to the conjugate.

The spacer may be varied in length and in composition, depending on steric consideration and may be used to space the angiogenesis targeting moiety and/or therapeutically active agent form the polymeric backbone.

As discussed hereinabove, the optimal degree of loading of the therapeutically active agent and the angiogenesis targeting moiety is determined empirically based on the desired properties of the conjugate (e.g., water solubility, therapeutic efficacy, pharmacokinetic properties, toxicity and dosage requirements), and synthetic considerations (e.g., the amount of the conjugated moiety that can be conjugated to the polymeric backbone in the synthesis mode utilized).

The number of backbone units within the polymeric backbone that have a therapeutically active agent conjugated thereto is defined herein as "y", the number of backbone units within the polymeric backbone that have an angiogenesis targeting moiety conjugated thereto is herein defined as "w" and the number of free backbone units in the polymeric backbone (which are not bound to an additional moiety) is herein defined as "x".

According to some embodiments, the conjugate described herein can be represented by the general formula I:

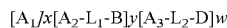  Formula I wherein:

x is an integer having a value such that x/(x+y+w) multiplied by 100 is in the range of from 0.01 to 99.9;

y is an integer having a value such that y/(x+y+w) multiplied by 100 is in the range of from 0.01 to 99.9;

w is an integer having a value such that w/(x+y+w) multiplied by 100 is in the range of from 0.01 to 99.9;

A$_1$, A$_2$ and A$_3$ are each backbone units covalently linked to one another and forming the polymeric backbone, wherein:

B is the therapeutically active agent, as described herein;

D is the angiogenesis targeting moiety, as described herein;

each of the L$_1$ and L$_2$ is independently the linker as described herein or is absent;

such that [A$_2$-L$_1$-B] is a backbone unit having attached thereto the anti-angiogenesis agent; and

[A$_3$-L$_2$-D] is a backbone unit having attached thereto the bone targeting moiety;

wherein each of the [A$_1$], the [A$_2$-L$_1$-B] and the [A$_3$-L$_2$-D] is either a terminal backbone unit being linked to one of the [A$_1$], the [A$_2$-L$_1$-B] and the [A$_3$-L$_2$-D], or is linked to at least two of the [A$_1$], the [A$_2$-L$_1$-B] and the [A$_3$-L$_2$-D] and the A$_1$, A$_2$ and/or A$_3$ are linked to one another to thereby form the polymeric backbone.

In some embodiments where the polymeric conjugate is derived from HPMA, A$_1$ is a hydroxypropylmethacrylamide unit; and A$_2$ and A$_3$ are a methacrylamide unit.

In some embodiments where the polymeric conjugate is derived from PGA, A$_1$ is a glutamate unit.

According to some embodiments, the conjugate described herein can be represented by the general formula II:

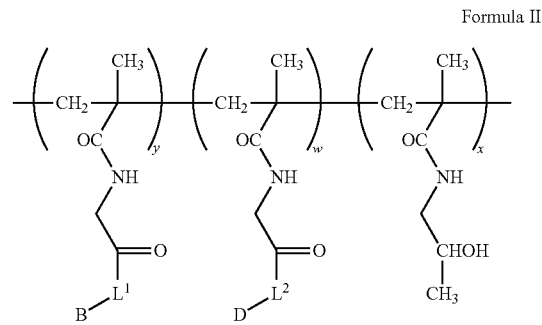

Formula II wherein B, D, L$^1$, L$^2$ and w, x, y, are as defined herein.

According to some embodiments, the conjugate described herein can be represented by the general formula III:

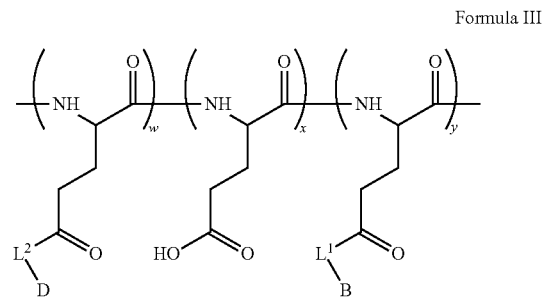

Formula III wherein B, D, L$^1$, L$^2$ and w, x, y, are as defined herein.

In some embodiments, the conjugate has the structure:

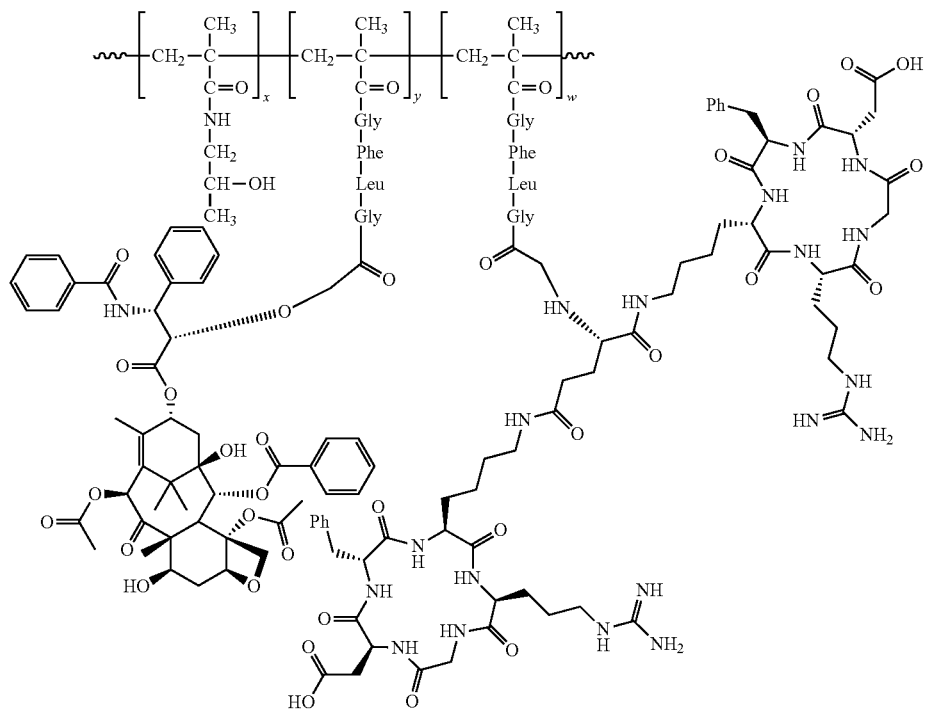

wherein w, x and y are as defined herein.
In some embodiments, the conjugate has the structure:

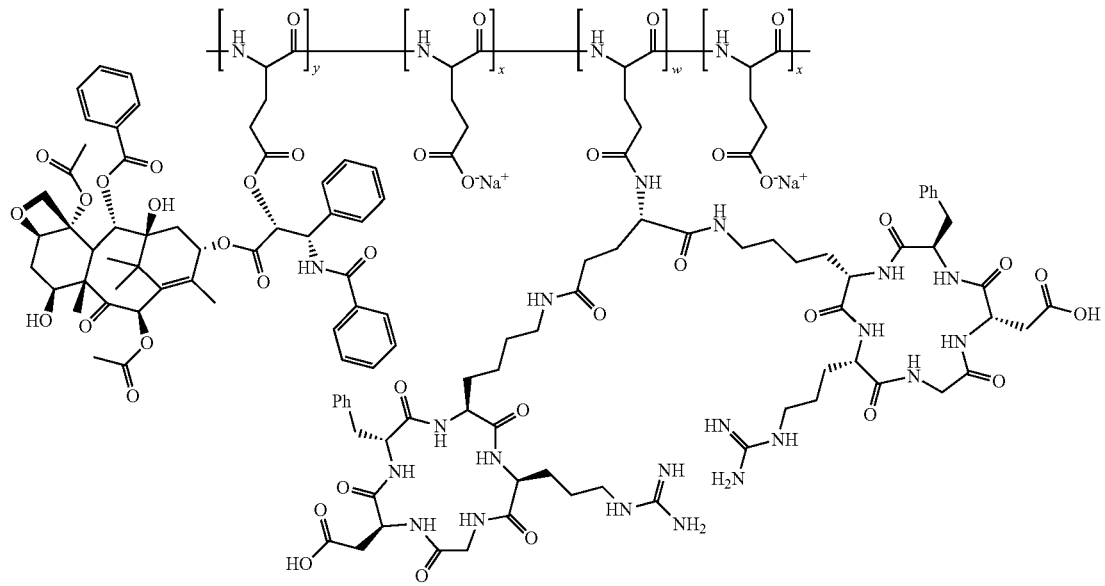

wherein w, x and y are as defined herein.

According to some embodiments of the present invention, x is an integer having a value such that x/(x+y+w) multiplied by 100 is in the range of from 70 to 99.9; y is an integer having a value such that y/(x+y+w) multiplied by 100 is in the range of from 0.01 to 15; and w is an integer having a value such that w/(x+y+w) multiplied by 100 is in the range of from 0.01 to 15.

For example x/(x+y+w) multiplied by 100 may be 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9; y/(x+y+w) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15; and w/(x+y+w) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15.

According to some embodiments, the conjugate described herein further comprises a labeling agent attached thereto.

In some embodiments, the labeling agent is attached to a portion of the backbone units that do not have the therapeutically active agent or the targeting moiety attached thereto. Optionally, the labeling agent is attached to any one of a linker, a spacer or the therapeutically active agent or the targeting moiety. The attachment of a labeling agent to the conjugate enables utilizing these conjugates for monitoring medical conditions associated with angiogenesis, for example, monitoring the therapeutic effect exhibited by the conjugate described herein.

As used herein, the phrase "labeling agent" describes a detectable moiety or a probe. Exemplary labeling agents which are suitable for use in the context of the these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$, $^{18}F$, $^{131}I$ and $^{125}I$.

The term "magnetic agent" describes a substance which is attracted to an externally applied magnetic field. These substances are commonly used as contrast media in order to improve the visibility of internal body structures in Magnetic Resonance Imaging (MRI). The most commonly used compounds for contrast enhancement are gadolinium-based. MRI contrast agents alter the relaxation times of tissues and body cavities where they are present, which, depending on the image weighting, can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

Each of the conjugates described herein may further include an additional moiety conjugated thereto. Such an additional moiety can be conjugated either to backbone units within and throughout the polymeric backbone, or be attached at one or both ends of the polymeric backbone.

Such an additional moiety can be a labeling agent, as described herein, or an additional targeting moiety or an additional therapeutically active agent, which may improve the performance of the formed conjugate. Such an additional moiety can further be a moiety that improves the solubility, bioavailability, and/or any other desired feature of the formed conjugate.

As discussed hereinabove, the conjugates described herein comprise a polymer having tumor targeting characteristics (due to the EPR effect), an angiogenesis targeting moiety and an anti-cancer agent/anti-angiogenesis agent. Therefore, the conjugates described herein are targeted to bodily sites characterized by angiogenesis and or cancer tissue. As further described hereinabove, the conjugates described herein are capable of inhibiting angiogenesis as well as cell proliferation and therefore can be utilized for the treatment of disease conditions characterized by pathologically excessive angiogenesis wherein the inhibition of angiogenesis and/or cell proliferation is beneficial.

Pathological angiogenesis has been demonstrated in several diseases, such as cancer, hypertension, rheumatoid arthritis, and diabetic retinopathy. Tumor growth and metastasis are particularly dependent on the degree of angiogenesis. Tumor angiogenesis is the proliferation of a network of blood vessels that penetrate into cancerous tumors in order to supply nutrients and oxygen and remove waste products, thus leading to tumor growth. Tumor angiogenesis involves hormonal stimulation and activation of oncogenes, expression of angiogenic growth factors, extravasation of plasma protein, deposition of a provisional extracellular matrix (ECM), degradation of ECM, and migration, proliferation and elongation of endothelial capillaries. Inhibition of further vascular expansion has therefore been the focus of active research for cancer therapy.

As demonstrated in the Examples section that follows, the conjugates described herein were able to exhibit anti-angiogenesis activity.

Thus, according to another aspect of embodiments of the invention there is provided a method of treating a medical condition associated with angiogenesis in a subject in need thereof. The method is effected by administering to the subject a therapeutically effective amount of any of the conjugates described herein.

Accordingly, according to another aspect of some embodiments of the present invention there are provided uses of the conjugates described herein as a medicament. In some embodiments, the medicament is for treating a medical condition associated with angiogenesis.

According to another aspect of some embodiments of the present invention, the conjugates described herein are identified for use in the treatment of a medical condition associated with angiogenesis.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is understood that the conjugates of the present invention may be administered in conjunction with other drugs, including other anti-cancer and anti-angiogenesis drugs. Such combinations are known in the art.

When the treatable condition is cancer the term would encompass any inhibition of tumor growth or metastasis, or any attempt to inhibit, slow or abrogate tumor growth or metastasis. The method includes killing cancer cells by non-apoptotic as well as apoptotic mechanisms of cell death.

It is noted herein that by targeting a therapeutically active agent via the methodologies described herein, the toxicity of the therapeutically active agent is substantially reduced, due to the conjugate selectivity towards sites of excessive angiogenesis. Consequently, besides the use of the conjugates described herein in a clinically evident disease, optionally in combination with other drugs, these conjugates may potentially be used as a long term-prophylactic for individuals who are at risk for relapse due to residual dormant cancers. The use of non-toxic targeted conjugates for the treatment of asymptomatic individuals who are at risk for relapse of a cancer, may lead to a major paradigm shift in cancer treatment from current methods where treatment is generally not initiated until the cancer becomes clinically evident.

The term "cancer cells" describes a group of cells which display uncontrolled growth (division beyond the normal limits).

The phrase "therapeutically effective amount" describes the amount of a compound which is sufficient to effect treatment when administered to a subject in need of such treatment or prevention. As used herein this phrase describes the amount of conjugate which is sufficient to reduce or prevent angiogenesis (i.e. inhibit the formation of new blood vessels in a tissue) and/or cell proliferation and/or kill preexisting cancer cells in tissue.

Medical conditions associated with angiogenesis and which are treatable by the conjugates described herein include, but are not limited to, atherosclerosis, cancer, hypertension, rheumatoid arthritis, diabetes and diabetes related complications such as diabetic retinopathy and macular degeneration (MD). The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

Cancers treatable by the conjugates described herein include, but are not limited to, solid, including carcinomas, and non-solid, including hematologic malignancies. Carcinomas include and are not limited adenocarcinomas and epithelial carcinomas. Hematologic malignancies include leukemias, lymphomas, and multiple myelomas. The following are non-limiting examples of the cancers treatable with the conjugates described herein: ovarian, pancreas, brain, colon, rectal, colorectal, melanoma, lung, breast, kidney, and prostate cancers.

The term "cancer metastases" describes cancer cells which have "broken away", "leaked", or "spilled" from a primary tumor, entered the lymphatic and/or blood vessels, circulated through the lymphatic system and/or bloodstream, settled down and proliferated within normal tissues elsewhere in the body thereby creating a secondary tumor.

The term "arteriosclerosis" describes a hardening of the arteries, and occurs when the normal lining of the arteries deteriorates, the walls of arteries thicken, and deposits of fat and plaque build up, causing narrowing (or even blockage) of the arteries. Atherosclerosis is the leading cause of heart attacks, heart disease and strokes. Essentially, the plaque build-up on the arterial walls becomes so significant that it begins to block the flow of blood. When vital organs, such as the heart or lungs, are deprived of oxygen rich blood, atherosclerosis becomes a life-threatening condition. Other complications of atherosclerosis are detachment of plaque build up and blood clots that travel and become lodged elsewhere in the body.

The term "diabetes" is used interchangeably with the term "diabetes mellitus" and describes a metabolic disorder of multiple etiology characterized by chronic hyperglycaemia with disturbances of carbohydrate, fat and protein metabolism resulting from defects in insulin secretion, insulin action, or both. The effects of diabetes mellitus include long-term damage, dysfunction and failure of various organs. Presently, diabetes mellitus is classified into type I and type II. The majority of patients with type I diabetes have autoimmune destruction of pancreatic beta cells as the underlying cause, have an absolute requirement for insulin therapy and will develop ketoacidosis without treatment. In type II, there is relative insulin deficiency and resistance to insulin. A causal association between glycemic control and the development and progression of the microvascular complications i.e. (retinopathy, nephropathy and neuropathy) is well-established. By virtue of microvascular involvement any tissue can be effected by diabetes.

The term "diabetes" encompasses diabetes related complications which are mainly caused by damage to blood vessels (angiopathy). Exemplary diabetes complications include, but are not limited to diabetic retinopathy (damage to the retina), which can eventually lead to blindness; diabetic neuropathy which is characterized by abnormal and decreased sensation, usually in a 'glove and stocking' distribution starting with the feet but potentially in other nerves, later often fingers and hands; diabetic nephropathy characterized by damage to the kidney which can lead to chronic renal failure; and diabetic cardiopathy which is characterized by damage to the heart leading to diastolic dysfunction and eventually heart failure.

The term "hypertension" describes a medical condition in which the blood pressure is chronically elevated. In current usage, the word "hypertension" without a qualifier normally refers to systemic, arterial hypertension. Hypertension can be classified as either essential (primary) or secondary. Essential hypertension indicates that no specific medical cause can be found to explain a patient's condition. A bout 95% of hypertension is essential hypertension. Secondary hypertension indicates that the high blood pressure is a result of (i.e., secondary to) another condition, such as kidney disease or tumors (adrenal adenoma or pheochromocytoma). Persistent hypertension is one of the risk factors for strokes, heart attacks, heart failure and arterial aneurysm, and is a leading cause of chronic renal failure.

The term "rheumatoid arthritis" describes is a chronic, systemic inflammatory disorder that may affect many tissues and organs, but principally attacks the joints producing a inflammatory synovitis that often progresses to destruction of the articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a pivotal role in its chronicity and progression.

Due to the ability of the conjugates described herein to be targeted to bodily sites characterized by angiogenesis the conjugates can be further utilized for monitoring the level of angiogenesis within a body of a patient. The method according to these embodiments of the invention is effected by administering to the subject any of the conjugates described herein, having a labeling agent attached to the polymer, as described herein, and employing an imaging technique for monitoring a distribution of the conjugate within the body or a portion thereof.

For example, the level of angiogenesis in tumor sites can serve as a measure of the size of a tumor as well as the level of metabolic activity in the tumor cells.

Other examples of disease conditions in which the monitoring of the level of angiogenesis by the conjugates described herein may be beneficial, are atherosclerosis, hypertension, rheumatoid arthritis, diabetes and diabetes related complications.

Accordingly, according to another aspect of some embodiments of the present invention there are provided uses of any of the conjugates described herein, having a labeling agent as described herein, as diagnostic agents and/or in the manufacture of a diagnostic agent for monitoring a medical condition associated with angiogenesis.

According to another aspect of some embodiments of the present invention, each of the conjugates described herein, which comprises a labeling agent, is identified for use a diagnostic agent, for monitoring a medical condition associated with angiogenesis.

Suitable imaging techniques include but are not limited to positron emission tomography (PET), gamma-scintigraphy, magnetic resonance imaging (MRI), functional magnetic resonance imaging (FMRI), magnetoencephalography (MEG), single photon emission computerized tomography (SPECT) computed axial tomography (CAT) scans, ultrasound, fluoroscopy and conventional X-ray imaging. The choice of an appropriate imaging technique depends on the nature of the labeling agent, and is within the skill in the art. For example, if the labeling agent comprises Gd ions, then the appropriate imaging technique is MRI; if the labeling agent comprises radionuclides, an appropriate imaging technique is gamma-scintigraphy; if the labeling agent comprises an ultrasound agent, ultrasound is the appropriate imaging technique, etc.

The conjugates described hereinabove may be administered or otherwise utilized in this and other aspects of the present invention, either as is, or as a pharmaceutically acceptable salt, enantiomer, diastereomer, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention. The phrase "pharmaceutically acceptable salts" is meant to encompass salts of the active compounds which are prepared with relatively nontoxic acids or bases, depending on the particular substituents found on the compounds described herein. When conjugates of the present invention contain relatively acidic functionalities, base addition salts can be obtained by contacting the neutral (i.e., non-ionized) form of such conjugates with a sufficient amount of the desired base, either neat or in a suitable inert solvent. Examples of pharmaceutically acceptable base addition salts include sodium, potassium, calcium, ammonium, organic amino, or magnesium salt, or a similar salt. When conjugates of the present invention contain relatively basic functionalities, acid addition salts can be obtained by contacting the neutral form of such conjugates with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific conjugates of the present invention contain both basic and acidic functionalities that allow the conjugates to be converted into either base or acid addition salts.

The neutral forms of the conjugates are preferably regenerated by contacting the salt with a base or acid and isolating the parent conjugate in a conventional manner. The parent form of the conjugate differs from the various salt forms in certain physical properties, such as solubility in polar solvents, but otherwise the salts are equivalent to the parent form of the conjugate for the purposes of the present invention.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

The conjugates described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The conjugates described herein can exist in unsolvated forms as well as solvated forms, including hydrated forms. In general, the solvated forms are equivalent to unsolvated forms and are encompassed within the scope of the present invention. Certain conjugates of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

According to another aspect of embodiments of the invention there is provided a pharmaceutical composition comprising, as an active ingredient, any of the conjugates described herein and a pharmaceutically acceptable carrier Accordingly, in any of the methods and uses described herein, any of the conjugates described herein can be provided to an individual either per se, or as part of a pharmaceutical composition where it is mixed with a pharmaceutically acceptable carrier.

As used herein a "pharmaceutical composition" refers to a preparation of one or more of the conjugates described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described hereinabove is packaged in a packaging material and identified in print, in or on the packaging material, for use in the treatment of a medical condition associated with angiogenesis.

According to another embodiment of the present invention, the pharmaceutical composition is packaged in a packaging material and identified in print, in or on the packaging material, for use in monitoring a medical condition associated with angiogenesis.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

While reducing the present invention to practice, the present inventors have designed and successfully practiced a novel process for conjugating to polymer a therapeutically active agent, an angiogenesis targeting moiety and optionally a labeling agent. It is noted that synthesizing such a polymeric conjugate is subjected to various limitations, imposed by a different solubility of the moieties to be conjugates, complicated desired structural features that are required for optimal performance of the conjugate, incompatibility of the reactants, and the like. Hence, devising a process that overcomes these limitations and is designed to obtain a conjugate that exhibits at least a reasonable performance, is highly advantageous.

According to another aspect of embodiments of the invention, there is provided a process of preparing the conjugates described herein. The process is effected by:

(a) co-polymerizing a plurality of monomeric units that form the polymeric backbone, at least one of the monomeric units terminating by a first reactive group, and at least one of the monomeric units terminating by a second reactive group, to thereby obtain a co-polymer that comprises a plurality of backbone units, at least one backbone unit having the first reactive group and at least one backbone unit having the second reactive group, said first reactive group being capable of reacting with the angiogenesis targeting moiety and the second reactive being capable of reacting with the therapeutically active agent;

(b) reacting the co-polymer with the angiogenesis targeting moiety or a derivative thereof, via the first reactive group, to thereby obtain a copolymer having the angiogenesis targeting moiety attached to a polymeric backbone thereof; and (c) further reacting the co-polymer with the therapeutically active agent or a derivative thereof, via the second reactive group, to thereby obtain the co-polymer having the therapeutically active agent attached to a polymeric backbone thereof, thereby obtaining the conjugate.

In some embodiment, (b) is performed subsequent to, concomitant with or prior to (c). Thus, the process may be effected such that the therapeutically active agent is first reacted with the functionalized polymeric backbone, thereby obtaining the polymeric backbone having the therapeutically active agent attached thereto and then the angiogenesis targeting moiety is reacted with the functionalized polymeric backbone thereby obtaining the conjugate.

The copolymerization can be effected by any polymerization method known in the art.

In some embodiments, the at least one monomeric unit that terminates with the first reactive group comprises a first plurality of the monomeric units.

In some embodiments, the at least one monomeric unit that terminates with the second reactive group comprises a second plurality of the monomeric units.

The monomeric units described herein, which terminate by a reactive group, are also referred to herein as functionalized monomers or functionalized monomeric units.

The co-polymer formed by the co-polymerization is also referred to herein as a functionalized co-polymer or a functionalized polymeric backbone.

In some embodiments, the co-polymerization can be effected in the presence of monomeric units which form the polymeric backbone, and which are non-functionalized.

Each of the first and second reactive groups can be protected prior to the respective conjugation thereto. In such cases, the process further comprises deprotecting the reactive group prior to the respective conjugation.

This allows a regio-controlled conjugation of, for example, the therapeutically active agent to those backbone units that comprises a biodegradable linker.

As used herein, a "reactive group" describes a chemical group that is capable of reacting with another group so as to form a chemical bond, typically a covalent bond. Optionally, an ionic or coordinative bond is formed.

A reactive group is termed as such if being chemically compatible with a reactive group of an agent or moiety that should be desirably attached thereto. For example, a carboxylic group is a reactive group suitable for conjugating an agent or a moiety that terminates with an amine group, and vice versa.

Other exemplary reactive groups include, but are not limited to, hydroxy, nitro, halo, haloalkyl, carboxylates, thiol, thiocarboxylates, and the like.

A reactive group can be inherently present in the monomeric units of the polymer and/or angiogenesis targeting moiety and the therapeutically active agent, or be generated therewithin by terms of chemical modifications of the chemical groups thereon or by means of attaching to these chemical groups a spacer or a linker that terminates with the desired reactive group.

A discussed hereinabove, the conjugates described herein are designed so as to release the therapeutically active agent and angiogenesis targeting moiety in the desired bodily site (i.e. sites of extensive angiogenesis). Thus, the therapeutically active agent and angiogenesis targeting moiety are linked to the polymer via a direct linkage or via an indirect linkage, through a linker group, whereby, in some embodiments, the direct/indirect linkage is designed as being cleavable at conditions characterizing the desired bodily site (e.g., by certain enzymes or pH).

For example, when the polymer is polyglutamic acid (PGA), the process may include the attachment of the therapeutically active agent and angiogenesis targeting moiety directly to the carboxylic groups of the glutamate amino acids.

Alternatively, the process may include the use of a linker as described herein whereby the linker is attached to the monomeric units, prior to co-polymerizing, so as to obtain a polymeric backbone in which a portion of the backbone units have the linker attached thereto. Further alternatively, the linker can be attached to the reactive groups in the functionalized polymeric backbone. Optionally, the linkers may be attached first to the therapeutically active agent and/or the angiogenesis targeting moiety and then be attached to the respective reactive group in the functionalized polymeric backbone. The linker attaching the therapeutically active agent and the linker attaching the angiogenesis targeting moiety may be the same or different.

Hence, in some embodiments, the process described herein, is such that at least one of the monomer unit of (a) comprises a linker as described herein, wherein the linker terminates with a reactive group and wherein the angiogenesis targeting moiety is linked to the polymer via the linker.

In some embodiments, the process described herein, is such that at least one of the monomer unit of (a) comprises a linker as described herein wherein the linker terminates with a reactive group and wherein the therapeutically active agent is linked to the polymer via the linker. Preferably, the process described herein, is such that the angiogenesis targeting moiety is also linked to the polymer via the linker as described herein.

Optionally, the process may include attachment of a spacer as described herein to the backbone units of the polymer and then to therapeutically active agent and/or angiogenesis targeting moiety. Alternatively, the spacer may be attached first to the therapeutically active agent and/or to the angiogenesis targeting moiety and then to the polymer.

Thus, in the case of the polymer being PGA, the process may be effected, for example, by the attachment of a spacer (such as, for example, $NH_2(CH_2)_2NH_2$) to the therapeutically active agent and/or angiogenesis targeting moiety followed by attaching the spacer to the carboxylic groups of the glutamate amino acids (for example, by attaching the amine group of the spacer to the carboxylic group of the PGA thereby obtaining an amide bond).

It should be appreciated that the spacers and linkers utilized for coupling the therapeutically active agent and/or the angiogenesis targeting moiety to the polymer are designed so as to allow a smooth and efficient conjugation of the respective moiety and an optimal performance of the obtained conjugate, as discussed elaborately hereinabove.

In the case of the polymer and/or the therapeutically active agent and/or the angiogenesis targeting moiety further comprising a linker the process of synthesis may include attaching the spacer to the linker moiety rather than directly to polymer/agent/moiety comprising the linker.

Generally, the therapeutically active agent or angiogenesis targeting moiety can be attached to the monomeric units of the polymer, or to the backbone units of the copolymer, by means of a functional group that is already present in the native molecule and/or the backbone units of the polymer or otherwise can be introduced by well-known procedures in synthetic organic chemistry without altering the activity of the agent. For example, the angiogenesis targeting moiety and the therapeutically active agent can be attached to the polymer via an amide bond between the terminal carboxylic group of a peptidic linker and an amine group located in the angiogenesis targeting moiety and/or the therapeutically active agent.

In some embodiments the process further comprises attaching a labeling agent, as defined herein, to the formed conjugate. The labeling agent can be attached to either of functionalized monomeric units, prior to co-polymerization or to the formed co-polymer.

In some embodiments, the labeling agent is attached to the co-polymer concomitantly with the angiogenesis targeting moiety. Alternatively, it is attached prior to or subsequent to attaching the angiogenesis targeting moiety and/or the therapeutically active agent.

In some embodiments, the process comprises co-polymerizing, along with the functionalized and non-functionalized monomeric units described herein, monomeric units terminating with a third reactive group, the third reactive group being for conjugating thereto a labeling agent or any other additional moiety, as described herein.

Thus, each of the conjugates described in any of the embodiments of the invention, may further include an additional moiety conjugated thereto. Such an additional moiety can be conjugated either to monomeric units within and throughout the polymeric backbone, or be attached at one or both ends of the polymeric backbone.

Such an additional moiety can be a labeling agent, as described herein, or an additional targeting moiety or an additional therapeutically active agent, which may improve the performance of the formed conjugate. Such an additional moiety can further be a moiety that improves the solubility, bioavailability and/or any other desired feature of the formed conjugate As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Materials and Methods

General:

All reactions requiring anhydrous conditions were performed under an argon or nitrogen atmosphere.

Chemicals and solvents are either A.R. grade or purified by standard techniques.

Thin layer chromatography (TLC): silica gel plates Merck 60 $F_{254}$; compounds were visualized by irradiation with UV light and/or by treatment with a solution of phosphomolybdic acid (20% wt. in ethanol) or ninhydrine (10% wt. ethanol), followed by heating.

Size Exclusion chromatography (SEC): Shephadex G25 resin, eluent $H_2O$. SEC analysis was performed using a Viscotek TDA™ detector system, with two TSK-gel columns in series (G3000 PWXL and G2500 PWXL) and a guard column (PWXL Guardcol). A flow rate of 0.8 ml/min, and a mobile phase 0.1 M PBS buffer was used. Viscotek Instrument software was employed for data analysis. HPLC was performed using Merck Hitachi L-2130 HPLC pump and L-2200 autosampler with a Lichrospher® 100 C18 (150×3.9 mm) column, and as mobile phase different acetonitrile gradients in aqueous 0.1% TFA. The UV spectra were recorded on a Jasco V-530 UV/Vis spectrophotometer.

Flash chromatography (FC): silica gel Merck 60 (particle size 0.040-0.063 mm), eluent given in parentheses.

$^1$H NMR: Bruker AMX 200 or 400 instrument. The chemical shifts are expressed in δ relative to TMS (δ=0 ppm) and the coupling constants J in Hz. The spectra are recorded in $CDCl_3$, as a solvent at room temp.

400 Mesh copper grid SPI Supplies, West Chester, Pa.

All chemical reagents including N,N-Diisopropylcarbodiimide (DIC), 1-hydroxybenzotriazol (HOBt), di-isopropylethylamine (DIEA), N-hydroxysuccinimide (OHSuc), N,N'-dimethylaminopyridine (DMAP) and anhydrous dimethylformamide (DMF) were purchased from Sigma-Aldrich Química S.A. (Madrid, Spain) and used without further purification.

All solvents were of HPLC grade and were obtained from Merck (Barcelona, Spain). Paclitaxel was purchased from Petrus Chemicals and Materials Ltd (Israel). E-[c(RGDfk)$_2$] (SEQ ID NO: 26) and c(RADfk) (SEQ ID NO:40) were purchased from Peptides International, Louisville, Ky., USA. c(RGDfk) (SEQ ID NO:9) was obtained from Matthias Barz and Prof. Dr. R. Zentel (University of Mainz, Germany). Fibronectin was purchased from Biological Industries Ltd (Beit Haemek, Israel). Fibrinogen was from Sigma-Aldrich (Israel). Fluorescence dye Oregon green cadaverine was from Molecular Probes. All other reagents were of general laboratory grade and were purchased from Merck unless otherwise stated.

Anti-ERK1/2 MAPK, P-ERK1/2 MAPK, AKT and P-AKT$^{Ser473}$ antibodies are purchased from Cell Signaling Technology Ltd. Bax, anti-cleaved PARP, caspase-3 and caspase-9 are purchased from Cell Signaling Technology Ltd.

Ethics Statement:

All animal procedures were performed in compliance with Tel Aviv University, Sackler School of Medicine guidelines and protocols approved by the Institutional Animal Care and Use Committee. Body weight and tumor size were measured three times a week.

Cell Culture:

U87 human glioblastoma and MG-63-Ras human osteosarcoma cells were obtained from the American Type Culture Collection (ATCC # HTB-14). MG-63-Ras cells were transfected with activated ras (MG-63-Ras) as previously described [Segal, et al 2009 PLoS ONE, 4: e5233,] in order to generate an in vivo fast-growing tumor cell line. mCherry-labeled MG-63-Ras human osteosarcoma cell line and mCherry-labeled U87 human glioblastoma were obtained by infection with a pQC-mCherry retroviral vector as previously described [Segal et al. 2009, PloS ONE 4:e5233]. The infected cells were selected for stable expression of mCherry using puromycin.

PANC02 murine pancreatic tumor cells were established by Corbett et al. Cancer Res. 1984 44: 717-726 and were cultured in Dulbecco's modified Eagle's medium (DMEM) supplemented with 10% fetal bovine serum (FBS), 100 mg/ml Penicillin, 100 U/ml Streptomycin, 12.5 U/ml Nystatin, 2 mM L-glutamin, 1 mM Sodium Pyruvate and MEM-EAGLE non-essential amino acids (Biological Industries, Israel).

Human umbilical vein endothelial cells (HUVEC) were purchased from Lonza, Switzerland. Cells were cultured in Endothelial Growth Medium-2 (EGM-2) (Cambrex, USA). MCF7/Cyr61 cells were cultured in Dulbecco's modified Eagles' Medium (DMEM) supplemented with 10% Fetal Bovine Serum (FBS).

All cells were grown at 37° C.; 5% $CO_2$.

Luciferase Infection of MCF7/Cyr61 Cell Line:

In order to generate a stable luciferase-expressing MCF-7/Cyr61 cell line (overexpressing the protein CYR61 and having Paclitaxel-resistance), MCF7/Cyr61 cells are transfected with a pBabe retroviral vector carrying the firefly luciferase gene and tested both in vitro and in vivo using a Biospace Photon Imager following the bioluminescence in a whole animal imaging system. For comparison, control MCF-7 cells not expressing CYR61 and thus not having Paclitaxel-resistance, are also transfected with the firefly luciferase gene or mCherry.

Western Blot:

For evaluation of the level of expression of proteins, cells are harvested with Phosphate Buffered Saline (PBS containing 0.25 mM EDTA and lysed in 20 mM Tris, 150 mM NaCl, 1% Triton X-100, pH 7.5, supplemented with protease inhibitors (Complete™ solution, Boehringer-Manheim) and 2 mM $Na_3VO_4$. The cell debris is pelleted and the protein concentration determined in the supernatant using the BCA reagent (Pierce). Proteins are separated by SDS-PAGE, transferred to a nitrocellulose membrane, and immunoblotted for 2 hours with the relevant primary antibodies. Following Tris-Buffered Saline Tween (TBS-T) washes, peroxidase-conjugated IgG (Jackson) is added, the membrane washed again with TBS-T and immunoreactive bands are detected by West Pico Chemiluminescent Substrate (Pierce).

Flow Cytometry Analysis:

For evaluation of the level of apoptosis in a cell culture, following different treatments with PGA copolymer-c(RGDfk)$_2$-Paclitaxel (SEQ ID NO:18) and HPMA copolymer-c(RGDfk)$_2$-Paclitaxel (SEQ ID NO:23), representative conjugates according to the embodiments of the present invention, cells are harvested, fixed with methanol, and re-suspended in PBS. The fluorescent marker, Propidium iodide (50 µg/ml) is added for nuclear staining and the cells are analyzed in a fluorescence-activated cell sorter (FACS unit, Inter-departmental Facilities, Faculty of Medicine, Tel Aviv University).

Cell Proliferation Assay:

The anti-angiogenesis and anti-proliferative activity of the conjugates described herein was evaluated by the effect of the conjugates on the proliferation of HUVEC, U87 and PANC02 cells.

HUVEC were plated onto 24-well plate ($1 \times 10^4$ cells/well) in endothelial cell basal medium 2 (EBM-2; Cambrex, USA) supplemented with 5% fetal bovine serum (FBS). Following 24 hours of incubation (37° C.; 5% $CO_2$) medium was replaced with Endothelial cell growth medium-2 (EGM-2; Cambrex, USA). U87 and PANC02 cells were plated onto 96 well plate ($2 \times 10^3$ cells/well) in DMEM supplemented with 5% FBS and incubated for 24 hours (37° C.; 5% $CO_2$). Following 24 hours of incubation the medium was replaced with DMEM containing 10% FBS. Cells were challenged with the tested compounds at serial concentrations for 72 hours. After incubation the number of HUVEC were counted by Coulter Counter and U87, and PANC02 cells were counted by XTT respectively.

$\alpha v\beta 3$ Expression Detection:

HUVEC, U87 and Panc02 were harvested with PBS containing 2.5 mM EDTA, followed by re-suspension of the cells in serum free medium (EBM-2 for HUVEC and DMEM for U87 and Panc02) and incubation for 30 minutes. The cells were divided and further re-suspended in PBS containing $Mg^{2+}$ and $Ca^{2+}$. The cells were then incubated together with the primary antibody MAB1976-anti $\alpha v\beta_3$ integrin (Chemicon, 1:20) for 30 minutes, at room temperature, in gentle rocking. Serving as control were cells not incubated with any antibody. Then, the cells were washed and re-suspended in PBS with the second antibody anti mouse-FITC (Jackson, 1:50) and incubated in the dark for 30 minutes, at room temperature, in gentle rocking. The cells ($1 \times 10^5$) were collected by Fluorescence-activated cell sorter (FACS), and statistical analysis was performed using WinMDI software.

$\alpha v\beta 3$ Interaction with Fluorescently Labeled Conjugates:

A fluorescence probe, Oregon Green-cadaverine (OG), was conjugated to PGA conjugates through the free carboxylic groups (see Example 5 for synthesis description), in order to study the cellular uptake and trafficking.

HUVEC were plated onto 6 mm plates ($5 \times 10^5$ cells/plate) in EBM-2 (Cambrex, USA) supplemented with 5% FBS. Following 24 hours of incubation (37° C.; 5% $CO_2$), cells were challenged with either PGA-OG, PGA-c(RADfk)-OG (SEQ ID NO: 24) or PGA-E-[c(RGDfk)$_2$]-OG (SEQ ID NO:25) diluted in EGM-2 medium for 5, 10, 15, 30 or 60 minutes. Cells were then washed in PBS (×3), harvested with PBS containing 2.5 mM EDTA and analyzed with the ImageStream 100 imaging flow cytometer (Amnis). Analysis was performed using IDEAS software.

Capillary-Like Tube Formation Assay:

The anti-angiogenesis activity of the conjugates was evaluated by the effect of the conjugates on the ability of HUVEC cells to form capillary-like tube structures.

The surface of 24-well plates was coated with Matrigel matrix (50 µl/well) (BD Biosciences, USA) on ice and was then allowed to polymerize at 37° C. for 30 minutes. HUVEC ($3 \times 10^4$ cells) were challenged with the tested compounds, and were seeded on coated plates in the presence of complete EGM-2 medium. After 8 hours of incubation (37° C.; 5% $CO_2$), wells were imaged using Nikon TE2000E inverted microscope integrated with Nikon DS5 cooled CCD camera by 4× objective, brightfield technique. During the tube formation assay endothelial cells directionally migrate to align, branch and form polygonal networks (i.e. tube like structures). The extent of capillary-like tube structures is inversely proportional to the anti-angiogenesis activity of the compounds.

Migration Assay:

The anti-angiogenesis activity of the conjugates was evaluated by examining the effect of the conjugates on the ability of HUVEC to migrate toward the Vascular Endothelial Growth Factor (VEGF).

Cell migration assay was performed using modified 8 µm Boyden chambers Transwells® (Costar Inc., USA) coated with 10 µg/ml fibronectin HUVEC ($15 \times 10^4$ cells/100 µl) were challenged with the tested compounds that were added to the upper chamber of the transwells for 2 hours. Following incubation, cells were allowed to migrate to the underside of the chamber for 4 hours in the presence or absence of VEGF (20 ng/ml) in the lower chamber. Cells were then fixed and stained (Hema 3 Stain System; Fisher Diagnostics, USA). The stained migrated cells were imaged using Nikon TE2000E inverted microscope integrated with Nikon DS5 cooled CCD camera by 10× objective, brightfield illumination. Migrated cells from the captured images per membrane were counted using NIH image software. Migration was normalized to the percent of migration toward VEGF of HUVEC which were not incubated with any compound. The extent of migration is inversely proportional to the anti-angiogenesis activity of the compounds.

Endothelial Cell Adhesion Assay:

The ability of E-[c(RGDfk)$_2$] and E-c(RGDfk) moieties (SEQ ID NOs: 2 and 41) in the conjugates to inhibit endothelial attachment to cellular matrix after conjugation, was assessed using an adhesion assay. Flat bottom 96-well culture plates (Nunc, Denmark) were coated with 0.5 µg/well fibrinogen overnight at 4° C. After washing three times with Phosphate buffered saline (PBS), the wells were blocked with 1% bovine serum albumin (BSA) for 1 hour at 37° C. and washed three times again with PBS. HUVEC were harvested in phosphate-buffered saline (137 mM NaCl, 2.7 mM KCl, 4.3 mM Na2HPO4, 1.4 mM $KH_2PO_4$, pH 7.3) with 2.5 mM EDTA and resuspended in EBM-2 serum-free media (Clonetics). HUVEC were incubated for 30 minutes, at room temperature, with the tested compounds. The treated HUVEC were plated at $5 \times 10^4$ cells per well and were allowed to attach for 1 hour at 37° C. After incubation, the unattached cells were removed by rinsing the wells with PBS. The attached cells were fixed with 3.7% formaldehyde, stained with 0.5% crystal violet and were imaged using Nikon TE2000E inverted microscope integrated with Nikon DS5 cooled CCD camera by 4× objective, brightfield technique. The number of attached cells was quantified with NIH ImageJ processing and analysis software. Non-specific binding was determined by adhesion of HUVEC cells, which were not incubated with any of the tested compounds, to BSA-coated plates.

Determination of % of Free Paclitaxel and Free Peptide in the Conjugates Synthesized:

In order to determine the free Paclitaxel (PTX) and free peptide [either c(RGDfk)$_2$ (SEQ ID NO: 26) or c(RGDfk) (SEQ ID NO: 9) or control free c(RADfk)] (SEQ ID NO:40) content in the conjugates synthesized, aqueous solutions of the conjugates (1 mg/ml) were prepared, and an aliquot (100 µl) from each conjugate solution was added to a polypropylene tube followed by the addition of water up to a volume of 1 ml. Then, 5 ml of $CHCl_3$ and 2-propanol at a ratio of 4:1 was added and the aliquot samples were thoroughly extracted by vortexing ($3 \times 10$ seconds). The upper aqueous layer was carefully removed and the solvent evaporated under $N_2$. The dry residue was dissolved in 200 µl of HPLC grade methanol.

A similar procedure was carried out for the free compound (PTX or peptide) (in which case a aliquots of 200 µl from a 1 mg/ml solution of the compounds was added to polypropylene tubes). Addition of 1 ml of MeOH to redissolve the product gave a 200 µg/ml stock from which a range of concentrations was prepared (2 to 100 µg/ml).

Alternatively, the aliquot of the conjugates solution as well as the free compound solution were purified by a pre-made RP column with a C18 Porous 50 resin using a mixture of MeOH:AcCN as the eluents. The solvent was then evaporated under $N_{2(g)}$. The dry residue was then dissolved in 200 µl of HPLC grade methanol.

The free amount of drug in the conjugates was determined by HPLC using a Lichrospher® C18 (150×3.9 mm) column. Flow rate of 1 ml/min using an acetonitrile gradient in aqueous 0.1% TFA (to simultaneously determine PTX and the peptide, a gradient from 10% to 90% of acetonitrile in 28 min was used). The retention time was r.t.=16.9 minutes for PTX, r.t.=8.0 minutes for E-[c(RGDfk)$_2$] (SEQ ID NO: 2) and r.t.=5.3 minutes for c(RADfk) (SEQ ID NO:40) and r.t.=5.7 minutes for c(RGDfk) (SEQ ID NO: 9) ($\lambda$=220 nm).

Quantitative Evaluation of PGA Conjugates Hydrodynamic Diameter and Size Distribution:

The mean hydrodynamic diameter of the PGA conjugates was evaluated using a real time particle analyzer (NanoSight LM20™) containing a solid-state, single mode laser diode (<20 mW, 655 nm) configured to launch a finely focused beam through a 500 µl sample chamber. The tested conjugate was dissolved in PBS to a final concentrations of 9.9 mg/ml. The samples were then injected into the chamber by syringe and allowed to equilibrate to a unit temperature (23° C.) for 30 seconds. The particles dynamics were visualized at 30 frames per second (fps) for 60 seconds at 640×480 resolution by the device CCD camera. The paths the particles take under Brownian motion over time were analyzed using Nanoparticle Tracking Analysis (NTA) software. The diffusion coefficient and hence sphere equivalent hydrodynamic radius of each particle was separately determined and the particle size distribution profiles were generated. Each sample was measured three times in triplicates, and the results represent the mean diameter.

Release of PTX from PGA Copolymer -E-c(RGDfk)$_2$-Paclitaxel Conjugate (SEQ ID NO:18) in the Presence of Cathepsin B:

The ability of Cathepsin B to cleave and therefore release PTX from PGA copolymer-E-c(RGDfk)$_2$-PTX (SEQ ID NO:18) was assessed as follows:

Cathepsin B (5 U) was added last to a 1 ml solutions containing 3 mg of the tested conjugates and 20 mM sodium acetate, 2 mM EDTA and 5 mM DTT at a pH of 6 and at a temperature of 37° C. Solutions containing free PGA polymer and free PTX served as control. Sample aliquots (100 µl) were taken at various time points up to 72 hours, frozen and stored in liquid nitrogen, until assayed by HPLC (by Porous50 resin) and/or by Gel permeation chromatography (GPC; direct analysis of 50 µl aliquots). PGA polymer incubated in buffer alone (without addition of cathepsin B) served as an additional control to assess non-enzymatic hydrolytic cleavage. The amount of free PTX released from the tested compounds was assessed by HPLC (X=220 nm). Doxycycline was used as internal standard in all cases. In addition, an LC-MS analysis of the released compounds was also carried out to in order determine the major metabolites released. The MW of the conjugates was determined by diluting 50 μl aliquots of the conjugate containing solution to a final volume of 200 μl with PBS buffer and subjecting the aliquots to GPC analysis (Viscotek TDA detector).

Stability of the Conjugates in Plasma:

Stability in plasma was assessed by incubating each of the conjugates (3 mg/ml), for 24 hours, at 37° C., in plasma freshly extracted from Wistar rats. At various time points, samples of 100 μl were collected. 15 μl of 0.2 mg/ml solution of doxycycline in MeOH served as an internal standard, and 135 μl of a mixture of MeCN:MeOH 50:50 with 2% $ZnSO_4$ were added to each sample in order to precipitate serum proteins. The samples were centrifuged at 14000 rpm for 5 minutes, and 150 μl of the supernatant were subjected to analysis by HPLC as described hereinabove. The amount of PTX release from the conjugates in the presence of serum was determined to be insignificant.

αvβ3 Interaction with E-[c(RGDfk)$_2$] In Vivo:

SCID male were inoculated s.c. with 2×10$^6$ mCherry-labeled U87 human osteosarcoma or with 5×10$^6$ mCherry-labeled MG-63 human osteosarcoma. Mice bearing an average volume of 175 mm$^3$ U87 human osteosarcoma tumors were injected i.v. with PGA-E-[c(RGDfk)$_2$]-OG (SEQ ID NO: 25; 50 μM-RGD) or PGA-c(RADfk)-OG (SEQ ID NO: 24; 50 μM-RGD-equivalent dose) (n=3 mice/group). One hour after injection, tumors were removed, dissected to thin slices and examined under Zeiss Meta LSM 510 confocal imaging system.

Mice bearing 600 mm$^3$ MG-63 human osteosarcoma tumors were injected i.v. with PGA-PTX-E-[c(RGDfk)$_2$]-OG (SEQ ID NO: 25; 50 μM-RGD), PGA-PTX-OG or PGA-PTX-c(RADfk)-OG (SEQ ID NO: 24; 50 μM-RGD-equivalent dose) (n=3 mice/group). 30 and 60 min after injection, tumors were removed washed several times with cold PBS, fixed with 3.5% paraformaldehyde for 15 minutes at RT and washed with PBS again.

Tumors were then homogenized and analyzed with the ImageStream 100 (amnis). Analysis was performed using IDEAS software.

Confocal Microscopy:

Cellular colocalization of OG labeled PGA-E-[c(RGDfk)$_2$] (SEQ ID NO: 25) conjugate was monitored utilizing a Zeiss Meta LSM 510 confocal imaging systems with 40 oil objectives. All images were taken using a multi-track channel acquisition to prevent emission cross-talk between fluorescent dyes. Single XY, XZ plane-images were acquired in 1024×1024 resolution.

Statistical Methods:

Data are expressed as mean±SD. Statistical significance was determent using an unpaired t-test. P<0.05 was considered statistically significant. All statistical tests are two-sided.

Example 1

Synthesis of HPMA Copolymer-E-c(RGDfk)$_2$-Paclitaxel (SEQ ID NO: 23)

The general synthesis of an HPMA copolymer-c(RGDfk)$_2$-Paclitaxel (SEQ ID NO:23) (Compound 2) is depicted in FIG. 6.

As shown in FIG. 6, the HPMA-c(RGDfk)$_2$-Paclitaxel conjugate (SEQ ID NO:23) is prepared in a two-step synthesis, as follows: The peptide linker, Gly-Phe-Leu-Gly (SEQ ID NO:10) is a cathepsin B-cleavable linker. Cathepsin B is a lysosomal enzyme overexpressed in both epithelial and endothelial tumor cells. First, the conjugation of c(RDGfk)$_2$ (SEQ ID NO:26) to HPMA copolymer-Gly-Phe-Leu-Gly (SEQ ID NO:42) by non-specific aminolysis using the amino group of the lysine is effected. Next, the conjugation of Paclitaxel to the polymer through an ester bond is effected. HPMA copolymer-Gly-Phe-Leu-Gly (GFLG 10 mol %)-p-nitrophenol (ONp) (SEQ ID NO:43) is used as multivalent polymeric precursor, therefore a maximum of 10 mol % functionalization is allowed. In order to keep an appropriate Paclitaxel loading a maximum of 5 mol %, c(RDGfk)$_2$ (SEQ ID NO:26) loading is considered.

Synthesis of HPMA-E-c(RDGfk)$_2$ (SEQ ID NO:44) (Compound 1)

HPMA copolymer-Gly-Phe-Leu-Gly-ONp (SEQ ID NO:43) is dissolved in anhydrous Dimethylformamide (DMF) under nitrogen atmosphere. c(RDGfk)$_2$ (SEQ ID NO:26) is conjugated through aminolysis to the HPMA copolymer-Gly-Phe-Leu-Gly-ONp (SEQ ID NO:43) in DMF and then mixed together. c(RDGfk)$_2$.TFA (SEQ ID NO 45) in anhydrous DMF is then added together with TEA. The reaction is allowed to proceed for 8 hours at room temperature. TLC is used to monitor the reaction. The solvent is thereafter removed under high vacuum and the conjugate is purified by size exclusion chromatography (SEC), Sephadex LH-20 using methanol as mobile phase. For further purification, the conjugate is redissolved in a minimum amount of water, dialyzed and lyophilized yielding the desired compound 1 in a high percentage of purity. UV spectroscopy is used to determine the peptide content of the conjugate. In order to characterize the c(RDGfk)$_2$ loading (SEQ ID NO: 26) on the conjugates a calibration curve is carried out in DMF RT=25° C., at a maximum Absorbance of 266 nm.

Synthesis of HPMA-Copolymer-E-c(RDGfk)$_2$-Paclitaxel (SEQ ID NO:23) (Compound 2)

Paclitaxel is dissolved in DMF and added to the HPMA-c(RDGfk)$_2$ conjugate (SEQ ID NO:44) dissolved in DMF as well. The conjugate is re-purified, lyophilized and characterized by HPLC analysis at 254 nm.

The conjugate HPMA copolymer-TNP-470-RGD4C (SEQ ID NO:46) is similarly prepared.

Example 2

Synthesis and Characterization of a PGA Copolymer-E-c(RGDfk)$_2$-Paclitaxel Conjugate (SEQ ID NO:18)

Synthesis of PGA-Copolymer-E-c(RGDfk)$_2$-Paclitaxel Conjugate (SEQ ID NO:18)

The general synthesis of a PGA-E-[c(RGDfK)$_2$]-Paclitaxel (SEQ ID NO:18) (Compound 4) is depicted in FIG. 7. The ester linker is hydrolytically labile and PTX release is expected to occur under lysosomal acidic pH. The PGA-E-[c(RDGfk)$_2$]-Paclitaxel conjugate (SEQ ID NO:18) was prepared in two steps: first, the PTX was conjugated to the PGA polymer followed by the conjugation of the -E-[c(RDGfk)$_2$] peptide (SEQ ID NO:2) to the PTX-conjugated polymer. The ester linker between the carboxylic groups of the glutamate monomeric units and the PTX as well as the [c(RDGfk)$_2$] (SEQ ID NO: 26) are hydrolytically labile and under lysosomal acidic pH are cleaved thus releasing both PTX and -E-[c(RDGfk)$_2$] (SEQ ID NO:2). The peptide linkage between the glutamate monomeric units is a hydrolytically labile linker, which is also susceptible to cathepsin B-cleavage. The E-[c(RGDfK)$_2$] peptide (SEQ ID NO:2) was conjugated to the PTX containing polymer through a glutamic acid (-E-) peptidic linker.

PGA was used as a multivalent polymeric precursor. The starting PGA was synthesized via N-Carboxyanhydride (NCA) polymerization of glutamic acid. Transition metal macroinitiators were used in order to overcome the well-known limitations of conventional NCA polymerizations such as the presence side-reactions that restrict control over MW and prohibit formation of well-defined block copolymers. The synthetic method was performed as previously described [Curtin et al. 1999, *Journal of the American Chemical Society* 121: 7427-7428].

Synthesis of a PGA-Paclitaxel Conjugate (Compound 3)

PTX was conjugated to the PGA (Mw 18,200, Mw/Mn 1.4) by carbodiimide coupling. The reaction was allowed to proceed at room temperature for 24 hours. Thin layer chromatography (TLC, silica) showed a complete conversion of the free PTX ($R_f$=0.6) to the PTX-polymer conjugate (Compound 3) ($R_f$=0, CH$_2$Cl$_2$/MeOH=90:10). The reaction was allowed to proceed at room temperature for 24 hours without product isolation.

Synthesis of PGA-Copolymer -E-c(RGDfk)$_2$-Paclitaxel (SEQ ID NO: 18) (Compound 4)

Following the completion of the PTX conjugation reaction N-hydroxysuccinimide (OHSuc) was added to the reaction mixture in order to activate the remaining carboxylic groups of the glutamate monomers for subsequent conjugation of the E-[c(RGDfK)$_2$] peptide (SEQ ID NO:2). The carboxylic group activation is important in order to avoid side-reactions (namely cross linking between two E-[c(RGDfK)$_2$] compounds (SEQ ID NO:2) via the carboxylic groups of their aspartic acids). The reaction was allowed to proceed for 24 hours and was then stopped by pouring the reaction mixture into CHCl$_3$. The resulting precipitate was collected and washed with acetone and MeOH in order to remove the unreacted OHSuc. The precipitate was further collected and dried under vacuum. CHCl$_3$ was kept to determine total drug loading (PTX) by HPLC through an indirect measurement. The solid intermediate was redissolved in anhydrous DMF and E-[c(RGDfK)$_2$] peptide (SEQ ID NO:2) was conjugated with PGA through the -E-peptidic spacer using DMAP as a base catalyst. The reaction was allowed to proceed at room temperature for 72 hours and was then stopped by pouring the reaction mixture into CHCl$_3$. Thin layer chromatography (TLC, silica) showed complete conversion of the free E-[c(RGDfK)$_2$] ($R_f$=0.3) (SEQ ID NO:2) to the polymer conjugated E-[c(RGDfK)$_2$] (SEQ ID NO: 18) ($R_f$=0, AcOH/MeOH=1:99). The resulting precipitate was collected and dried in vacuum thus yielding the desired Compound 4. CHCl$_3$ was kept to determine total drug loading E-[c(RGDfK)$_2$] (SEQ ID NO:2) by HPLC through an indirect measurement.

The sodium salt of the PGA-PTX-E-[c(RGDfK)$_2$] (SEQ ID NO:47) conjugate was obtained by dissolving the product in 1.0 M NaHCO$_3$ followed by purification by SEC (Sephadex G25) in order to remove low molecular weight contaminants and salt excesses. Lyophilization of the purified fractions yielded the desired product as a white powder (70%-80% yield).

Synthesis of a Conjugate of PGA with a Single c(RGDfk) Moiety (SEQ ID NO:17)

PGA-RGDfk (SEQ ID NO:17; MW 200.37 g/mol) and the conjugate PGA-PTX-RGDfk (SEQ ID NO:19; MW 216.53 g/mol) were also similarly synthesized and the % of drug loading is presented in Table 1. The chemical structures of PGA-PTX-RGDfk conjugate (SEQ ID NO: 19) and the conjugate PGA-RGDfk (SEQ ID NO:17; are presented in FIGS. 2F and 2G, respectively.

Syntheses of "Control" Conjugates

For use as control compounds in the experiments described hereinbelow, other conjugates were also synthesized: PGA-PTX, PGA-c(RADfk) (SEQ ID NO:14), PGA-E-[c(RGDfk)$_2$] (SEQ ID NO:15) and PGA-PTX-c(RADfk) (SEQ ID NO:19). The chemical structures of PGA-PTX, PGA-c(RADfk) (SEQ ID NO:14) and PGA-E-[c(RGDfk)$_2$] (SEQ ID NO:15) conjugates is presented in FIGS. 2C, 2D and 2E respectively. The chemical structure of PGA-PTX-c(RADfk) conjugate (SEQ ID NO:19) is presented in FIG. 3B.

Example 3

Synthesis of PGA-E-[c(RDGfk)$_2$] (SEQ ID NO:15; Compound 5)

As discussed hereinabove, PGA-E-[c(RGDfk)$_2$] (SEQ ID NO:15; is a conjugate used as a control in experiments described hereinbelow which compare the activity of the free [c(RGDfk)$_2$] (SEQ ID NO:26) and the conjugated [c(RGDfk)$_2$] peptide (SEQ ID NO:15). The general synthesis of a PGA-E-[c(RGDfk)$_2$] (SEQ ID NO:15; Compound 5) is depicted in FIG. 8.

PGA was dissolved in anhydrous dimethylformamide (DMF) under nitrogen atmosphere and the glutamate carboxylic acids were activated using OHSuc. The reaction was allowed to proceed for 24 hours. The resultant PGA-OSuc product was isolated by precipitation in CHCl$_3$ and washed with acetone and methanol.

E-[c(RGDfK)$_2$] (SEQ ID NO: 2) was then conjugated through the succinimidyl-activated esters to the PGA in DMF, as follows: E-[c(RGDfK)$_2$] (SEQ ID NO: 2) was added to the PGA-OSuc and the reaction was allowed to proceed in DMF for 48 hours at room temperature. The reaction was stopped by pouring the reaction mixture into CHCl$_3$. Thin layer chromatography (TLC, silica) showed a complete conversion of the free E-[c(RGDfK)$_2$] (SEQ ID NO: 2) ($R_f$=0.3) to the polymer conjugated E-[c(RGDfK)$_2$] (SEQ ID NO: 15) ($R_f$=0, AcOH/MeOH=1:99). The resulting precipitate was collected and dried under vacuum thus yielding the desired Compound 5.

The sodium salt of the conjugate (SEQ ID NO:48) was obtained by dissolving the product in 1.0 M NaHCO$_3$, followed by purification by SEC (Sephadex G25) using water as mobile phase, in order to remove low molecular weight contaminants and salt excesses. Lyophilization of the purified fractions yielded the desired product as a white powder (70%-80% yield).

Example 4

Characterization of Drug Loading, Hydrodynamic Diameter and Enzymatic Cleavage of the Conjugates

Determination of PTX and of RGD- or RAD-Containing Moieties Loading

In order to keep an appropriate Paclitaxel loading, a maximum of 5 mol % E-[c(RGDfK)$_2$] (SEQ ID NO:2) loading was considered. The total PTX content in these polymeric conjugates was determined by UV (λ=227 nm and 230 nm, calibration curve carried out at RT in MeOH) and HPLC (indirect analysis wherein the PTX content in reaction residues at λ=220 nm, from 35 to 80% of acetonitrile in 25 min, r.t.=10.8 minutes).

The total E-[c(RGDfK)$_2$] peptide (SEQ ID NO:2), E-c (RGDfK) peptide (SEQ ID NO:41) or control inactive peptide, -c(RADfk) (SEQ ID NO:40) content in these polymeric conjugates was determined by UV (λ=254 nm and 260 nm, calibration curve carried out at RT in MeOH), HPLC (indirect analysis of peptide content in reaction residues, flow rate 1 ml/minute using an acetonitrile gradient in aqueous 0.1% TFA from 5 to 75% of acetonitrile in 25 min, λ=220 nm, r.t.=7.9 minutes) and amino acid analysis (briefly, 3 mg of each conjugate synthesized were hydrolyzed with 5N HCl at 160° C. for 4 hours, and samples were then lyophilized and sent to Parc Cientific Barcelona (Barcelona, Spain) for analysis by LC-MS).

The % loading of PTX and the peptides in the synthesized conjugates is presented in Table 1. Two PGA-PTX-E-[c(RGDfK)$_2$] conjugates (SEQ ID NO:18) were synthesized differing in the % loading of the PTX and E-[c(RGDfK)$_2$]. PTX was in the range of 2.6-5. mol % functionalization and the % loading of E-[c(RGDfK)$_2$] peptide (SEQ ID NO: 2) was in the range of 3.9-5.7 mol % functionalization (the first conjugate had a 5-4.7 mol % E-[c(RGDfk)$_2$] (SEQ ID NO: 2), and 2.6 mol % PTX loadings and the second conjugate had a 3.9 mol % E-[c(RGDfk)$_2$] (SEQ ID NO: 2) and 5.5 mol % PTX loadings) with a free drug content always less than 1.5 wt % of total drug.

[PGA-PTX-E-c(RGDfk)$_2$] (SEQ ID NO:18) with PTX loading of 2.6 mol % and -E-c(RGDfk)$_2$ loading of 5 mol % (i.e. first conjugate) was about 40 nm (see, FIG. 9B). The mean hydrodynamic diameter of the conjugate [PGA-PTX-E-c(RGDfk)] (SEQ ID NO:16) with PTX loading of 2.3 mol % and with -E-c(RGDfk) loading of 5 mol % was about 35 nm (see, FIG. 9C).

The average molecular weight (MW), polydispersity (Mw/Mn) and the behavior of PGA conjugates and control non-conjugated PGA in solution were analyzed by size exclusion chromatography (SEC). Both techniques showed that the PGA conjugates have a more compact conformational structure and greater sedimentation coefficient (S) as compared to the control nonconjugated PGA. The MW was determined, by SEC, as 17700 Da (MW/Mn=1.3) for PGA and 48600 Da (MW/Mn=1.4) for the PGA-PTX-c(RGDfk)$_2$ conjugate (SEQ ID NO:18) (the second conjugate) and 35700 Da (Mw/Mn=1.4) for PGA-E-[c(RGDfk)$_2$] conjugate (SEQ ID NO:15).

PTX Release from PGA Copolymer-E-c(RGD)$_2$-Paclitaxel Conjugate (SEQ ID NO:18) by Cathepsin B The ability of the conjugates of the present invention to release PTX in the presence of preselected cellular enzymes, for instance, the lysosomal enzyme cathepsin B, was tested. The results are presented in FIG. 10 and show that the conjugates synthesized exhibited a time-dependent and drug loading dependent drug release kinetics in the enzymatic experiments. It is important to mention that in all cases the main metabolite released from the polymer was PTX as deter-

TABLE 1

| Conjugate | Total PTX loading (mol %) | Total peptide loading (mol %) | | Free drug content (wt % of total drug)[c] | |
|---|---|---|---|---|---|
| | | | | PTX | Peptide |
| PGA-PTX | 4.9 ± 0.3[a] | NA | NA | 1.2 ± 0.4 | NA |
| PGA-c(RADfk) (SEQ ID NO: 14) | NA | 5.0 ± 0.3[a] | 5.1 ± 0.1[b] | NA | 0.9 ± 0.1 |
| PGA-c(RGDfk) (SEQ ID NO: 17) | NA | 5.0 ± 0.3[a] | 5.1 ± 0.1[b] | NA | 1.0 ± 0.2 |
| PGA-E-[c(RGDfk)$_2$] (SEQ ID NO: 15) | NA | 5.0 ± 0.3[a] | 5.7 ± 0.7[b] | NA | 0.8 ± 0.1 |
| PGA-PTX-c(RADfk) a | 2.3 ± 0.2[a] | 5.0 ± 0.3[a] | 4.9 ± 0.2[b] | 0.8 ± 0.2 | 0.9 ± 0.1 |
| PGA-PTX-c(RADfk) b SEQ ID NO: 19 | 5.5 ± 0.3[a] | 5.0 ± 0.2[a] | 4.3 ± 0.3[b] | 1.1 ± 0.3 | 0.7 ± 0.1 |
| PGA-PTX-c(RGDfk) (SEQ ID NO: 16) | 2.2 ± 0.4[a] | 5.0 ± 0.3[a] | 4.6 ± 0.5[b] | 1.2 ± 0.3 | 0.9 ± 0.2 |
| PGA-PTX-E-[c(RGDfk)$_2$] a | 2.6 ± 0.4[a] | 5.0 ± 0.1[a] | 4.7 ± 0.2[b] | 1.0 ± 0.3 | 0.8 ± 0.2 |
| PGA-PTX-E-[c(RGDfk)$_2$] b (SEQ ID NO: 18) | 5.5 ± 0.3[a] | 5.0 ± 0.3[a] | 3.9 ± 0.4[b] | 1.1 ± 0.3 | 0.8 ± 0.2 |

[a]Average value as determined by HPLC (indirect analysis) and UV spectroscopy (direct analysis).
[b]Determined by amino acid analysis.
[c]Determined by HPLC. Average of two different extraction procedures (see details above).
NA: not appropriate.

Hydrodynamic Diameter and Polydispersity of the Conjugates:

The hydrodynamic diameter and size distribution of a polydispersed population of nano-scale PGA-PTX-E-[c(RGDfk)$_2$] particles (SEQ ID NO:18) was assessed using laser light scattering microscopy with the Nanoparticle Tracking Analysis (NTA) technology (NanoSight LM20™, Salisbury, UK). The mean hydrodynamic diameter of the conjugate [PGA-PTX-E-c(RGDfk)$_2$] (SEQ ID NO:18) with PTX loading of 5.5 mol % and -E-c(RGDfk)$_2$ loading of 3.9 mol % (i.e. second conjugate) was about 30 nm (see, FIG. 9A). The mean hydrodynamic diameter of the conjugate mined by LC/MS experiments using a MALDI-TOF as MS detector. PGA-PTX-E-[c(RGDfk)$_2$] (SEQ ID NO:18; having 3.9 mol % E-[c(RGDfk)$_2$], 5.5 mol % PTX loadings) showed slightly faster release kinetics compared to all other conjugates, including PGA-PTX-E-c(RGDfk) (SEQ ID NO:16) (FIG. 2A). Interestingly, PTX release was greater with the second conjugate, bearing greater PTX loading (5.5 mol %) and lower E-[c(RGDfk)$_2$] content (3.9 mol %), after 48 hours as compared to the first conjugate synthesized having a lower PTX loading (2.6 mol %) and higher E-[c(RGDfk)$_2$] content (5 mol %). These differences could be due to a different conformation adopted as these polymer conjugates form unimolecular micelles in solution. For stability studies under hydrolytical conditions and in the presence of plasma, non-significant PTX release was observed in the conjugates analyzed (data not shown).

Example 5

Synthesis of Fluorescently Labeled Conjugates

A fluorescence probe, Oregon Green-cadaverine (OG), was conjugated to the various PGA conjugates through the free carboxylic groups, namely PGA-OG, PGA-c(RADfk)-OG (SEQ ID NO:24) and PGA-E-[c(RGDfk)$_2$]-OG (SEQ ID NO:25) were synthesized in order to study the cellular uptake and trafficking. The conjugates were dissolved in the minimum amount of anhydrous DMF, then N,N'-diisopropylcarbodiimmide (DIC) and 1'-hydroxybenzotriazole (HOBT) were added, using a DIC/HOBT/COOH groups molar ratio of 1.5:1.5:1. Finally, a DMF solution of Oregon Green-cadaverine (OG) was added with a OG/COOH groups molar ratio of 1:100. The reactions were monitored by TLC and eluted with MeOH followed by DMF evaporation by vacuum. The residues were dissolved in an aqueous solution of NaHCO$_3$ (1.5:1 molar ratio of NaHCO$_3$ and the COOH groups) and loaded onto a PD10 column, eluted with water, with collecting fractions of 1 ml to 2 µl of each fraction. 498 µl of MeOH was added to each fraction, in order to measure the fluorescence and identify the fractions containing the PGA-OG conjugates and to quantify the amount of conjugated OG. OG loading ranged from 0.7 to 0.9 mol %.

Example 6

Anti-Angiogenesis Activity of HPMA Copolymer-c(RGDfk)$_2$-Paclitaxel Conjugate (SEQ ID NO:23)

The ability of Paclitaxel (PTX) and the cyclic RGD-containing peptide c(RGDfk)$_2$ when conjugated to the HPMA copolymer (SEQ ID NO:23), as compared to free Paclitaxel and c(RGDfk)$_2$, to inhibit endothelial and tumor cell proliferation, migration towards the chemoattractant vascular endothelial growth factor (VEGF) and to adhere to a fibrinogen matrix is tested in vitro.

Cell Proliferation Assay:

Human umbilical vein endothelial cells (HUVEC) or MCF7 or MCF7/Cyr61 breast cancer cells are seeded on gelatinized plates. Following 24 hours of incubation, cells are challenged with serial concentrations of either PTX or c(RGDfk)$_2$ (SEQ ID NO:26) or HPMA copolymer-c(RGDfk)$_2$-PTX (SEQ ID NO:23) in the presence of growth factors. Cells are counted after 72 hours using Beckman Culter Counter.

Migration Assay:

A migration assay is performed in order to evaluate the effect of free PTX, or c(RGDfk)$_2$ (SEQ ID NO:26) or HPMA copolymer-c(RGDfk)$_2$-PTX (SEQ ID NO:23) on the ability of breast tumor cells, MCF7 or MCF7/Cyr61 or HUVEC to migrate through endothelial cell monolayer in a transwell system using vascular endothelial growth factor (VEGF) as a migration stimulator in the bottom chamber. This imitates their ability to cross the endothelium and metastasize in vivo.

The cell migration assay is performed as described above for HUVEC. Briefly, HUVEC, MCF7 or MCF7/Cyr61 (5×10$^4$ cells/100 µl) are challenged with free PTX, c(RGDfk)$_2$ (SEQ ID NO:26), or HPMA copolymer-c (RGDfk)$_2$-PTX (SEQ ID NO:23), and are then plated on the upper chamber of the transwell for a 2 hours incubation period. Following incubation, cells are allowed to migrate to the underside of the chamber in the presence or absence of VEGF in the lower chamber. Cells are then fixed and stained and the number of migrated cells per membrane is determined. Migration is normalized to percent migration, with 100% representing VEGF dependent migration of cells which are not incubated with any compound.

Endothelial Cell Adhesion Assay:

The ability of c(RDGfk)$_2$ (SEQ ID NO:26), c(RDGfk)$_2$-Paclitaxel (SEQ ID NO:49) and HPMA copolymer-c (RGDfk)$_2$-Paclitaxel conjugate (SEQ ID NO:23) to inhibit endothelial cell adherence to a fibrinogen coated matrix is determined. Trypsinized HUVEC are incubated with the tested conjugate and with the inactive c(RADfk)$_2$ (SEQ ID NO: 50) or c(RADfk)$_2$-Paclitaxel (SEQ ID NO: 51) as controls. The treated HUVECs are then plated on fibrinogen-coated 96-well culture plates and allowed to attach. The attached cells are then fixed and dyed and their number is determined using Nikon TE2000E inverted microscope and NIH image software.

Example 7

Binding of PGA-Conjugated c(RGDfk)$_2$ to the αvβ3 Integrin Receptor

αvβ$_3$ integrin expression on HUVEC, U87 glioblastoma and PANC02 cells was determined using αvβ$_3$ integrin immunostaining and FACS. αvβ$_3$ integrin was highly expressed on HUVEC and U87 glioblastoma cells, but was absent from PANC02 cells (see, FIG. 11A).

Using amnis ImageStream 100 imaging flow cytometer and the fluorescence probe Oregon Green-cadaverine (OG), the interaction of PGA-OG, PGA-c(RADfk)-OG (SEQ ID NO:24) and PGA-E-[c(RGDfk)$_2$]-OG (SEQ ID NO:25) with αvβ$_3$ integrin receptor of the conjugates was evaluated in HUVEC. Conjugate-cell adherence was observed for PGA-E-[c(RGDfk)$_2$]-OG (SEQ ID NO:25) as early as 10 minutes following cell incubation with the conjugate, which further continued to enhance, thereby suggesting cell internalization of the conjugate. PGA-c(RADfk)-OG (SEQ ID NO:24) started adhering to cell surface a little later, at 15 minutes (see, FIGS. 11B and 11C). In contrast, the conjugate which did not comprise the RGD moiety (PGA-c(RADfk)-OG; SEQ ID NO:24) bound to a much lesser extent to the cells (see, FIG. 11B), thereby demonstrating a role for the RGD moiety in the interaction and subsequent internalizations of the conjugates into the cells, most likely via the αvβ$_3$ integrin receptor.

Example 8

Anti-Angiogenesis Activity of PGA-Copolymer-E-[c(RGDfk)$_2$]-Paclitaxel Conjugate (SEQ ID NO:18) Cell Proliferation Assay In order to evaluate whether similar to PTX, c(RGDfk)$_2$ (SEQ ID NO: 26) and PGA-E-[c(RGDfk)$_2$]-PTX, (SEQ ID NO:18) a representative conjugate according to the embodiments of the present invention, possesses anti-angiogenic properties, HUVEC proliferation, capillary-like tube formation and migration assays were performed. The cyclic peptide c(RADfk) (SEQ ID NO:40) served as a negative control for the -E-[c(RGDfk)$_2$] (SEQ ID NO:2) since this peptide has low affinity binding to integrin receptors. The activity of the PGA-E-[c(RGDfk)$_2$]-PTX conjugate (SEQ ID NO:18) was compared to the activity of the polyglutamate polymer alone (PGA), Paclitaxel alone (PTX), a conjugate of PGA-PTX, a conjugate of PGA with the negative control RAD containing peptide (PGA-c(RADfk); SEQ ID NO:14) and a conjugate of PGA with the bis-cyclic RGD-containing peptide (PGA-E-c(RGDfk)$_2$; SEQ ID NO:15). The chemical structure of these conjugates is presented in FIG. 2. The activity of the PGA-E-[c(RGDfk)$_2$]-PTX conjugate (SEQ ID NO:18) was also compared to a similar conjugate only with the RGD-containing peptide being replaced by the negative control RAD peptide (SEQ ID NO:19) (chemical structures of these two conjugates are presented in FIG. 3). The IC$_{50}$ values measured for the tested conjugates are presented in Table 2. Table 2 presents data for 5 experiments performed, whereby in each experiment the IC$_{50}$ of the various compounds (detailed on the left column) were compared to the IC$_{50}$ of a specific conjugate using a specific cell line (as indicated in the upper first and second rows). When the conjugate comprised only one RGD moiety than it was compared to control compounds comprising only one RGD moiety (i.e. the x in Table 2 equals 1). When the conjugate comprised two RGD moieties than it was compared to control compounds also comprising two RGD moieties (i.e. the x in Table 2 equals 2).

The proliferation of HUVEC was inhibited similarly by the PGA-PTX, PGA-PTX-E-[c(RGDfk)$_2$] (SEQ ID NO:18) and PGA-PTX-c(RADfk) (SEQ ID NO:19) conjugates at PTX equivalent concentrations in which more than 50% of the cells were inhibited at concentrations lower than 0.2 and higher than 17 nM (see, FIG. 12A). Free PTX by itself and in combination with E-[c(RGDfk)$_2$] (SEQ ID NO:2) or c(RADfk) (SEQ ID NO:40) inhibited HUVEC proliferation more efficiently, demonstrating an IC$_{50}$ value of about 0.01 nM PTX. E-[c(RGDfK)$_2$] peptide, alone (SEQ ID NO:2) or conjugated to PGA (SEQ ID NO:15), inhibited HUVEC proliferation by itself but only at high concentrations. c(RADfk) peptide (SEQ ID NO:40), or PGA showed no effect even at those high concentrations (for IC$_{50}$ values see, Table 2).

For U87 cells, another $\alpha v \beta_3$ expressing cell type, proliferation inhibition was very similar to that of HUVEC. Free PTX, or combined with E-[c(RGDfk)$_2$] (SEQ ID NO:2) or c(RADfk) (SEQ ID NO:40) at equivalent doses had similar effect, exhibiting an IC$_{50}$ of about 0.01 nM PTX, as it was for HUVEC. Moreover, PGA-PTX, PGA-PTX-E-[c(RGDfk)$_2$] and PGA-PTX-c(RADfk) conjugates (SEQ ID NOs:18 and 19 respectively) at equivalent doses had an exact similar bell-shaped effect, as was seen on HUVEC, in which more than 50% of the cells were inhibited at concentrations lower than about 0.055 and higher than 70 nM PTX (FIG. 12B).

A different inhibition pattern was seen for the non-expressing $\alpha v \beta_3$ PANC02 cells. Free PTX, or combined with E-[c(RGDfk)$_2$] or c(RADfk) (SEQ ID NOs:2 and 40 respectively) at equivalent doses inhibited cells proliferation with an IC$_{50}$ of about 200 nM PTX. As opposed to HUVEC and U87 cells, PGA-PTX-E-[c(RGDfk)$_2$] conjugate (SEQ ID NO:18) had a more significant effect with IC$_{50}$ of about 650 nM PTX, were PGA-PTX and PGA-PTX-c(RADfk) (SEQ ID NO: 19) had an IC$_{50}$ of about 2000 nM PTX (FIG. 12C). On these cells, bell-shaped pattern of conjugate inhibition was not observed.

These results show that the anti-angiogenesis agent Paclitaxel maintained its anti-proliferative activity when conjugated, together with the angiogenesis targeting moiety c(RGDfk)$_2$ (SEQ ID NO:26), to a PGA polymer.

TABLE 2

| | IC50 (nM) of PGA-PTX-E-c(RGDfk) (SEQ ID NO: 16) 2.1 mol % PTX, 5 mol % RGD | IC50 (nM) of PGA-PTX-E-[c(RGDfk)$_2$] (SEQ ID NO: 18) 2.6 mol % PTX, 5 mol % RGD | IC50 (nM) of PGA-PTX-E-[c(RGDfk)$_2$] (SEQ ID NO: 18) 5 mol % PTX, 3.9 mol % RGD | IC50 (nM) of PGA-PTX-E-[c(RGDfk)$_2$] (SEQ ID NO: 18) 5 mol % PTX, 3.9 mol % RGD | IC50 (nM) of PGA-PTX-E-[c(RGDfk)$_2$] (SEQ ID NO: 18) 5 mol % PTX, 3.9 mol % RGD |
|---|---|---|---|---|---|
| Cell type | HUVEC | HUVEC | HUVEC | U87 | PANC02 |
| PGA | NA | NA | NA | NA | NA |
| c(RADfK) (SEQ ID NO: 40) | NA | NA | NA | NA | NA |
| E-[c(RGDfK)$_x$] X = 1 or 2 (SEQ ID NOs: 41 or 2 respectively) | NA | 8000 | 4000 | NA | NA |
| PTX | 0.0085 | 0.01 | 0.009 | 0.045 | 200 |
| PGA-E-[c(RGDfK)$_x$] X = 1 or 2 (SEQ ID NOs: 17 or 15 respectively) | NA | 2900 | 7000 | NA | NA |
| PGA-c(RADfK) (SEQ ID NO: 14) | 1000 | 5000 | NA | NA | NA |
| PGA-PTX | 0.38 -- 10 | 0.23 -- 20 | 0.4 -- 15 | 0.1 -- 80 | 2000 |
| PTX + c(RADfK) (SEQ ID NO: 40) | 0.0085 | 0.02 | 2 | 0.9 | 110 |

TABLE 2-continued

| | IC50 (nM) of PGA-PTX-E-c(RGDfk) (SEQ ID NO: 16) 2.1 mol % PTX, 5 mol % RGD | IC50 (nM) of PGA-PTX-E-[c(RGDfk)₂] (SEQ ID NO: 18) 2.6 mol % PTX, 5 mol % RGD | IC50 (nM) of PGA-PTX-E-[c(RGDfk)₂] (SEQ ID NO: 18) 5 mol % PTX, 3.9 mol % RGD | IC50 (nM) of PGA-PTX-E-[c(RGDfk)₂] (SEQ ID NO: 18) 5 mol % PTX, 3.9 mol % RGD | IC50 (nM) of PGA-PTX-E-[c(RGDfk)₂] (SEQ ID NO: 18) 5 mol % PTX, 3.9 mol % RGD |
|---|---|---|---|---|---|
| PTX + E-[c(RGDfK)$_X$] X = 1 or 2 (SEQ ID NOs: 41 or 2 respectively) | 0.006 | 0.017 | 0.05 | 0.07 | 680 |
| PGA-PTX-c(RADfk) SEQ ID NO: 19 | 0.42 -- 10 | 0.19 -- 19 | 0.38 -- 18 | 65 | 2600 |
| PGA-PTX-E-[c(RGDfK)$_X$] X = 1 or 2 (SEQ ID NOs: 16 or 18 respectively) | 0.28 -- 20 | 25 | 0.2 -- 18 | 0.055 -- 70 | 650 |

IC$_{50}$ values for all the compounds and all combinations were calculated from the proliferation assays results.
The presented data is for the different loading percentage of PTX and the different loading percentage of E-[c(RGDfk)₂] or E-c(RGDfk).
NA- Non applicable, did not reach IC$_{50}$ in the concentrations used.

Similar results on HUVEC proliferation were obtained for the PGA-PTX-E-[c(RGDfk)₂] conjugate (SEQ ID NO:18) having a 5 mol % E-[c(RGDfk)₂] and 2.6 mol % PTX loading (see, FIG. 13A) as well as for the PGA-PTX-E-c(RGDfk) conjugate (SEQ ID NO:16) (see, FIG. 13B) whereby both showed a similar bell shaped effect, with an IC$_{50}$ of ~0.2 and 20 nM PTX respectively.

Example 9

Anti-Angiogenesis Activity of PGA-Copolymer-E-[c(RGDfk)₂]-Paclitaxel Conjugate Migration Assay Next, the effect of PGA-E-[c(RGDfk)₂]-PTX conjugate on the ability of HUVEC to migrate towards VEGF was tested. PGA-E-[c(RGDfk)₂]-PTX conjugate (5 mol % E-[c(RGDfk)₂], 2.6 mol % PTX loadings i.e. second conjugate synthesized) at equivalent concentrations of 100 nM PTX, inhibited the migration of HUVEC towards VEGF by about 40% (see, FIG. 14). PTX alone, the combination of PTX and -E-[c(RGDfk)₂] or c(RADfk) and PGA-PTX conjugate had greater inhibitory effect of about 55%. PGA served as control and had no inhibitory effect on the ability of HUVEC to migrate towards VEGF while -E-[c(RGDfk)₂] and c(RADfk) had an inhibitory effect of about 30%.

These results show that the anti-angiogenesis agent Paclitaxel as well as the c(RGDfk)₂ peptide both inhibited endothelial cell migration, although the latter to a lesser extent. Furthermore, Paclitaxel inhibition ability was preserved when conjugated together with c(RGDfk)₂ to the PGA.

These results show that the anti-angiogenesis agent Paclitaxel as well as the c(RGDfk)₂ peptide (SEQ ID NO: 26) both inhibited endothelial cell migration, although the latter to a lesser extent. Furthermore, Paclitaxel inhibition ability was preserved when conjugated together with c(RGDfk)₂ (SEQ ID NO:26) to the PGA.

Example 10

Anti-Angiogenesis Activity of PGA-Copolymer-E-[c(RGDfk)₂]-Paclitaxel Conjugate (SEQ ID NO:18) Endothelial Cell Adhesion Assay One of the principle stages of angiogenesis involves the adhesion of endothelial cell to the extracellular matrix and is mediated through integrin receptors. Therefore, drugs which interact and inhibit the activity of the integrin receptor inhibit endothelial cell adhesion and consequently, serve as antiangiogenesis agents. $\alpha_v\beta_3$ integrins are known to bind the RGD sequence (Arg-Gly-Asp; SEQ ID NO:1), which constitutes the recognition domain of different proteins, such as laminin, fibronectin and vitronectin. Tumor-induced angiogenesis can be targeted in vivo by antagonizing the $\alpha v\beta_3$ integrin with small peptides containing the RGD amino acid sequence (SEQ ID NO:1).

Therefore, endothelial cell adhesion assay was performed in order to evaluate in vitro the targeting specificity (i.e. ability to bind to the integrin receptors) of the cyclic RGD containing peptides -E-[c(RGDfk)₂] (SEQ ID NO:2) or c(RGDfk) (SEQ ID NO:9) when conjugated to PTX and PGA.

Presented in FIG. 15 are bar graphs of the percent of observed cell adhesion of HUVEC to fibrinogen coated plates when incubated with one of the tested compounds. The results were normalized to the percent of cell adhesion when no compound was added. All RGD-bearing PGA-PTX conjugates at equivalent concentrations of 50 μM RGD were able to inhibit HUVEC adhesion to fibrinogen by ~60%. PGA-PTX-c(RADfk) conjugate (SEQ ID NO:19) served as control to each RGD conjugate. When PGA-PTX-c(RADfk) conjugate (SEQ ID NO:19) was compared to bis-cyclic RGD-bearing conjugates, with a similar amount of PTX, it had a minor inhibitory effect of ~20%. When it was compared to monocyclic RGD-bearing conjugate, with a similar amount of PTX, it inhibited HUVEC adhesion as well as PGA-PTX-E-c(RGDfk) (SEQ ID NO:16) (~50%). Free PTX, as PGA, and all their combinations, had a negligent effect on endothelial cell adhesion. The free peptides E-[c(RGDfK)$_2$] (SEQ ID NO:2) or E-c(RGDfk) (SEQ ID NO:41) and c(RADfK) (SEQ ID NO:40) served as controls. As expected, the RGD peptidomimetics completely abrogated HUVEC adhesion at 50 μM while at the same concentration the c(RADfK) peptide (SEQ ID NO:40) had no effect on the adhesion of the cells The first PGA-PTX-E-[c(RGDfk)$_2$] conjugate (SEQ ID NO:18; having a loading of 3.9 mol % E-[c(RGDfk)$_2$] and 5.5 mol % PTX) was more effective than the second PGA-PTX-E-[c(RGDfk)$_2$] conjugate synthesized (SEQ ID NO:18; having a loading of 5 mol % E-[c(RGDfk)$_2$], and 2.6 mol % PTX). Both conjugates inhibited the adhesion more effectively than the monocyclic RGDfk peptide conjugate PGA-PTX-E-c(RGDfk) (SEQ ID NO:16).

These results show that the cyclic peptides E-[c(RGDfk)$_2$] (SEQ ID NO:2) and c(RGDfk) (SEQ ID NO:9) maintained the ability to bind $\alpha_v\beta_3$ integrins and inhibit endothelial cell adhesion when conjugated together with PTX to a PGA polymer (SEQ ID NOs: 18 and 16 respectively).

Example 11

Anti-Angiogenesis Activity of
PGA-Copolymer-E-[c(RGDfk)$_2$]-Paclitaxel
Conjugate (SEQ ID NO:18)

Capillary-Like Tube Formation of Endothelial Cells
In Vitro

Having shown that conjugated PTX and [c(RGDfk)$_2$] (SEQ ID NO: 26) have anti-angiogenic potential by inhibiting the proliferation, adhesion and migration of HUVEC, the effect of the PGA-E-[c(RGDfk)$_2$]-PTX conjugate (SEQ ID NO:18) on the ability of HUVEC to form capillary-like tube structures on Matrigel was examined (see, FIG. 16). This assay aims to imitate the capability of endothelial cells to form 3-D vascular structures in vivo as an important step in the angiogenic cascade. PGA-E-[c(RGDfk)$_2$]-PTX conjugate (SEQ ID NO:18; 5 mol % E-[c(RGDfk)$_2$], 2.6 mol % PTX loadings i.e. second conjugate synthesized), PGA-c(RADfk)-PTX conjugate (SEQ ID NO:19) as control, and the combinations of PTX and E-[c(RGDfk)$_2$] (SEQ ID NO:2) at equivalent concentrations of 10 nM and 19 nM, respectively, inhibited the formation of tubular structures of HUVEC by about 40% (see, FIG. 16B). PTX alone had greater inhibitory effect of about 50% and PGA, which served as control, had no inhibitory effect on the ability of HUVEC to form tubular structures.

These results show that Paclitaxel maintained its inhibitory effect on the ability of endothelial cell to form capillary-like tube structures, when conjugated with E-[c(RGDfk)$_2$] to a PGA polymer (SEQ ID NO:18).

Example 12

Specific Antagonism of $\alpha v\beta 3$

Cyr61 (also known as CCN1) is a Cysteine-rich matricellular protein that supports cell adhesion and induces adhesion signaling. Furthermore, Cyr61 stimulates endothelial cell migration and enhances growth factor induced DNA synthesis in culture and therefore induces angiogenesis in vivo. Mechanistically, Cyr61 acts as a non-RGD-containing ligand of integrin receptors. Functional blockade of $\alpha v\beta 3$, a Cyr61 integrin receptor, is specifically cytotoxic towards Cyr61-overexpressing breast cancer cells and a specific $\alpha v\beta 3$-RGD peptidomimetic agent (SEQ ID NO:28) prevents $\alpha v\beta 3$ from binding to its ligand, Cyr61.

The ability of HPMA copolymer-c(RGDfk)$_2$-Paclitaxel conjugate (SEQ ID NO:23), PGA copolymer-E-c(RGDfk)$_2$-Paclitaxel (SEQ ID NO:18) and the polymer PGA copolymer-E-c(RGDfk)-Paclitaxel conjugate (SEQ ID NO:16) to act as a specific antagonist of $\alpha v\beta 3$ and thus to inhibit the Cyr61-integrin receptor signal transduction cascade is evaluated in CYR61-overexpressing and control MCF-7 cells.

Downregulation of PI-3'K and ERK1/ERK2 Cascades:
Some of the phenotypic changes dictated by the Cyr61-driven $\alpha v\beta 3$ signaling, like enhanced endothelial cell survival and proliferation, are dependent upon activation of phosphatidylinositol 3'-kinase (PI-3'K/AKT) and ERK1/ERK2 MAPK cascades. Those pathways were recently found to be unregulated in Cyr61-overexpressing MCF-7 cells. Based on those findings, the same cell line is used to analyze the efficacy of the conjugates as $\alpha v\beta_3$ antagonists. Protein extracts are prepared from Cyr61-overexpressing MCF-7 cells before and after treatment with the conjugates, and the levels of PI-3'K/AKT and ERK1/ERK2 MAPK activation is monitored by Western blot.

Enhancement of the Apoptosis Level:
Functional blockade of $\alpha_v\beta_3$ synergistically enhances Paclitaxel-induced apoptosis in Cyr61-overexpressing breast cancer cells. Thus, the apoptosis level of Cyr61-overexpressing and control MCF-7 cells is analyzed by flow cytometry, before and after treatment with the conjugates. Cell extracts are also analyzed by Western blot for the expression level of different apoptotic proteins, like Bax, cleaved-PARP and several caspases.

p53 Accumulation:
Paclitaxel-induced apoptosis involves a dose- and time-dependent accumulation of the tumor suppressor p53. $\alpha v\beta_3$ hyperactivation by Cyr61 overexpression impairs Paclitaxel-induced accumulation of p53. Using western blotting techniques, the level of p53 protein, in cell extracts of CYR61-overexpressing MCF-7 cells in the presence/absence of the conjugates is evaluated.

Example 13

Evaluation of Antitumor Activity of the Conjugates
in Mice Bearing Mammary Tumors Paclitaxel has already been used successfully in the treatment of breast cancer both in animal models and in the clinic. SCID mice bearing MCF or MCF/Cyr61-Luciferase breast cancer cells in the mammary fat pad are treated with free Paclitaxel, Paclitaxel-c(RDGfk)$_2$ conjugate (SEQ ID NO:49), HPMA copolymer-c(RGDfk)$_2$-Paclitaxel conjugate (SEQ ID NO:23), PGA copolymer-E-c(RGDfk)-Paclitaxel (SEQ ID NO:16) or PGA copolymer-E-c(RGDfk)$_2$-Paclitaxel (SEQ ID NO:18), in the following manner: the animals are treated with one of the tested drugs at a equivalent dose of Paclitaxel (5 mg/kg weekly). Animals treated with saline, HPMA copolymer, PGA or c(RDGfk)$_2$ (SEQ ID NO:26) are used as controls. The animals are monitored daily for general health, weight loss and tumor progression. Once a week the mice are imaged following administration of luciferase i.v. using the Biospace Photon Imager in order to follow up the tumor progression. All treatments are evaluated at three time points: (i) early treatment at the hyperplasic stage (10 days after tumor cells inoculation) in order to block the angiogenic switch before the initial formation of solid tumors (prevention trial), (ii) treatment of mice bearing small (asymptomatic) solid tumors (15-30 days after tumor cells inoculation) in order to determine whether their expansive growth and progression to deleterious stages could be inhibited (intervention trial), and (iii) treatment of mice with substantial tumor burden and near death (around 45 days after tumor cells inoculation) to ascertain whether these conjugates can induce tumor regression (regression trial). At termination, animals are examined by post-mortem; tumors are dissected and analyzed by: a) immunohistochemistry: PCNA for proliferation, TUNEL for apoptosis, CD-31 for vessel density quantification; b) ELISA of angiogenic growth factors (VEGF, bFGF, TGF-β) to evaluate the effects of the therapy on those angiogenic factors and prognosis markers (kits by R&D); c) FACS analysis and Western blotting to determine the αvβ3 expression and phosphorylation changes before and after therapy.

Example 14

Evaluation of Antitumor Activity of the PGA-PTX-E-[c(RGDfk)$_2$]Conjugate in Mice Bearing Human Osteosarcoma Tumors In vivo evaluation of RGD-bearing conjugates was preformed in two methods: First, confocal microscopy analysis of mCherry labeled tumors dissected from mice treated with PGA-E-[c(RGDfk)$_2$]-OG (SEQ ID NO: 25) revealed high accumulation of the conjugate at the tumor site, as opposed to PGA-c(RADfk)-OG (SEQ ID NO:24) or PGA-OG conjugates (see, FIG. 17A). Second, the mCherry-labeled-MG63 cells from homogenized tumors treated with PGA-PTX-OG different conjugates were FACS-sorted by ImageStrim. The results show that PGA-PTX-E-[c(RGDfk)$_2$]-OG (SEQ ID NO:25) efficiently interacts with tumor cells compared with PGA-PTX-c(RADfk)-OG (SEQ ID NO:24) and PGA-PTX-OG (see, FIG. 17B).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A conjugate having the structure:

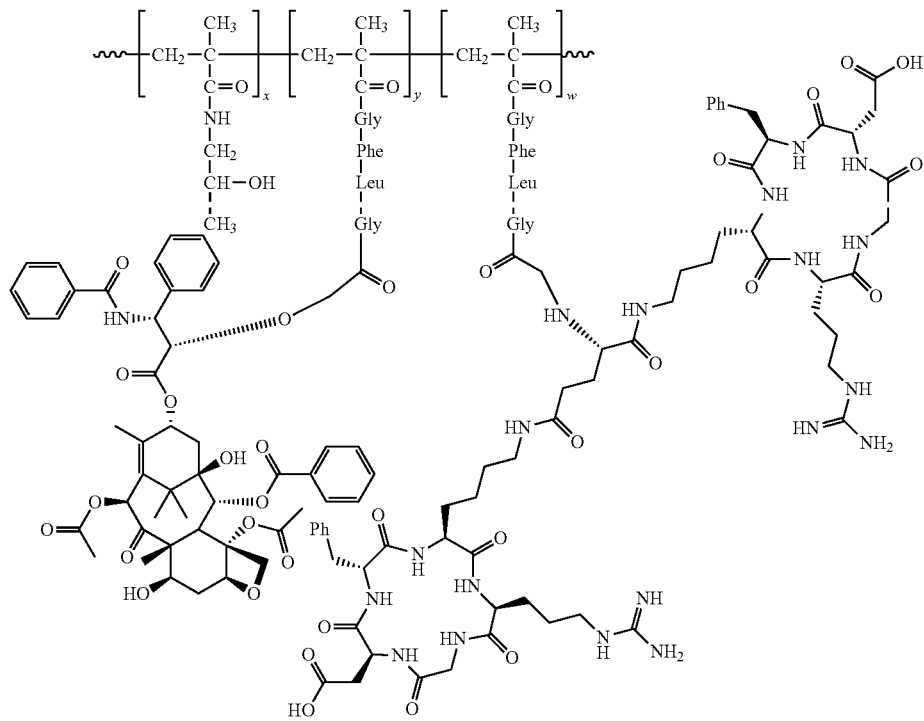

wherein:
x is an integer having a value such that x/(x+y+w) multiplied by 100 is in the range of from 0.01 to 99.9;
y is an integer having a value such that y/(x+y+w) multiplied by 100 is in the range of from 0.01 to 99.9; and 10. The method of claim 8, for monitoring the level of angiogenesis in a condition selected from the group consisting of atherosclerosis, cancer, hypertension, rheumatoid arthritis, diabetes and diabetes related complications.

11. A conjugate having the structure:

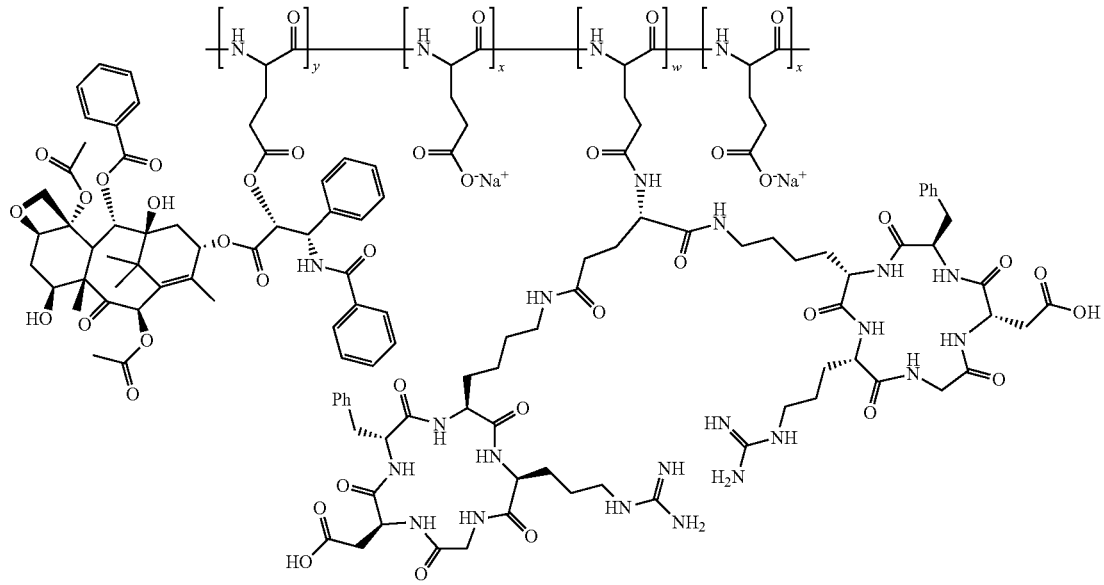

w is an integer having a value such that w/(x+y+w) multiplied by 100 is in the range of from 0.01 to 99.9.

2. The conjugate of claim 1, further comprising a labeling agent attached thereto.

3. A pharmaceutical composition comprising, as an active ingredient, the conjugate of claim 1 and a pharmaceutically acceptable carrier.

4. The pharmaceutical composition of claim 3, being packaged in a packaging material and identified in print, in or on said packaging material, for use in the treatment of a medical condition associated with angiogenesis.

5. The pharmaceutical composition of claim 4, wherein said conjugate comprises a labeling agent, the composition being packaged in a packaging material and identified in print, in or on said packaging material, for use in monitoring a medical condition associated with angiogenesis.

6. The pharmaceutical composition of claim 4, wherein said condition is selected from a group consisting of atherosclerosis, cancer, hypertension, rheumatoid arthritis, diabetes and diabetes related complications.

7. A method of treating a medical condition associated with angiogenesis in a subject in need thereof, the method comprising administering to the subject a therapeutically effective amount of the conjugate of claim 1.

8. A method of monitoring the level of angiogenesis within a body of a patient, the method comprising:
administering to the patient the conjugate of claim 2; and
employing an imaging technique for monitoring a distribution of the conjugate within the body or within a portion thereof.

9. The method of claim 7, wherein said condition is selected from the group consisting of atherosclerosis, cancer, hypertension, rheumatoid arthritis, diabetes and diabetes related complications.

wherein:
x is an integer having a value such that x/(x+y+w) multiplied by 100 is in the range of from 70 to 99.9;
y is an integer having a value such that y/(x+y+w) multiplied by 100 is in the range of from 0.01 to 15; and
w is an integer having a value such that w/(x+y+w) multiplied by 100 is in the range of from 0.01 to 15.

12. The conjugate of claim 11, further comprising a labeling agent attached thereto.

13. A pharmaceutical composition comprising the conjugate of claim 11 and a pharmaceutically acceptable carrier.

14. The pharmaceutical composition of claim 13, being packaged in a packaging material and identified in print, in or on said packaging material, for use in the treatment of a medical condition associated with angiogenesis.

15. The pharmaceutical composition of claim 13, wherein said conjugate comprises a labeling agent, the composition being packaged in a packaging material and identified in print, in or on said packaging material, for use in monitoring a medical condition associated with angiogenesis.

16. The pharmaceutical composition of claim 13, wherein said condition is selected from a group consisting of atherosclerosis, cancer, hypertension, rheumatoid arthritis, diabetes and diabetes related complications.

17. A method of treating a medical condition associated with angiogenesis in a subject in need thereof, the method comprising administering to the subject a therapeutically effective amount of the conjugate of claim 11.

18. A method of monitoring the level of angiogenesis within a body of a patient, the method comprising:
administering to the patient the conjugate of claim 12; and
employing an imaging technique for monitoring a distribution of the conjugate within the body or within a portion thereof.

19. The method of claim 17, wherein said condition is selected from the group consisting of atherosclerosis, cancer, hypertension, rheumatoid arthritis, diabetes and diabetes related complications.

\* \* \* \* \*